United States Patent
Mueller et al.

(10) Patent No.: US 10,171,734 B2
(45) Date of Patent: Jan. 1, 2019

(54) ROTATABLE IMAGING SYSTEM

(71) Applicant: oVio Technologies, LLC, Newport Beach, CA (US)

(72) Inventors: Gregory Paul Mueller, West Hollywood, CA (US); Ted Gagliano, West Hollywood, CA (US); Glenn D. Derry, Van Nuys, CA (US); Gary Martinez, Van Nuys, CA (US); Steve Hai Jiang, Van Nuys, CA (US); Mitchell Loveall, Van Nuys, CA (US)

(73) Assignee: OVIO TECHNOLOGIES, INC., Newport Beach, CA (US)

( * ) Notice: Subject to any disclaimer, the term of this patent is extended or adjusted under 35 U.S.C. 154(b) by 7 days.

(21) Appl. No.: 15/231,640

(22) Filed: Aug. 8, 2016

(65) Prior Publication Data
US 2016/0353022 A1    Dec. 1, 2016

Related U.S. Application Data

(63) Continuation-in-part of application No. 14/740,087, filed on Jun. 15, 2015, now Pat. No. 9,408,540, which
(Continued)

(51) Int. Cl.
*H04N 5/232* (2006.01)
*G03B 37/02* (2006.01)
(Continued)

(52) U.S. Cl.
CPC ....... *H04N 5/23238* (2013.01); *A61B 5/0064* (2013.01); *A61B 5/0077* (2013.01);
(Continued)

(58) Field of Classification Search
CPC ..................................................... H04N 19/02
See application file for complete search history.

(56) References Cited

U.S. PATENT DOCUMENTS

| 706,459 A | 8/1902 | Selke |
| 2,140,602 A | 10/1937 | Simjian |
(Continued)

FOREIGN PATENT DOCUMENTS

| CN | 101794069 | 8/2010 |
| DE | 102007052300 | 5/2009 |
(Continued)

OTHER PUBLICATIONS

CN201380021017.9 Office Action dated Aug. 29, 2016.
(Continued)

*Primary Examiner* — Kate H Luo
(74) *Attorney, Agent, or Firm* — Jeffer Mangels; Butler & Mitchell LLP; Brennan C. Swain, Esq.

(57) ABSTRACT

An imaging system that includes a rotating unit that includes an imaging camera, an alignment camera and at least a first monitor. The rotating unit is rotatable between a home position and a finish position about a rotation axis such that the imaging camera can capture a first scan. The alignment camera is directed generally downwardly and is configured to capture a first alignment image of a subject positioned generally co-axially with the rotation axis. The first alignment image is displayed on the first monitor.

20 Claims, 56 Drawing Sheets

Related U.S. Application Data is a continuation-in-part of application No. 14/559,827, filed on Dec. 3, 2014, now Pat. No. 9,060,125, which is a continuation-in-part of application No. 13/779,543, filed on Feb. 27, 2013, now Pat. No. 9,207,518.

(60) Provisional application No. 61/911,402, filed on Dec. 3, 2013, provisional application No. 61/603,853, filed on Feb. 27, 2012, provisional application No. 61/667,108, filed on Jul. 2, 2012.

(51) Int. Cl.

| | |
|---|---|
| G06T 11/60 | (2006.01) |
| H04N 5/225 | (2006.01) |
| A61B 5/00 | (2006.01) |
| A61B 5/107 | (2006.01) |
| F16M 11/04 | (2006.01) |
| F16M 11/18 | (2006.01) |
| F16M 11/20 | (2006.01) |
| F16M 11/28 | (2006.01) |
| F16M 11/42 | (2006.01) |
| F16M 13/02 | (2006.01) |
| G03B 15/06 | (2006.01) |
| G03B 17/56 | (2006.01) |
| H04N 7/18 | (2006.01) |
| A61B 90/30 | (2016.01) |
| A61B 90/00 | (2016.01) |

(52) U.S. Cl.
CPC .......... *A61B 5/1079* (2013.01); *A61B 5/6889* (2013.01); *A61B 90/30* (2016.02); *A61B 90/39* (2016.02); *F16M 11/046* (2013.01); *F16M 11/048* (2013.01); *F16M 11/18* (2013.01); *F16M 11/2014* (2013.01); *F16M 11/2021* (2013.01); *F16M 11/28* (2013.01); *F16M 11/42* (2013.01); *F16M 13/02* (2013.01); *F16M 13/027* (2013.01); *G03B 15/06* (2013.01); *G03B 17/561* (2013.01); *G03B 37/02* (2013.01); *G06T 11/60* (2013.01); *H04N 5/225* (2013.01); *H04N 5/2251* (2013.01); *H04N 5/23293* (2013.01); *H04N 7/18* (2013.01); *A61B 2090/3937* (2016.02); *G06T 2207/30204* (2013.01)

(56) References Cited

U.S. PATENT DOCUMENTS

| | | | |
|---|---|---|---|
| 2,448,084 A | | 8/1948 | Davis |
| 3,690,242 A | | 9/1972 | Cruickshank |
| 3,970,835 A | | 7/1976 | Crete |
| 4,236,795 A | * | 12/1980 | Kephart .................. G03B 15/06 |
| | | | 396/3 |
| 4,302,097 A | | 11/1981 | Chlestil |
| 4,571,638 A | | 2/1986 | Schneider et al. |
| 5,325,193 A | | 6/1994 | Pritchard et al. |
| 5,457,370 A | | 10/1995 | Edwards |
| 6,633,328 B1 | | 10/2003 | Byrd |
| 6,834,960 B2 | | 12/2004 | Dbjay |
| 6,969,033 B2 | | 11/2005 | van der Linden |
| 7,039,220 B2 | * | 5/2006 | Kriesel .................. A01K 29/00 |
| | | | 382/110 |
| 7,406,257 B2 | * | 7/2008 | Yi .......................... H04N 9/3176 |
| | | | 348/E5.026 |
| 7,502,174 B2 | * | 3/2009 | Jensen .................... A61B 6/04 |
| | | | 348/370 |
| 7,720,554 B2 | | 5/2010 | DiBernardino |
| 8,144,231 B2 | | 3/2012 | Miyashita |
| 8,462,206 B1 | * | 6/2013 | McGuire .............. G06T 1/0007 |
| | | | 348/135 |
| 2002/0135776 A1 | * | 9/2002 | Nishi .................. G03F 7/70775 |
| | | | 356/500 |
| 2004/0036841 A1 | | 2/2004 | Dbjay |
| 2004/0037468 A1 | | 2/2004 | Morishima |
| 2006/0147188 A1 | | 7/2006 | Weng |
| 2006/0244749 A1 | * | 11/2006 | Kondo .................... G06T 15/20 |
| | | | 345/427 |
| 2007/0098378 A1 | | 5/2007 | Giacomuzzi |
| 2007/0177780 A1 | | 8/2007 | Chui |
| 2008/0121819 A1 | * | 5/2008 | Tanaka ................ B23K 26/0738 |
| | | | 250/492.2 |
| 2010/0066676 A1 | | 3/2010 | Kramer et al. |
| 2010/0232773 A1 | | 9/2010 | DePaula |
| 2011/0013197 A1 | | 1/2011 | Schwarz et al. |
| 2011/0069880 A1 | * | 3/2011 | Sergieiev ................ F16M 11/10 |
| | | | 382/154 |
| 2011/0074674 A1 | * | 3/2011 | Walberg ................ G06F 3/0418 |
| | | | 345/158 |
| 2011/0116782 A1 | | 5/2011 | Scott |
| 2011/0256927 A1 | * | 10/2011 | Davis .................... A63F 9/0468 |
| | | | 463/34 |
| 2012/0176515 A1 | | 7/2012 | Teo |
| 2013/0222684 A1 | | 8/2013 | Mueller et al. |
| 2015/0077564 A1 | * | 3/2015 | Swindord ................ H04N 7/18 |
| | | | 348/148 |

FOREIGN PATENT DOCUMENTS

| | | |
|---|---|---|
| JP | 401092732 | 4/1989 |
| JP | 2002280440 | 9/2002 |
| JP | 2004057614 | 2/2004 |
| JP | 2005038293 | 2/2005 |
| JP | 2005316051 | 11/2005 |
| JP | 200988831 A | 8/2009 |
| KR | 20070025045 | 3/2007 |
| KR | 20100011301 | 2/2010 |

OTHER PUBLICATIONS

Extended European Search Report issued in EP 14868344.4 dated Aug. 7, 2017.
KR 10-2014-7026755 Office Action dated Aug. 8, 2017.
Adobe Systems Incorporated, "Adobe SpeedGrade CS6: Craft the perfect look for every production," 2012: 1-9.
X-Rite GreagMacbeth ColorChecker Passport, Sep. 18, 2009, https://www.youtube.com/watch?v=fSo_Gq_sap8&feature=youtu.be.
PCT/US2013/028092 ISR and Written Opinion dated May 9, 2013.
PCT/US2014/068456 ISR and Written Opinion dated Apr. 16, 2015.
SG11201604385X Written Opinion dated May 5, 2017.

* cited by examiner

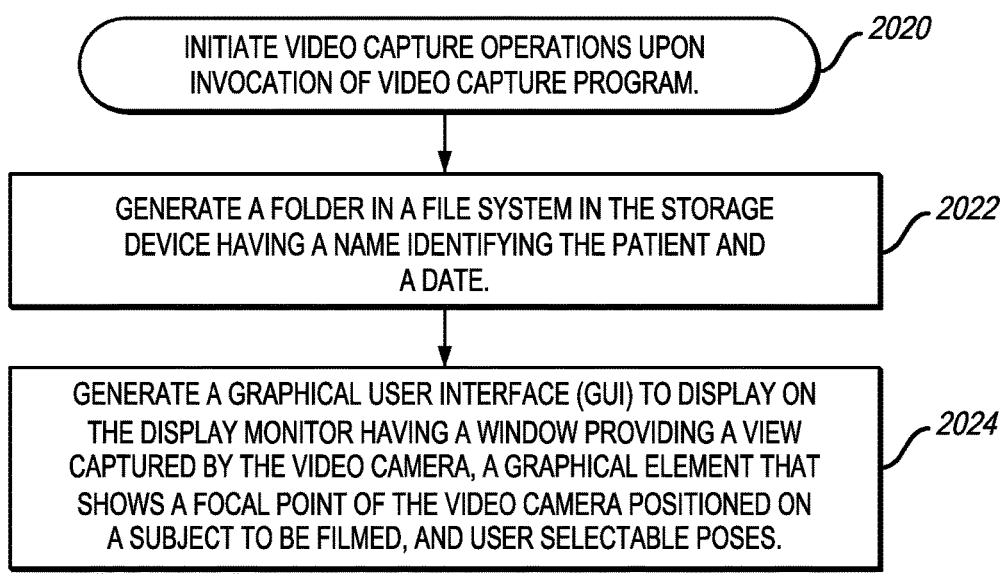
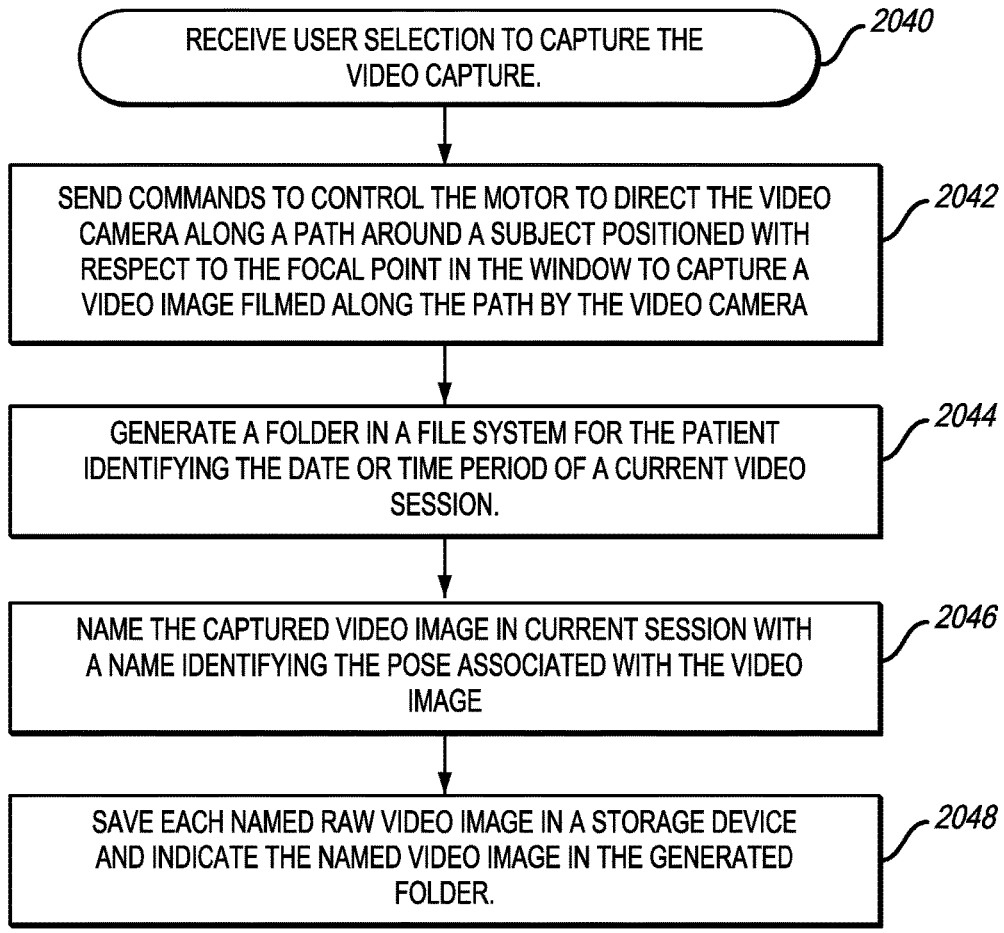

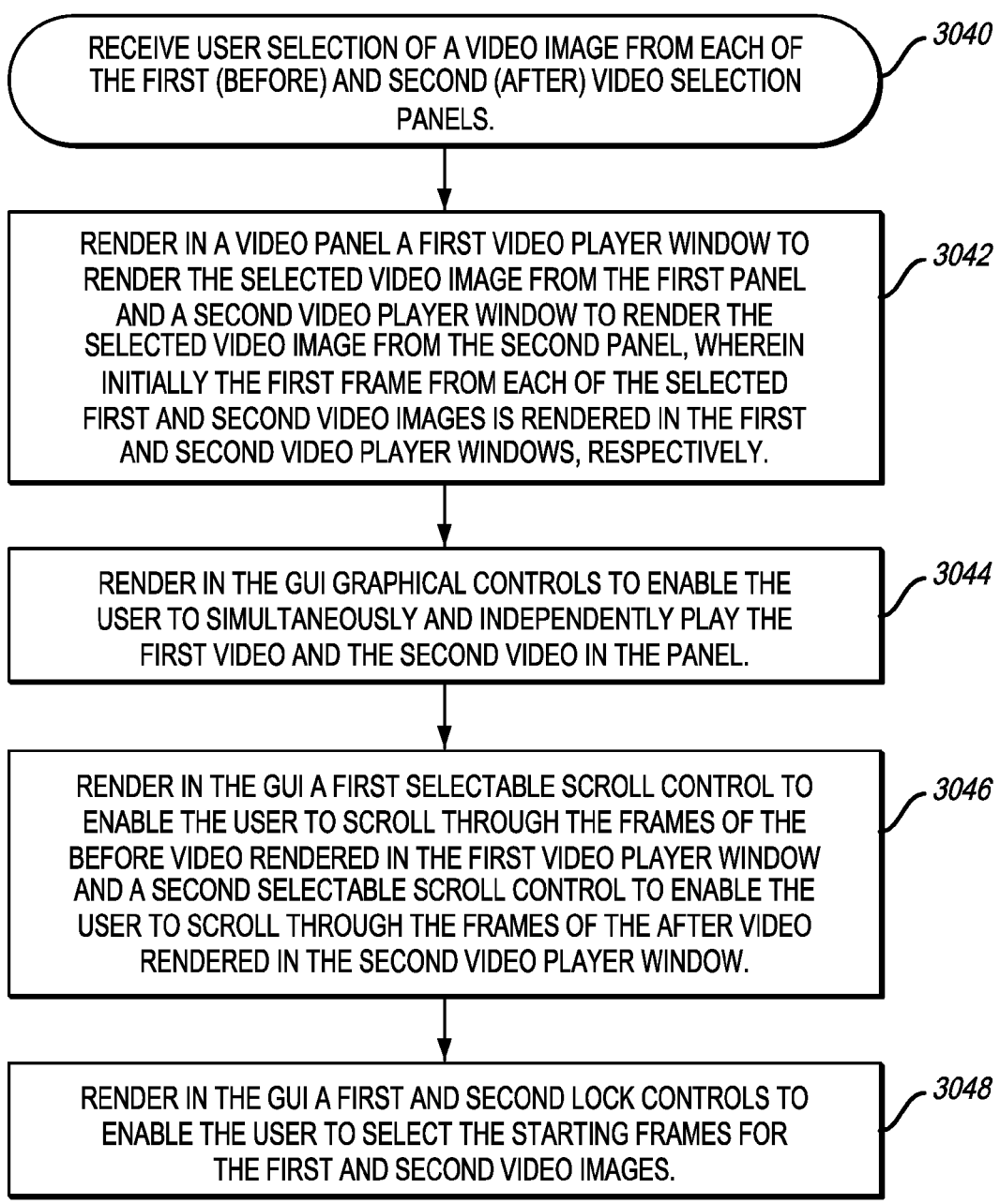

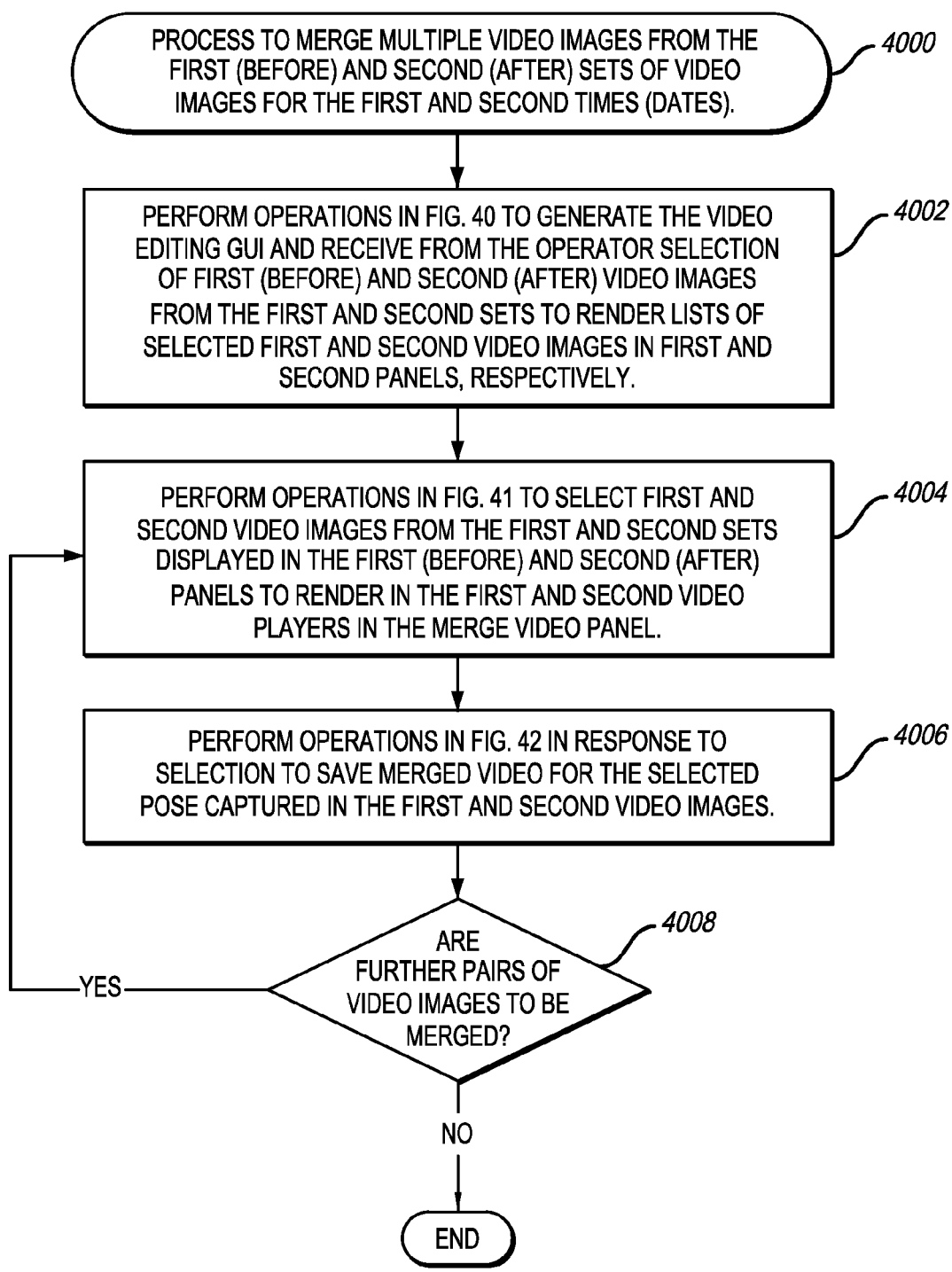

ROTATABLE IMAGING SYSTEM

CROSS REFERENCE TO RELATED APPLICATIONS

This application is a continuation-in-part of U.S. patent application Ser. No. 14/740,087, filed on Jun. 15, 2015, which is a continuation-in-part of U.S. patent application Ser. No. 14/559,827, filed on Dec. 3, 2014, issued as U.S. Pat. No. 9,060,125 on Jun. 16, 2015, which claims the benefit of U.S. Provisional Patent Application No. 61/911,402, filed on Dec. 3, 2013, and is a continuation-in-part of U.S. patent application Ser. No. 13/779,543, filed on Feb. 27, 2013, issued as U.S. Pat. No. 9,207,518 on Dec. 8, 2015, which claims the benefit of U.S. Provisional Patent Application No. 61/603,853, filed on Feb. 27, 2012, and U.S. Provisional Patent Application No. 61/667,108, filed on Jul. 2, 2012, the entireties of each and all of which are incorporated herein by reference.

FIELD OF THE INVENTION

The present invention relates to a 360° imaging system, and more particularly to a 360° imaging system with an alignment system.

BACKGROUND OF THE INVENTION

In the field of plastic surgery, it is often desirable to document a patient's appearance before and after surgery. Photography is the usual means of documentation. However, often a photograph from one angle or even several angles is not sufficient to show the true transformation. Accordingly, a need exists for a system that documents up to a full 360° view of a patient before and after surgery.

SUMMARY OF THE PREFERRED EMBODIMENTS

In accordance with a preferred embodiment of the present invention there is provided an imaging system that includes a rotating unit that includes an imaging camera, an alignment camera and at least a first monitor. The rotating unit is rotatable between a home position and a finish position about a rotation axis such that the imaging camera can capture a first scan. The alignment camera is directed generally downwardly and is configured to capture a first alignment image of a subject positioned generally co-axially with the rotation axis. The first alignment image is displayed on the first monitor.

In a preferred embodiment, the alignment markings include a stationary alignment marking and a movable alignment marking, and the rotating unit will not rotate from the home position to the finish position unless the stationary alignment marking is within a predetermined tolerance zone. Preferably, the stationary alignment marking is created using a differential map. In a preferred embodiment, the movable alignment marking that is a live image taken from the alignment camera. Preferably, at least one differential map is created to determine the location of the movable alignment marking in relation to the stationary alignment marking to produce a comparison percentage, and the comparison percentage is displayed on the alignment monitor on a meter.

In a preferred embodiment, the imaging system also includes a support assembly that includes a base and a vertically oriented support structure and a horizontal boom extending outwardly from the vertically oriented support structure. The rotating unit is positioned below the horizontal boom and is adapted to rotate with respect to the horizontal boom about the rotation axis. Preferably, the backdrop includes a curved backdrop portion and a hood portion.

In accordance with another aspect of the present invention, there is provided an imaging system that includes a rotating unit with an imaging camera. The rotating unit is rotatable about a rotation axis and includes a first portion and a second portion that are rotatable about the rotation axis. The first portion and the second portion each have a proximal end through which the rotation axis extends and a distal end that is positioned away from the rotation axis. The imaging camera is associated with the distal end of the first portion and a backdrop is associated with the distal end of the second portion. The first portion and the second portion are rotatable from a stowed position where the first portion and the second portion are in substantial vertical alignment and a home position where the distal ends of the first portion and the second portion are approximately 180° from one another with respect to the rotation axis. The first portion and the second portion are rotatable together between the home position and a finish position such that the imaging camera can capture a first scan of a subject positioned generally co-axially with the rotation axis.

In a preferred embodiment, the first portion and the second portion are separately rotatable about the rotation axis. Preferably, the first portion and the second portion at least partially overlap in a vertical direction when in the stowed position. In a preferred embodiment, the imaging system also includes a horizontal boom having a first end that is adapted to be secured to a wall or other vertically oriented support structure and a second end to which the rotating unit is rotatably attached. In the stowed position, the first portion and the second portion are in substantial vertical alignment with the horizontal boom. Preferably, the distal ends of the first portion and the second portion remain approximately 180° from one another when the first portion and the second portion rotate from the home position to the finish position.

In a preferred embodiment, the first monitor includes alignment markings thereon that include at least one of a head alignment circle, centering lines or a shoulder alignment line. Preferably, the rotating unit includes a first horizontal boom having a first end, a second end, and a middle section. A first arm depends downwardly from the first end of the first horizontal boom and the imaging camera is positioned on the first vertical arm. The screen depends downwardly from the second end of the first horizontal boom. In a preferred embodiment, the imaging system includes second horizontal boom. The first horizontal boom is positioned below the second horizontal boom and is adapted to rotate with respect to the second horizontal boom about the rotation axis.

In accordance with another preferred embodiment of the present invention there is provided a method that includes obtaining a rotating unit that includes an imaging camera, defines a rotation axis and is rotatable between a home position and a finish position, positioning an alignment camera that is directed generally downwardly generally co-axially with the rotation axis, positioning a subject below the alignment camera such that the subject can view a first alignment image captured by the alignment camera on a first monitor, aligning the subject, and rotating the rotating unit from the home position to the finish position and taking a first scan with the imaging camera at a first time to capture a first video image. In a preferred embodiment, the rotating unit includes a screen that rotates opposite the imaging camera.

In a preferred embodiment, in the home position the screen is positioned between the imaging camera and the first monitor and a first opening is defined in the screen. The first opening is aligned with the first monitor when the rotating unit is in the home position. Preferably, the imaging system includes a second monitor on which the first alignment image can be viewed, and the second monitor is positioned above the first monitor. The screen includes a second opening defined therein, and the second opening is aligned with the second monitor when the rotating unit is in the home position. In a preferred embodiment, the method further includes positioning the subject below the alignment camera such that the subject can view the first alignment image on the second monitor, aligning the subject, and rotating the rotating unit from the home position to the finish position and taking a second scan with the imaging camera.

In a preferred embodiment, the imaging system includes a third monitor on which the first alignment image can be viewed, and the third monitor is positioned above the first monitor. The screen includes a third opening defined therein, and the third opening is aligned with the third monitor when the rotating unit is in the home position. In a preferred embodiment, the method further includes positioning the subject below the alignment camera such that the subject can view the first alignment image on the third monitor, aligning the subject, and rotating the rotating unit from the home position to the finish position and taking a third scan with the imaging camera.

In a preferred embodiment, the method further includes positioning the subject below the alignment camera such that the subject can view a second alignment image captured by the alignment camera on the first monitor, aligning the subject, and rotating the rotating unit from the home position to the finish position and taking a second scan at a second time with the imaging camera to provide a second video image. Preferably, the method includes merging the first video image and the second video image to provide a merged video image that shows at least a portion of the first scan adjacent at least a portion of the second scan.

In accordance with another preferred embodiment of the present invention there is provided an imaging system that includes a rotating unit that includes a first horizontal beam that rotates about a rotation axis. The first horizontal beam has first and second opposite ends and includes an imaging camera depending downwardly from the first end and a screen depending downwardly from the second end such that it rotates opposite of the imaging camera. The imaging camera is rotatable about the rotation axis between a home position and a finish position. The imaging system also includes an alignment camera positioned below the first horizontal beam and directed generally downwardly. The alignment camera is generally co-axial with the rotation axis and is configured to capture a first alignment image of a subject positioned generally co-axially with the rotation axis/The imaging system also includes at least a first monitor on which the first alignment image is displayed. In the home position the screen is positioned between the imaging camera and the first monitor. A first opening is defined in the screen and the first opening is aligned with the first monitor when the rotating unit is in the home position. In a preferred embodiment, the imaging system further includes a second horizontal beam that includes first and second opposite ends.

The first end is adapted to be secured to a wall and wherein the first horizontal beam is rotatably connected to the second end.

In accordance with another preferred embodiment of the present invention there is provided a computer program product that includes a computer readable storage medium having program code executed to communicate with a video camera, a motor system that moves the video camera along a path, a display monitor, and a storage device, and to perform operations that includes generating a graphical user interface (GUI) to display on the display monitor providing a view captured by the video camera and a graphical element that shows a focal point of the video camera positioned on a subject to be filmed. In response to receiving user selection to capture a video image, sending commands to control the motor system to move the video camera along a path around a subject positioned with respect to the focal point in the video to capture a video image filmed along the path by the video camera, storing the captured video image in the storage device; and associating information identifying the subject filmed by the video camera with the stored video image. In a preferred embodiment, the operations further comprise rendering in the GUI a description of plurality of selectable poses for the subject being filmed, receiving user selection indicating one of the selectable poses captured in the video image, and associating information identifying the selected pose with the video image. Associating the information identifying the subject and the selected pose with the video image comprises generating a folder in a file system in the storage device having a name identifying the subject and a date the video image was captured, and indicating in the file system the video image as included in the folder and having a file name indicating the selected pose.

Preferably, the path includes at least one movement comprising rotating around the subject centered at the focal point for a predefined number of degrees of rotation; moving toward the subject, moving away from the subject, and moving vertically up or down with respect to the subject. In a preferred embodiment, the path rotates more than 360 degrees around the subject centered at the focal point. Preferably, the video image includes a first video image captured at a first time. Information on the first time is associated with the first video image and the operations further comprise, in response to receiving user selection to capture a second video image at a second time following the first time, sending commands to control the motor system to move the video camera along the path with respect to the subject positioned with respect to the focal point in the view to capture a second video image filmed along substantially the same path the video camera was moved when capturing the first image, storing the captured second video image in the storage device, and associating information identifying the subject filmed by the video camera with the second video image and the second time.

In a preferred embodiment, the operations further comprise for each of a plurality of different poses at which the subject is positioned, performing sending commands to control the motor system to move the video camera along the path with respect to the subject positioned with respect to the focal point in the view to capture a video image filmed along the path by the video camera for one of the poses, storing the captured video image for the pose in the storage device, and associating information identifying the subject filmed by the video camera, the pose and a time at which the pose was captured with the video image.

In accordance with another preferred embodiment of the present invention there is provided a computer program product comprising a computer readable storage medium having program code that when executed performs operations that include receiving selection of a first video image and a second video image that each include a sequence of a number of frames of a subject positioned with respect to a focal point while a video camera moved along a path of the subject, for each of a plurality of the frames in the first and second video images, forming a merged frame comprising content from a first frame in the first video image and a second frame in the second video image, and saving a merged video image having the merged frames, wherein the merged frames are ordered in the sequence of the frames from the first and second video images used to form each of the merged frames. In a preferred embodiment, the merging of the frames is performed in a sequential order of the frames in the first and second video images. Preferably, the video camera was controlled to move along substantially the same path when capturing the first and second video images, and the first and second video images capture the subject in a pose at different first and second times. In a preferred embodiment, the first video image captures a region of the subject's body before a medical procedure and the second video image captures same regions of the patient's body captured in the first video image after the medical procedure.

In a preferred embodiment, the merged video program has in sequence frames, each frame having relatively identical views of the subject from the first and second video images, and the merged video program when played shows the relatively identical views of the subject rotating simultaneously. Preferably, the operations further comprise determining a first starting frame and a second starting frame in the first and second video images, respectively, at which to start merging the frames from the first and second video images into the merged frames. A fixed number of frames starting from the first and second starting frames in the first and second video images, respectively, are sequentially processed to form the merged frames. The first and second starting frames are at different positions in the sequences of the frames in the first and second video images.

In a preferred embodiment, the determining the first starting frame and the second starting frame comprises rendering in a graphical user interface (GUI) at least one selectable control to enable a user to scroll through the frames of the first and second video images to select at least one of the first and second starting frames. The first and second starting frames each comprise either a first frame in the sequence of frames or the user selected frame following the first frame in the sequence. Preferably, the operations further comprise rendering in a panel of a graphical user interface (GUI) a first video player window to render the first video image and a second video player window to render the second video image, and rendering in the GUI a graphical control to enable the user to simultaneously and independently control the play of the first video and the second video in the panel.

In a preferred embodiment, the operations further comprise rendering in the GUI at least one selectable scroll control to enable the user to independently scroll through the frames of the first and second videos rendered simultaneously in the panel to enable the user to select a first starting frame and a second starting frame in the first and second videos, respectively, at which to start merging the frames into the merged frames. A fixed number of frames starting from the user selected first and second starting frames in the first and second videos, respectively, are sequentially processed to form the merged frames. Preferably, the first video image comprises a first of a plurality of video images selected from a first set of video images and the second video image comprises a first of a plurality of videos selected from a second set of video images. Each set of video images was taken at different first and second times and each of the video images in the first and second sets comprise video images taken with the subject at different poses. The operation of forming a merged frame for each of a plurality of the frames in the first and second video images is performed for each pair of video images in the first and second sets of video images that are for the same pose.

In a preferred embodiment, the first and second video images each include frames having a color chart. The forming the merge frame further comprises, for each of the first and second videos, performing a color calibration of all the frames based on the color chart included in the frames resulting in color corrected first and second vides, and, for each of the color corrected first and second videos, cropping the content in the frame to remove the color chart from the frames. The merged frames comprise cropped frames from the color corrected first and second videos.

The present invention captures 360° video of a patient's face or body in high definition, allowing for a true, dynamic rendering of the patient's features. Before-and-after videos are created and positioned automatically to provide a complete, easy-to-see analysis of procedure results. The images show how the patient's features move in real-time, adding the dimension of depth and a true rendering of shape.

The invention includes an articulated swiveling horizontal boom adapted to carry on one of its extremities a device, such as a video camera, still camera, phone or tablet video recording device or other imaging device, which can be moved 360°. On the opposite end of the horizontal boom is mounted a backdrop that will rotate in synchrony about the vertical axis with the camera. The horizontal boom swivels about a vertical axis with the camera at one end and the background attached to the opposite end. The subject to be filmed is placed in a position that is generally co-axial with the vertical axis and is fixed in position. The camera travels 360° around the subject obtaining video imaging of the subject.

The "camera" end of the horizontal boom has a vertical arm or boom that extends downwardly and has the camera mounted thereon. The vertical arm or boom can be telescopic allowing lengthening or shortening to adjust the camera height. The "backdrop" end of the horizontal boom also includes a vertical arm or boom. This vertical arm or boom has the backdrop mounted thereon and travels opposite the video camera as the horizontal boom rotates. A lighting system is mounted on the "camera" end of the horizontal boom and on the vertical arm or boom that holds the imaging device. The lighting system provides downward lighting and front lighting of the subject that remains consistent as the camera rotates around the subject. A third light can be located toward the opposite end of the horizontal boom close to the vertical axis. This light source illuminates the background, thus preventing shadowing created from the two other light sources. All of these light fixtures are adjustable in location and intensity depending on the need to illustrate features of the object being imaged. Motorized movement control may be provided to rotate the imaging system and background around the subject, or to lower or raise each vertical arm or boom, or to articulate the vertical arms or booms upwards or downwards.

The imaging system can be oriented to capture images in either portrait or landscape orientation depending on the needs of the project. Preferably, when imaging the human body the camera is positioned to obtain portrait images that are vertically oriented.

Imaging of the human body, face, head and neck preferably includes the use of video imaging with a high-resolution system. In an exemplary embodiment, for the purposes of cosmetic surgery planning for the head and neck, the camera obtains two video clips of the subject with the first 360° scan being taken when the subject is in repose and the second 360° scan would be taken with the patient smiling. The subject can be seated on an adjustable stool, chair or other seat allowing the raising and lowering of the subject to the appropriate level of the camera and/or through adjustment of the camera. The camera can be moved up and down to center or align the patient (or the appropriate body part(s)) vertically. Adjustment can be manual or motorized (e.g., an operator can center the camera or patient from his/her computer monitor using the computer).

In a preferred embodiment, the imaging system includes an automated process for capturing, editing, storing, retrieving and compositing orbital shot footage. The system includes a motion controlled armature (or series of booms) which rotates the camera, lights and backdrop around the patient at a repeatable rate. The imaging device can be programmed (or manually moved) to stop at any position within the orbit, allowing the camera to pause at one or more points through the orbit. In a preferred embodiment, lighting can be programmed to change intensity, color temperature or source/direction. In an exemplary embodiment, the operator initializes the system using a touchscreen and enters patient metadata (e.g., name, surgical procedure, etc.). The patient is positioned, either seated or standing, under the axis of rotation, with the assistance of an eye safe laser (or other positioning device). In use, the operator reaches overhead and lowers the camera and backdrop into a fixed position for the scan. The camera elevation can be set over a wide range (e.g., 6" to 80") to scan any horizontal band of the patient's body.

In accordance with an aspect of the present invention there is provided a 360 degree camera imaging system comprising a first horizontal boom having a first end, a second end, and a middle section; a second horizontal boom having a first end and a second end; a first vertical arm having a first end and a second end; a second vertical arm having a first end and a second end; and a mounting bracket. The first horizontal boom is connected to the first end of the second horizontal boom by a first rotatable pivot proximate the middle section of the first horizontal boom, and the second end of the second horizontal boom is connected to the mounting bracket. The first end of the first vertical arm is affixed to the first end of the first horizontal boom, and the first end of the second vertical arm is affixed to the second end of the first horizontal boom. A camera is mounted to the first vertical arm, and a backdrop is mounted to the second vertical arm. In a preferred embodiment, the second end of the second horizontal boom is connected to the mounting bracket by a second rotatable pivot. Preferably, the backdrop is mounted to the second vertical arm by way of a third rotatable pivot. Preferably, a light is mounted on the first vertical arm. Preferably, a second light mounted on the second vertical arm, proximate the first end of the second vertical arm. Preferably, the camera is a video camera. Preferably the 360 degree camera imaging system further comprises a second camera. Preferably, the second camera is a still camera. Preferably, an electric motor is affixed to the second horizontal boom. Preferably, the electric motor is affixed proximate the first rotatable pivot. Preferably, the 360 degree camera imaging system further comprises a color scale. Preferably, the 360 degree camera imaging system further comprises a light emitting diode centering light.

In accordance with another aspect of the present invention there is provided a 360 degree camera imaging system comprising a horizontal boom having a first end, a second end, and a middle section; a first vertical arm having a first end and a second end; a second vertical arm having a first end and a second end; and a rotatable pivot proximate the middle section of the horizontal boom. The first end of the first vertical arm is affixed to the first end of the first horizontal boom, and the first end of the second vertical arm is affixed to the second end of the first horizontal boom. A camera is mounted to the first vertical arm, and a backdrop is mounted to the second vertical arm.

In accordance with another aspect of the present invention there is provided a method of using a 360 degree camera system to capture a set of before and after images of a subject, the method comprising the steps of (1) positioning the subject in between a camera and a backdrop at a first position, (2) passing the camera in a generally circular path around the subject while using the camera to capture at least five images of at least a portion of the subject, so as to capture a first image set, (3) positioning the subject a second time in between the camera and the backdrop at approximately the first position, (4) passing the camera in a generally circular path around the subject while using the camera to capture at least five images of at least a portion of the subject, so as to capture a second image set, and (5) comparing the first image set to the second image set. In a preferred embodiment, the method further comprises the use of a second camera that is a still camera, which captures at least five images while the first image set is being captured and at least five images while the second image set is being captured. Preferably, the first light is located generally in front of the subject, and a second light is located generally behind the subject. In a preferred embodiment, the rate of camera movement during capture of the first image set as compared to camera movement during capture of the second image set is substantially the same. Preferably, a subset of images from the first image set are selected. Preferably, a subset of images from the second image set are selected. In a preferred embodiment, the camera passes through at least about 360 degrees while capturing the first image set and through at least about 360 degrees while capturing the second image set. Preferably, a first side-by-side image of the subject and at least a second side-by-side image of the subject are produced. Preferably, the first side-by-side image of the subject includes an image from the first image set and an image from the second image set, and the second side-by-side image of the subject includes an image from the first image set and an image from the second image set.

A preferred embodiment of the present invention comprises a computerized system for combining before and after videos from a 360 degree camera imaging system, the instructions of one or more software modules being stored on a nonvolatile computer readable medium, the system comprising: a first software module configured to receive selective input from a user regarding a first image set; a second software module configured to receive selective input from a user regarding a second image set that has a greater number of images than the first image set; and a third software module configured to crop images from the second image set, such that the number of images in the second image set is about the same as the number of images in the first image set. The third software module is further configured to combine the first image set with the second image set to produce a third image set comprising side-by-side images of the first image set and the second image set. Preferably, the first and second image sets each have a starting frame, and the third software module is further configured to crop images from the second image set by setting the starting frame of the first image set to zero, and by setting the starting frame of the second image set to one half the difference in the number of images of the second image set and the first image set. Preferably the computerized system further comprises a fourth software module configured to combine the third image set, sequentially, with a fourth image set. Preferably, the fourth image set is a side-by-side image set produced by the third software module.

Another preferred embodiment of the present invention comprises a method for combining before and after videos from a 360 degree camera by a user accessing software instructions stored on a nonvolatile computer readable medium, which software instructions are executed by at least one processor, the method comprising the steps of: receiving selective input from a user regarding a first image set; receiving selective input from a user regarding a second image set that has a greater number of images than the first image set; cropping images from the second image set, such that the number of images in the second image set is about the same as the number of images in the first image set; and combining the first image set with the second image set to produce a third image set comprising side-by-side images of the first image set and the second image set. Preferably, the first and second image sets each have a starting frame, and images are cropped from the second image set by setting the starting frame of the first image set to zero, and by setting the starting frame of the second image set to one half the difference in the number of images of the second image set and the first image set. Preferably, the computer implemented method further comprises the step of combining the third image set, sequentially, with a fourth image set. Preferably, the fourth image set is a side-by-side image set comprising two image sets that each comprise about the same number of images.

Another preferred embodiment of the present invention comprises a computer implemented method of using a 360 degree camera system to capture a set of before and after images of a subject, the method comprising the steps of: positioning the subject in between a camera and a backdrop at a first position; passing the camera in a generally circular path around the subject while using the camera to capture at least two images of at least a portion of the subject, so as to capture first image set; positioning the subject a second time in between the camera and the backdrop at approximately the first position; passing the camera in a generally circular path around the subject while using the camera to capture more than two images of at least a portion of the subject, so as to capture a second image set; cropping images from the second image set, such that the number of images in the second image set is about the same as the number of images in the first image set; and combining the first image set with the second image set to produce a third image set comprising side-by-side images of the first image set and the second image set. Preferably, the first and second image sets each have a starting frame, and wherein images are cropped from the second image set by setting the starting frame of the first image set to zero, and by setting the starting frame of the second image set to one half the difference in the number of images of the second image set and the first image set. Preferably, the computer implemented method further comprises the step of combining the third image set, sequentially, with a fourth image set. Preferably, the fourth image set is a side-by-side image set comprising two image sets that each comprise about the same number of images. Preferably, the computer implemented method further comprises a second camera that is a still camera. Preferably, a first light is located generally in front of the subject, and a second light is located generally behind the subject. Preferably, the rate of camera movement during capture of the first image set as compared to camera movement during capture of the second image set is substantially the same. Preferably, the camera passes through at least about 360 degrees while capturing the first image set and through at least about 360 degrees while capturing the second image set.

The invention, together with additional features and advantages thereof, may be best understood by reference to the following description.

BRIEF DESCRIPTION OF THE DRAWINGS

FIGS. 36-38 illustrate embodiments of operations to capture video images from an imaging system;

FIGS. 39-42 illustrate embodiments of operations to merge captured video images into a merged video image;

Like numerals refer to like parts throughout the several views of the drawings.

DETAILED DESCRIPTION OF THE PREFERRED EMBODIMENTS

Figure 1:
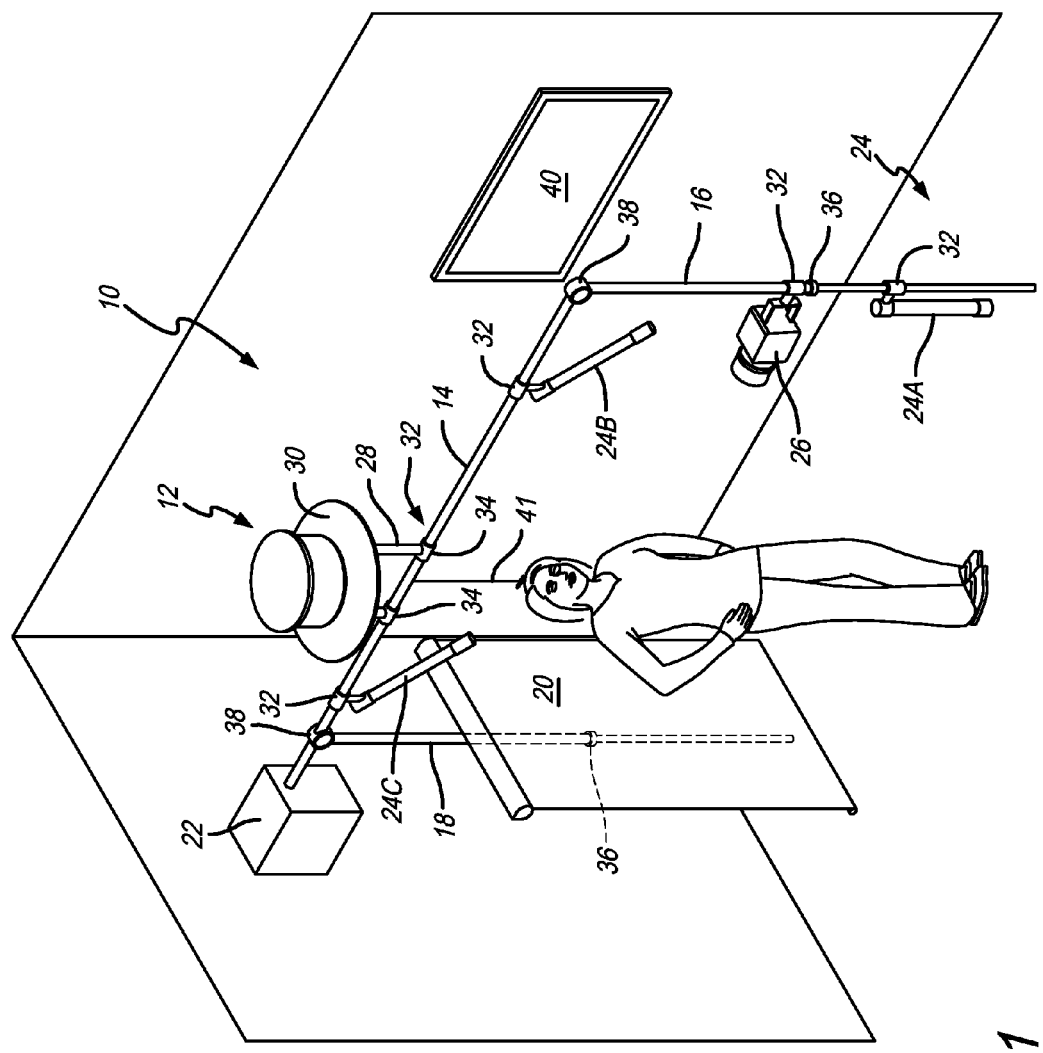
FIG. 1 is a perspective view of a 360° imaging system in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments.

Reference in this specification to "one embodiment" or "an embodiment" means that a particular feature, structure, or characteristic described in connection with the embodiment is included in at least one embodiment of the-disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "upper," "lower," "side," "short," "long," "up," "down," and "below" used herein are merely for ease of description and refer to the orientation of the components as shown in the figures. It should be understood that any orientation of the components described herein is within the scope of the present invention.

Referring now to the drawings, which are for purposes of illustrating the present invention and not for purposes of limiting the same, FIG. 1 shows a preferred embodiment of a 360° imaging system 10 in accordance with a preferred embodiment of the present invention. The imaging system 10 can be used to take 360° pictures or videos of a person, object or scene positioned about a substantially vertical axis. The system 10 is preferably suspended from the ceiling and includes an imaging device that is pointed toward the object and is rotatable about the substantially vertical axis. In the exemplary embodiment described herein, the system 10 is used for imaging plastic surgery patients (e.g., to show before and after results). However, this is not a limitation on the present invention and it will be understood that the system 10 can be used for imaging any desired object.

Figure 2:
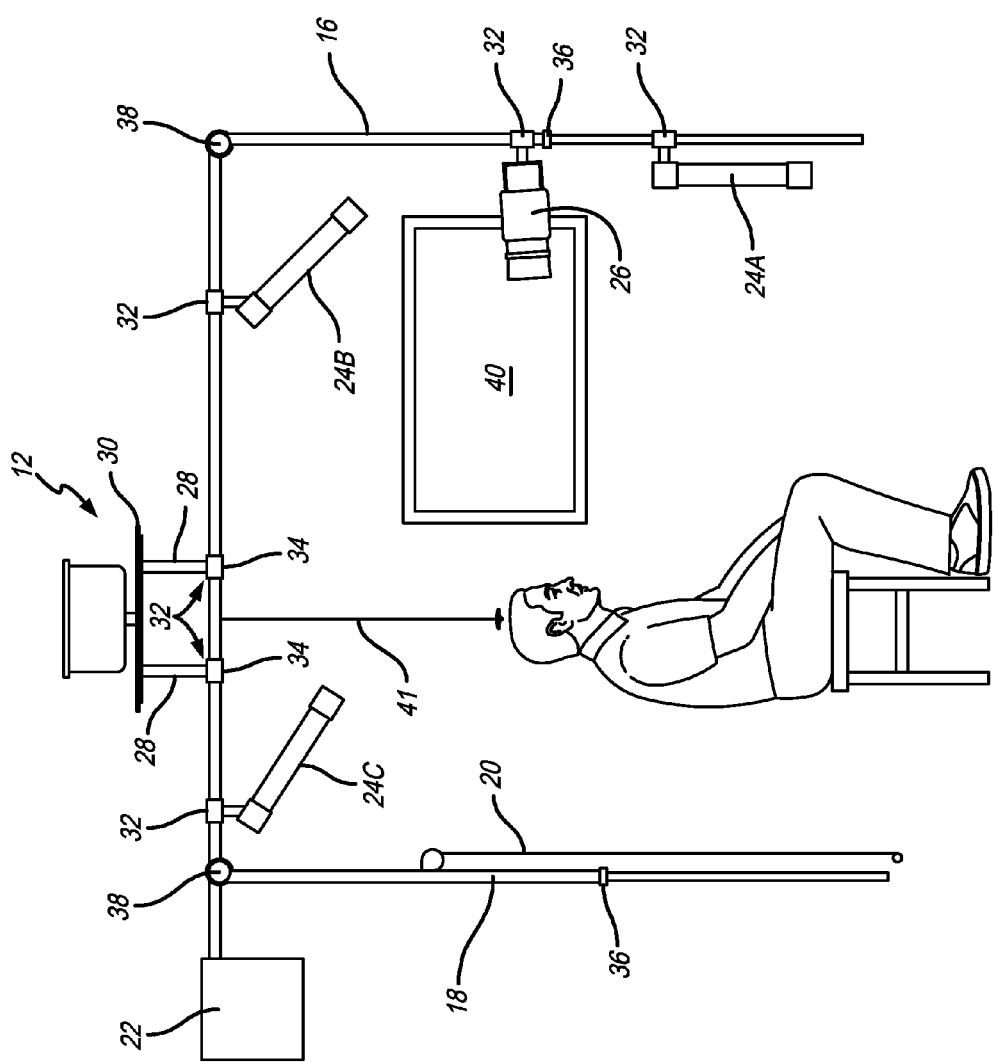
FIG. 2 is a side elevational view of the 360° imaging system of FIG. 1.
Figure 3:
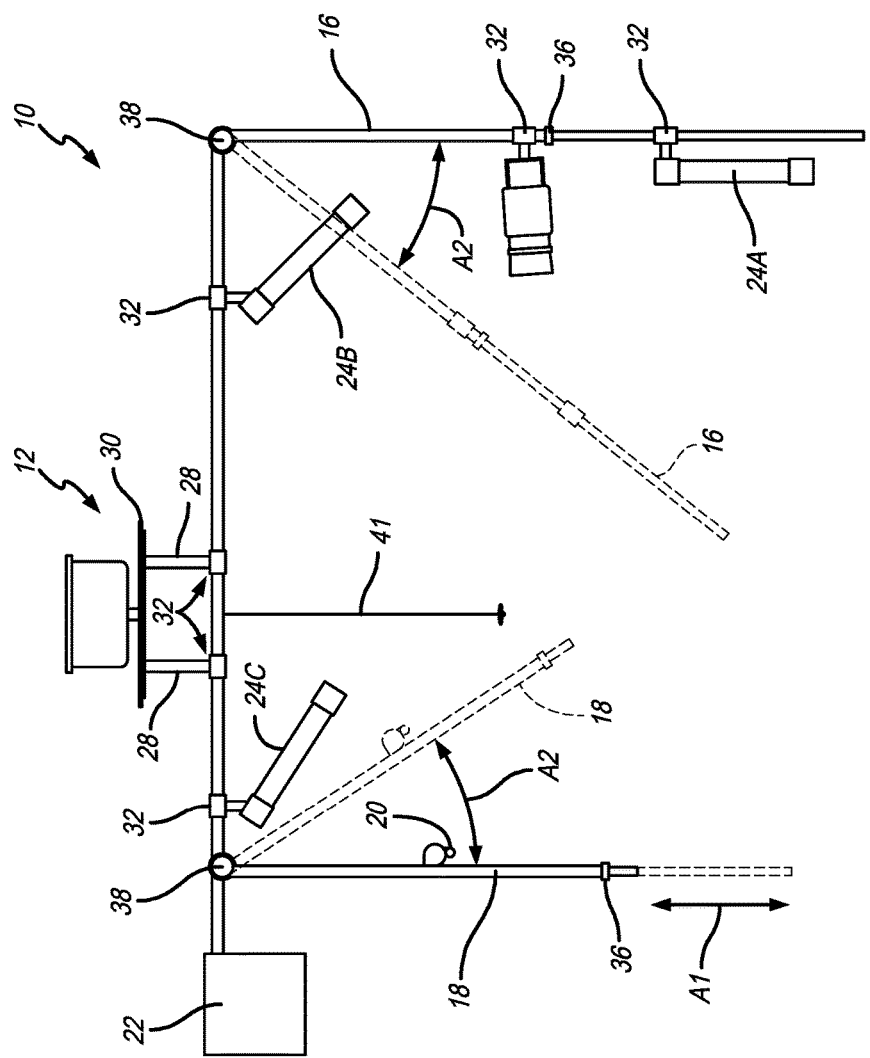
FIG. 3 is a side elevational view of the 360° imaging system of FIG. 1 showing the pivotal adjustability of the horizontal arms.

As is shown in FIGS. 1-3, in a preferred embodiment, the imaging system 10 includes a rotation device 12 having a horizontally oriented boom 14 depending therefrom, first and second vertically oriented booms or arms 16 and 18, a backdrop 20, a counterweight 22, a lighting system 24 and an image capture device 26. In a preferred embodiment, the rotation device 12 is attached to or built into the ceiling of a room and includes a shaft or shafts 28 extending downwardly therefrom. As is best shown in FIG. 2, in a preferred embodiment, the rotation device 12 includes a rotatable plate 30 to which the shafts 28 are attached. The opposite ends of the shafts are associated with the horizontal boom 14. The shafts 28 can be attached directly to the horizontal boom 14 or the shafts can include a slidable adjustment member 32 through which the horizontal boom 14 extends. It will be appreciated by those skilled in the art that any type of adjustment member that allows the horizontal boom 14 to be adjusted in a horizontal or axial direction is within the scope of the present invention. For example, the slidable adjustment member 32 can be a tube 34 through which the horizontal boom 14 extends and that includes a set screw (not shown) that holds the horizontal boom 14 in place.

As shown in FIGS. 2-3, in a preferred embodiment, first and second vertical arms 16 and 18 extend downwardly from horizontal boom 14. First vertical arm 16 includes image capture device 26 secured thereon. In a preferred embodiment, the height of image capture device 26 is adjustable. This can be done via a slidable adjustment member 32, as described above or by another known method. In another embodiment, the first vertical arm 16 itself can be adjustable, for example by a telescopic adjustment member 36 or by providing for movement vertically of the entire first vertical arm 16. In a preferred embodiment, second vertical arm 18 includes backdrop 20 secured thereon. The height of backdrop 20 or second vertical arm 18 can also be adjustable. See, e.g., telescopic adjustment member 36 and arrow A1 in FIG. 3. Furthermore, backdrop 20 can be raised or lowered, as is known in the art. In a preferred embodiment, the first and second vertical arms 16 and 18 are also pivotally adjustable as shown by arrows A2 in FIG. 3. As will be appreciated by those skilled in the art, pivotal adjustment can be provided by pivotal adjustment members 38 or the like.

As is shown in FIGS. 1-3, lighting system 24 includes a plurality of lights 24a, 24b and 24c. Any number of lights is within the scope of the present invention, and will depend on the needs of the particular project. In an exemplary embodiment, the light system 24 includes a first light 24a disposed on first vertical arm 16 for front lighting of the subject, a second light 24b for downward front lighting and a third light 24c for lighting the backdrop 20. In a preferred embodiment each of the lights 24 are adjustable, such as by a slidable adjustment member 32, as described above. In another embodiment, the lights 24 can be clipped onto the horizontal boom 14 or first and/or second vertical arms 16 and 18.

In a preferred embodiment, horizontal boom 14 includes counterweight 22 at or near the end thereof that is opposite the end that includes the image capture device 26. Counterweight 22 helps balance the system. The counterweight 22 can also be adjustable or movable to account for the weight of image capture device 26, lights 24, backdrop 20 and other components. Wires for carrying electricity, video signals, etc. are not shown in the drawings. However, those of ordinary skill in the art will understand the need for wires or conductors, etc. for powering the image capture device 26, lights 24, etc. It is also within the scope of the invention that the video and/or audio signals be sent wirelessly.

As shown in FIG. 1, in a preferred embodiment, the system 10 includes a monitor 40 that displays the image being captured by the image capture device 26. The monitor 40 can also be used to play back the captured image(s). The image capture device 26 and monitor are in electrical communication via wires or wirelessly.

As shown in FIGS. 1-3, in a preferred embodiment, the imaging system 10 includes a plumb line 41 that extends downwardly from the horizontal boom 14 or the rotation device 12 and that is positioned substantially co-axially with the vertical axis defined by the rotation of the horizontal boom 14. In another embodiment, the plumb line can be omitted. In use, the subject to be filmed is placed in a position that is generally co-axial with the plumb line 41 and the vertical axis and is fixed in position. As shown in FIGS. 1 and 2, the subject can be seated or standing, as desired. The horizontal boom 14 is then rotated about the vertical axis with the image capture device 26 at one end and the background 20 attached to the opposite end. Preferably, the image capture device 26 travels 360° around the subject obtaining video imaging of the subject. In this configuration, the subject is always positioned between the image capture device 26 and the back drop 20. The counterweight 22 is positioned such that it helps maintain balance of the system so that the image capturing device 26 moves in a 360° arc in as close to a perfect circle as possible. In other words, the counterweight 22 helps prevent the image capturing device from moving up and down or swinging left to right, as it moves in a circle and captures the desired image.

Figure 4:
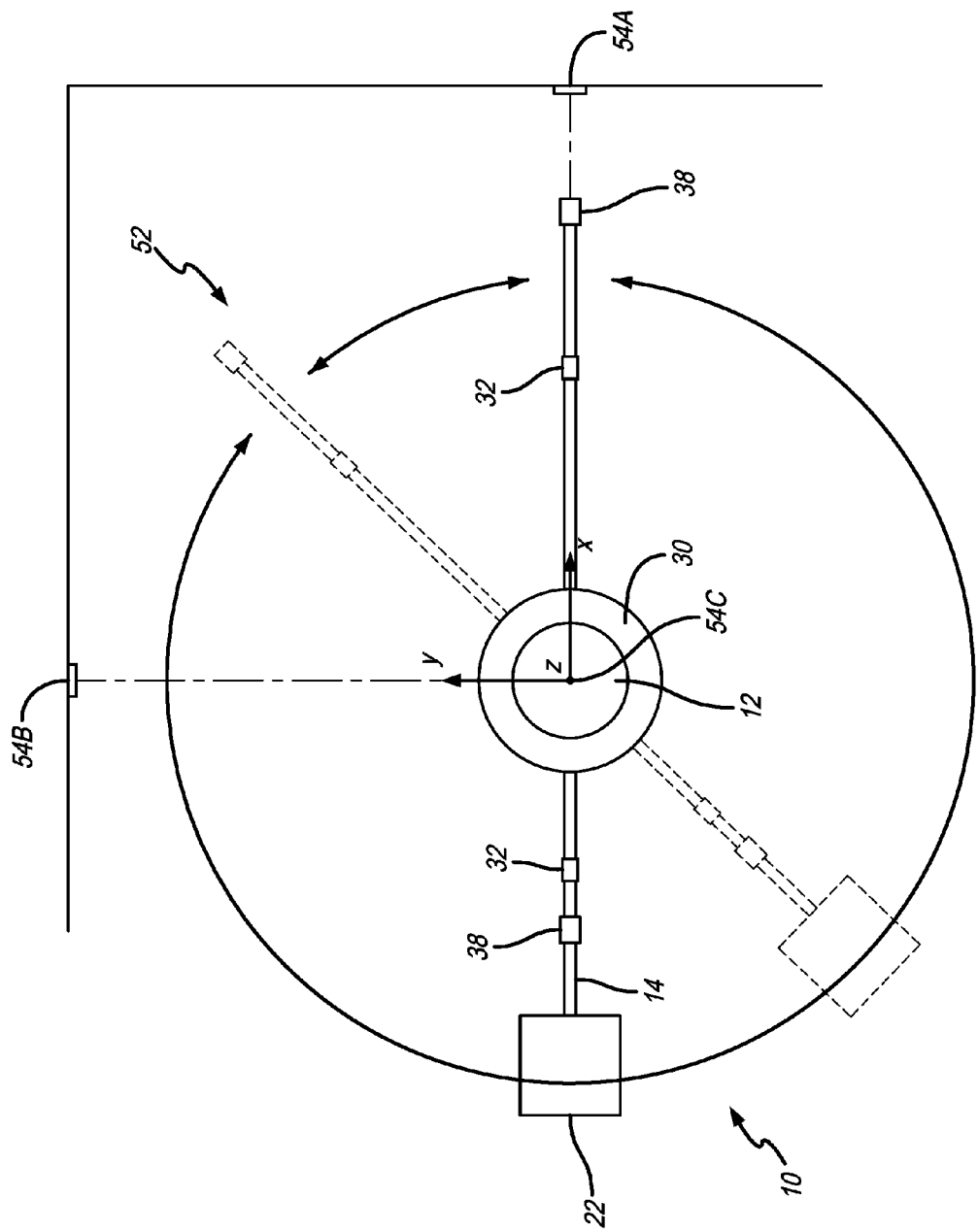
FIG. 4 is top plan view of the imaging system of FIG. 1 together with a centering system in accordance with an embodiment of the invention.
Figure 5:
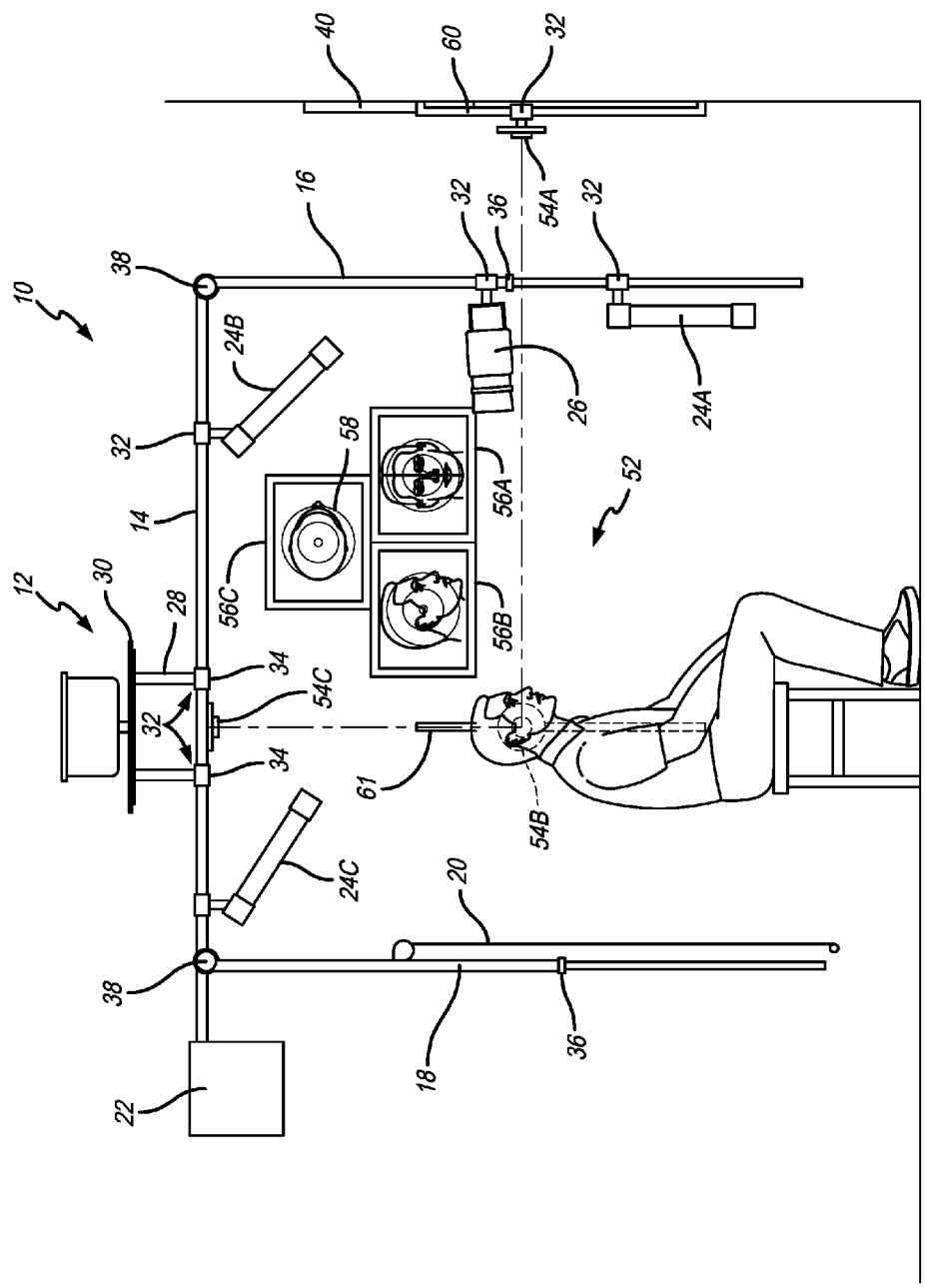
FIG. 5 is a side elevational view of the 360° imaging system of FIG. 1 together with the centering system of FIG. 4.

FIGS. 4-5 shows the imaging system 10 together with a centering system 52. In a preferred embodiment, centering system 52 includes three cameras or image capturing devices 54a, 54b and 54c positioned such that they are directed toward the point where the object to be imaged is optimally centered. These cameras are positioned to capture the front view (x-axis camera 54a), side or lateral view (y-axis camera 54b) and top view (z-axis camera 54c). In a preferred embodiment, the images from these cameras 54a-54c are communicated to one or more monitors 56a, 56b and 56c where the user of the system 52 can position the object to be filmed as desired. It will be understood that the images can be positioned on a single monitor or on separate monitors. In another embodiment, the images can be shown on monitor 40.

In a preferred embodiment, the three monitors 56a-56c are positioned on the wall and each include circles or markers 58 thereon that represent the optimal centered position. In use, using an example where the patient's head is being imaged, after the patient is seated, the surgeon can tell the patient to move their head, left, right, back, forth, etc. until their head is positioned as desired by the surgeon. This arrangement helps with repeatability between the before and after images.

In a preferred embodiment, cameras 54a-54c are movable. For example, x-axis camera 54a and y-axis camera 54b can be moved vertically depending on what portion of a patient is to be imaged. As shown in FIG. 5, the x-axis camera 54a and y-axis camera 54b can be mounted on an arm 61 and include a slidable adjustment member 32. It should be understood that the x-axis camera 54a and y-axis camera 54b are usually positioned at the same height vertically. Therefore, in use, the z-axis camera 54c aids in positioning the patient along the center axis, and the x-axis camera 54a and y-axis camera 54b aid the user in finding the desired horizontal level to be imaged. It will be appreciated by those skilled in the art that cameras 54a-54b are independent of camera 26 and are preferably only used to center the patient. Camera 26 is used to image the patient as desired. The type of centering system used is not a limitation on the present invention.

Figure 6:
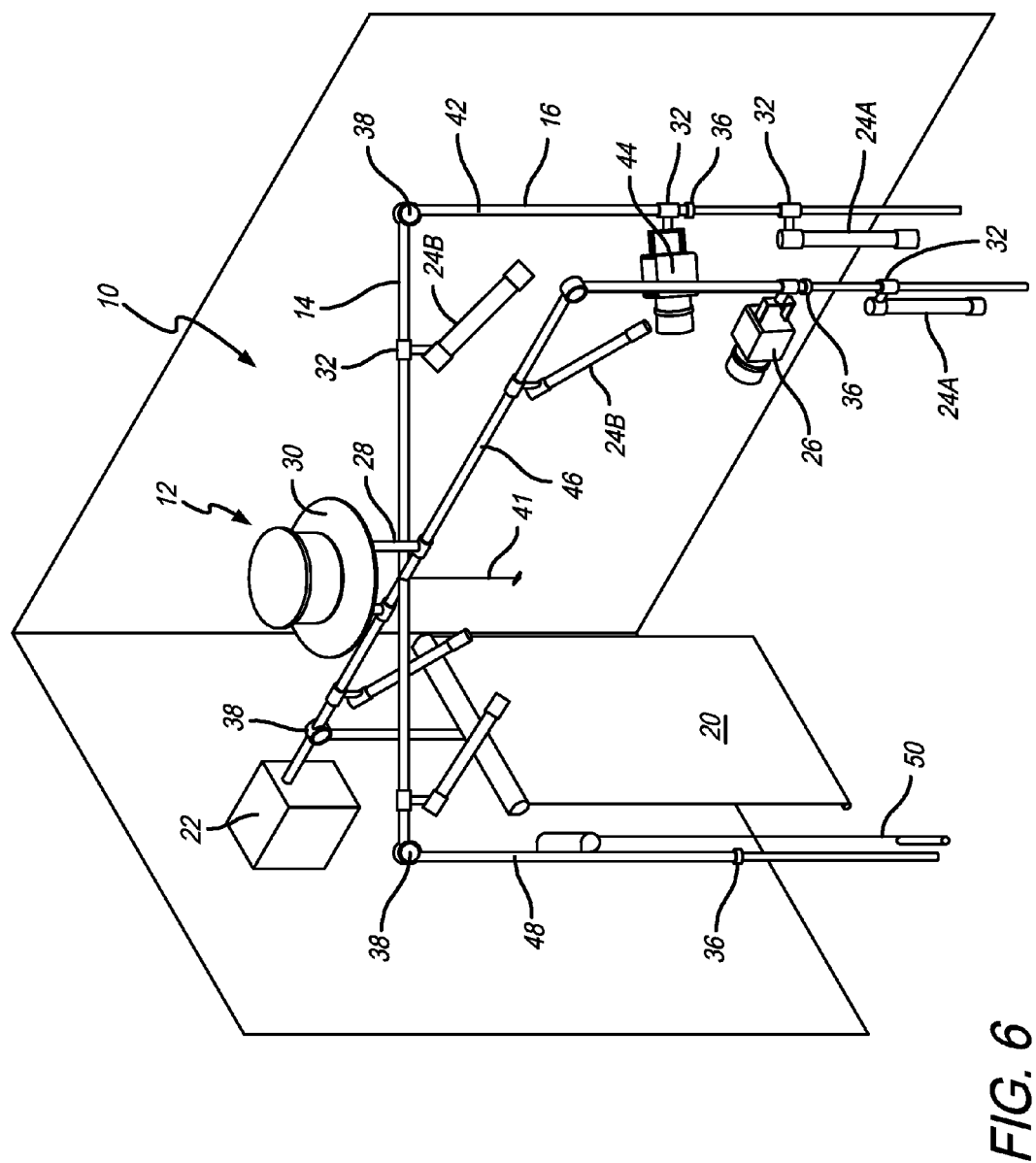
FIG. 6 is a perspective view of a 360° imaging system in accordance with another preferred embodiment of the present invention.

It will be understood that the system 10 can include multiple image capture devices 26. In one embodiment, the system 10 can include multiple image capture devices 26 on the first vertical arm 16, thereby allowing a larger vertical image capture area. In another embodiment, as shown in FIG. 6, the system 10 can include a third vertical arm 42 that includes a second image capture device 44. As shown in FIG. 6, in this embodiment, the system 10 can include a second horizontal boom 46, fourth vertical arm 48 and second backdrop 50. Any number of image capture devices, backdrops and associated booms or arms is within the scope of the present invention.

When used in the plastic surgery system the system 10 can be used for preoperative evaluation of the face, the body or extremities to assess the aging process or deformity. In an exemplary use, as shown in FIG. 2, the patient is seated as desired along the center axis, either by using the plumb line 41, centering system 52 or other centering methodology. The image capturing device 26 is then rotated 360° about the patient and the images are taken. In a preferred embodiment, the image capturing device 26 is rotated by hand. In other words, the user pushes or pulls the image capturing device 26 via the horizontal boom 14, first vertical arm 16 or other part of the system in a controlled manner around the patient. For example, the user focuses the camera 26, sets the desired exposure and then pushes the horizontal boom 14 and, because the system is counterbalanced via weight 22, it travels around the patient. In other embodiments, the rotation device 12 can be motorized and controlled remotely, by a switch, by computer or the like.

In a preferred embodiment, the image capture device 26 is a video camera. In an exemplary embodiment, the camera is a SONY® blu ray quality video camera that captures at least thirty frames per second as it passes around the patient. With this set up, the user can take any frame desired to make a photograph that can be used in patient evaluation, before and after pictures, etc.

The system 10 can be used so that the before and after images are standardized or taken under exactly the same conditions. In a preferred embodiment, the before and after images are taken using the same system 10, in the same location, with the patient positioned along the center axis, with approximately the same focal length from the patient and in a relatively dark room. Therefore, because the lighting system 24 travels with the image capturing device 26 the before and after images are relatively consistent. In an exemplary embodiment, after image capture pre and post-op, the user now has before and after dynamic three dimensional images and can also choose to select specific two dimensional images (or pictures) as desired.

Furthermore, as will appreciated by those skilled in the art, in plastic surgery the standard set of pictures of a patient is six different views. By using an image capture device 26 that captures thirty frames per second, even if the patient blinks or twitches or the like, with all of the separate images, a user will be able to find six separate images from the before and after image capturing sessions that help make an adequate comparison. This can be useful for showing to the patients, for marketing purposes or for a publication or paper authored by the plastic surgeon.

Continuing with an exemplary use in plastic surgery, the captured images can be used for patient evaluation both before and after surgery. For example, the images can be used with a prospective patient to point out areas that could use some work. In this scenario, after an image is taken, the plastic surgeon sits down with the patient and reviews the video clip rotating the patient's head, chest, abdomen or other body part in space, evaluating fat content, skin laxity, wrinkles. In an exemplary post-procedure use, for example after facial fat injections, the surgeon can look at the before and after head images next to each other and rotate them and look at an oblique view of the cheek to see if the results are satisfactory of if more fat needs to be injected.

The system 10 can also be used in the operating room when the patient is under general anesthesia so that the captured image(s) are free of blinking, movement, etc. The system 10 can also be used in the assessing of motor nerve function and facial nerve function and/or nerve function anywhere on the body by using the dynamic three-dimensional image.

In another embodiment of the invention, the imaging system 10 can be used in conjunction with placing the 3D markers on the skin or adjacent thereto. 3D markers for motion capture and the like are known. Accordingly, a description thereof will be omitted.

Figure 7:
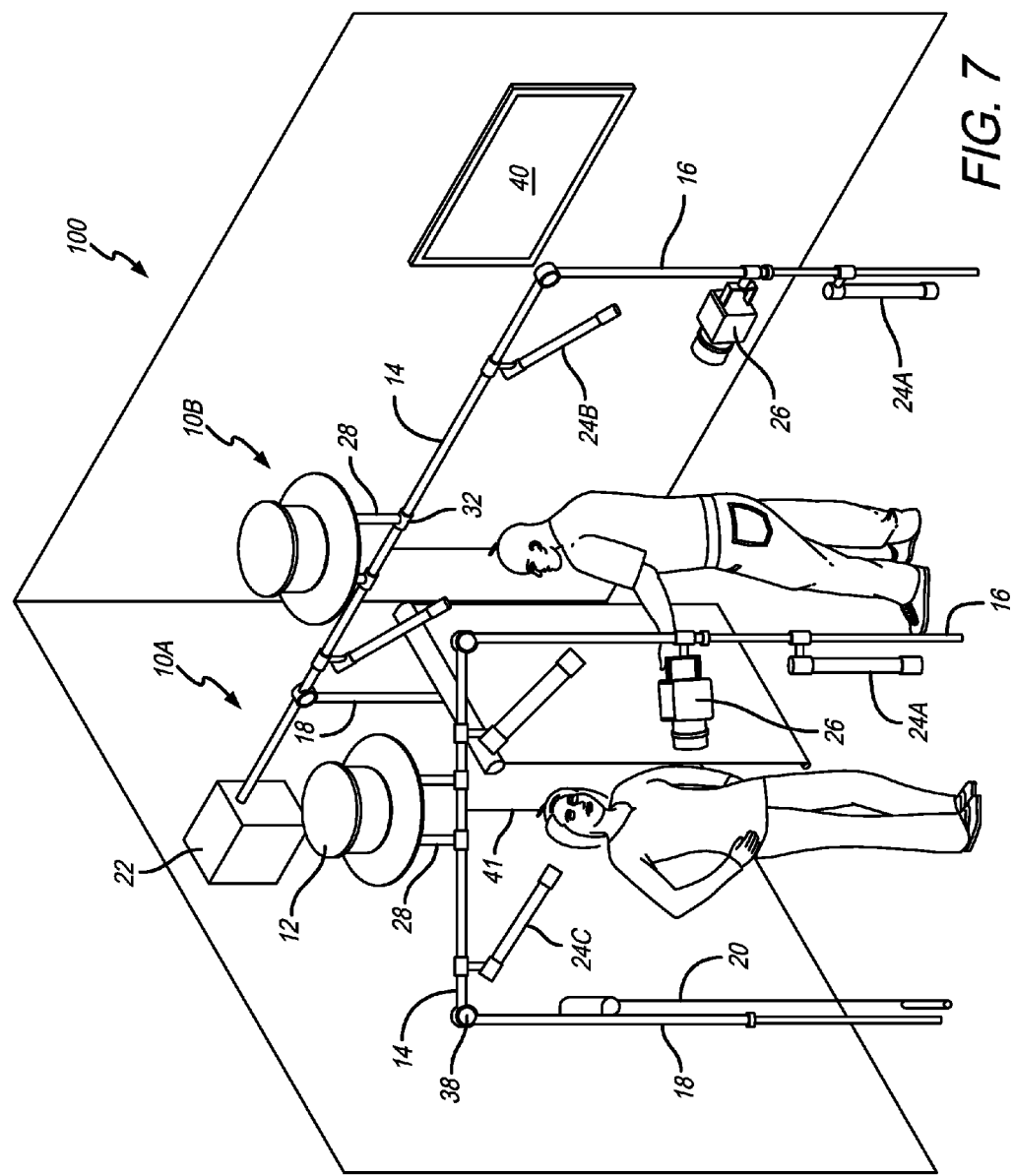
FIG. 7 is a perspective view of a dual 360° imaging system in accordance with another preferred embodiment of the present invention.
Figure 8:
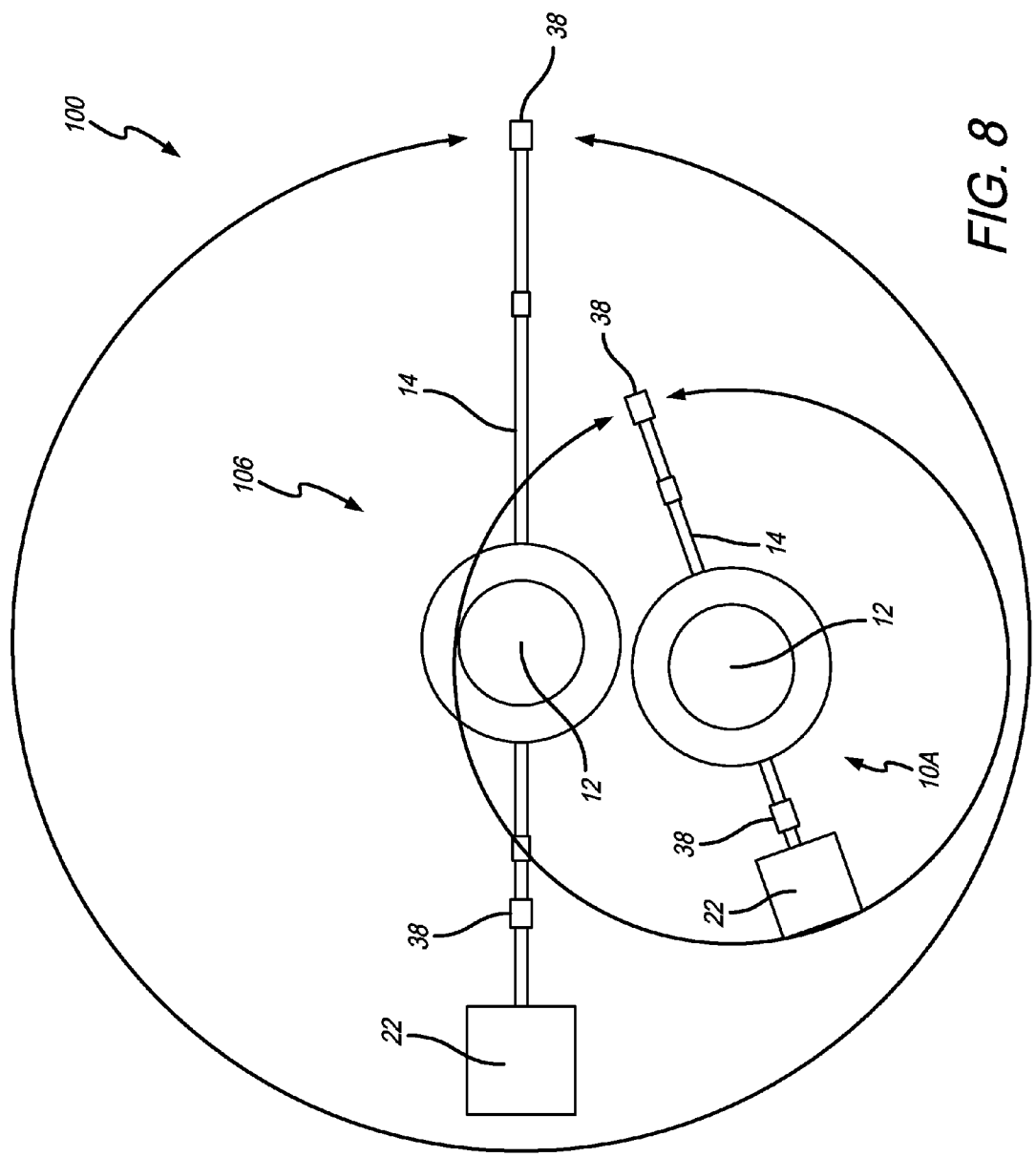
FIG. 8 is a top plan view of the dual 360° imaging system of FIG. 7.

FIGS. 7-8 show another embodiment of a 360° imaging system 200 that includes two systems 10a and 10b as described above that operate in conjunction with one another. In a preferred embodiment, this system 100 can be used to film two subjects that are each positioned under the rotation device 12 and co-axial with the substantially vertical axis defined by the rotation device 12. As shown in the figures, in a preferred embodiment, one system 10a has a shorter horizontal boom 14 than the other system 10b. This allows the booms 14 to rotate without components hitting one another. However, this is not a limitation on the present invention. As shown in FIG. 8, in a preferred embodiment, the systems 10a and 10b are positioned so that the first system 10a can rotate within the second system 10b.

Figure 9:
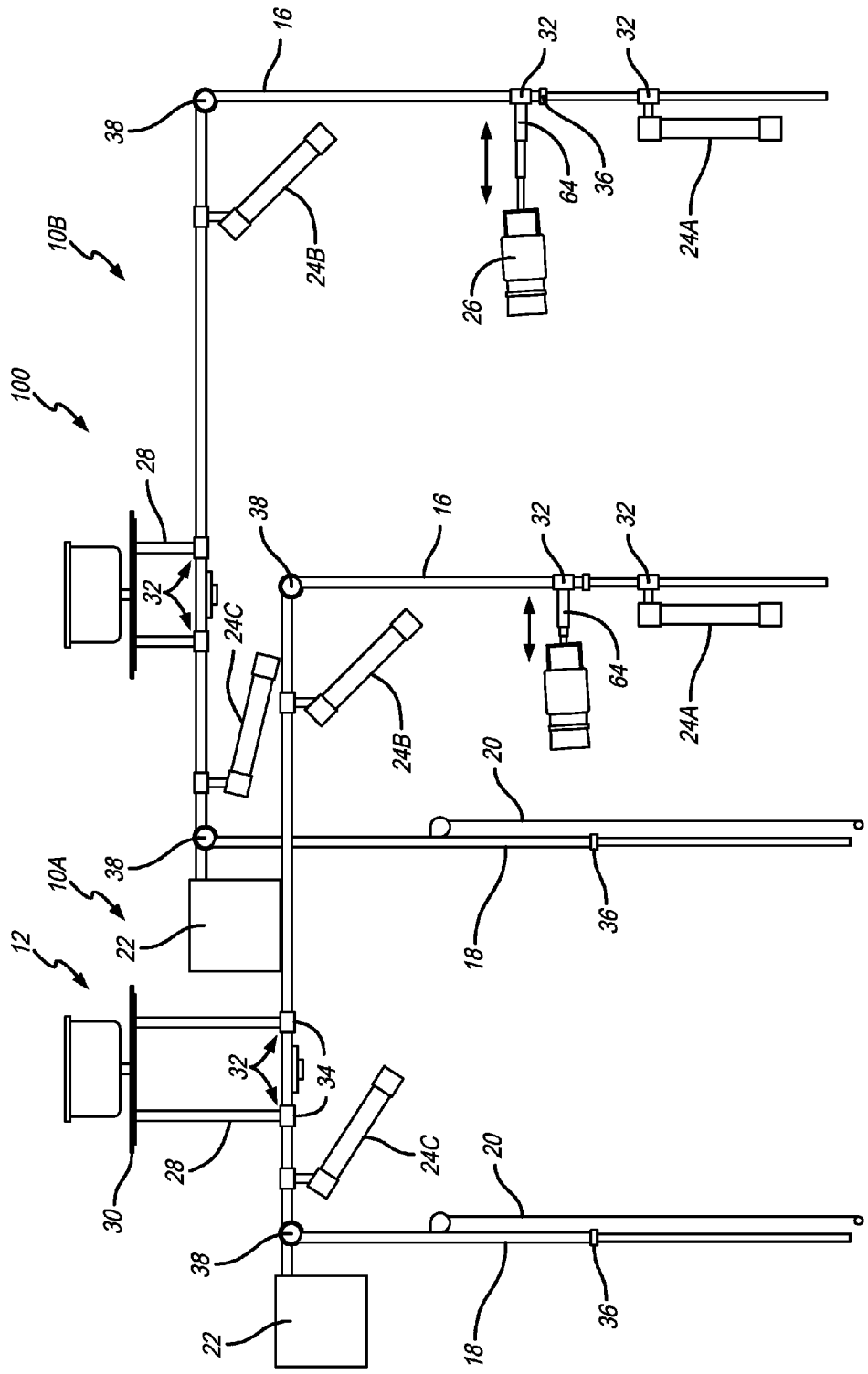
FIG. 9 is a side elevational view of the dual 360° imaging system of FIG. 7 with the camera mounted on a telescoping arm.

Also, in a preferred embodiment, the horizontal booms 14 are positioned at different heights to also allow movement without components hitting one another. This can be done by positioning the rotation devices 12 at different heights or providing different length shafts 28 and positioning the systems 10a and 10b as shown in FIG. 9. In a preferred embodiment, the system includes an arm 64 on which camera 26 is mounted and that moves horizontally (via telescoping or the like—see the arrows in FIG. 9) for close-ups and the like.

In an exemplary embodiment, the dual 360° imaging system 100 can be used in the film industry. For example, it can be used as a method for pre-visualization. It can be used to shoot scenes quickly with two actors who are each positioned under one of the rotation devices 12 and recite their lines. After shooting the scene and rotating each of the cameras 26 as desired, together with the backdrop 20 (which can be a blue screen or the like), the user has different angles to choose from without having to re-rig the camera, as has been done in the past. In this exemplary use, for pre-visualizing shoots, the dual 360° imaging system 100 allows a user to keep running a scene and have a plurality of different angles to choose from afterwards. And, the blue screen backdrop 20 stays lit behind the subject and the subject stays evenly lit because little changes between the camera 26 and the subject.

In an exemplary use, the subjects are each positioned on stools (or they can be standing) underneath the rotation devices of each of the systems. Then the cameras can separately be rotated around the two subjects as desired.

In another embodiment, the system can include the ability to move the camera in or out, i.e., in a horizontal direction. This can be done on an arm that moves horizontally, similar to the arms moving vertically described above. Or, the system can include a telescoping member on which the camera is mounted and that moves the camera toward and away from the subject. In a preferred embodiment, the movement of the system (rotation, up and down or in and out of cameras or arms) is automated. Therefore, in an exemplary use, a camera can move around the subject and then push in for a close up or pull back as desired. In a preferred embodiment, this can be done automatically at the sound of the director's voice.

Figure 10:
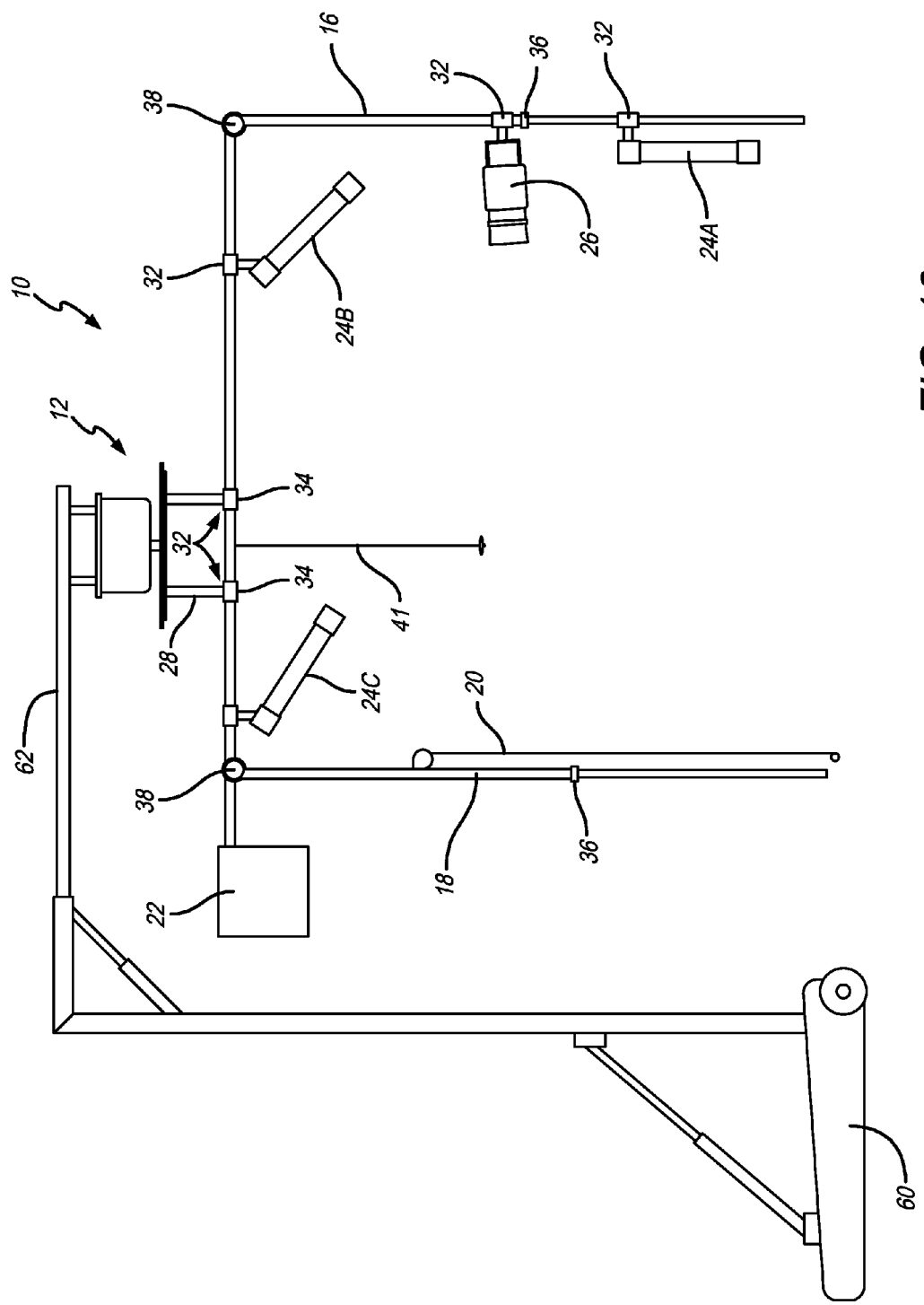
FIG. 10 is a side elevational view of a portable 360° imaging system in accordance with another preferred embodiment of the present invention.

As shown in FIG. 10, in another embodiment, the imaging system 10 can be portable. In a preferred embodiment, the system 10 includes a stand 60 or the like that includes an arm 62 that suspends the system 10 above the ground. In an exemplary embodiment, the stand 60 can be configured to be weighted down by being filled with water, sand or other material, similar to outdoor portable basketball systems. In yet another embodiment, the system can be positioned on a dolly or track so that the entire system can be moved horizontally and still be rotatable.

Figure 11A:
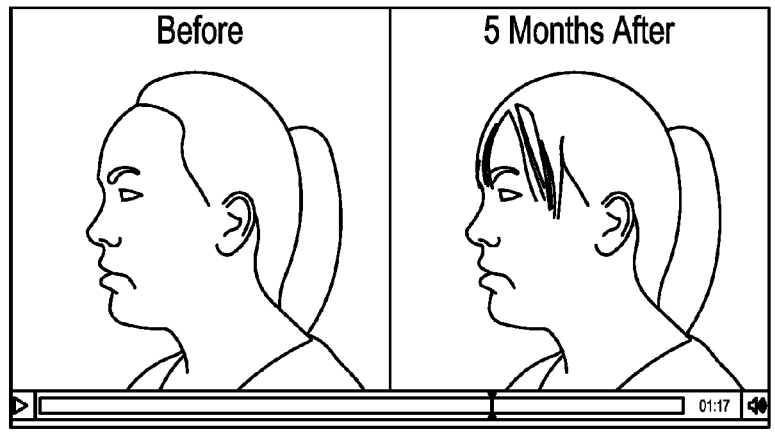
FIGS. 11A-11C are a series of images showing dual rotating before and after images in accordance with an embodiment of the present invention.
Figure 11B:
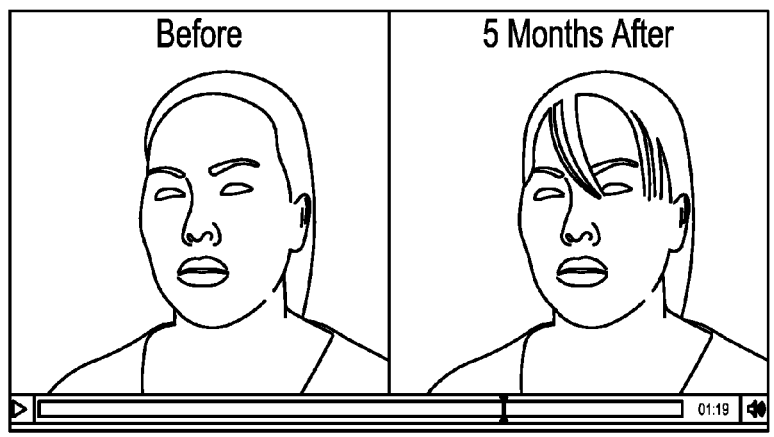
Figure 11C:
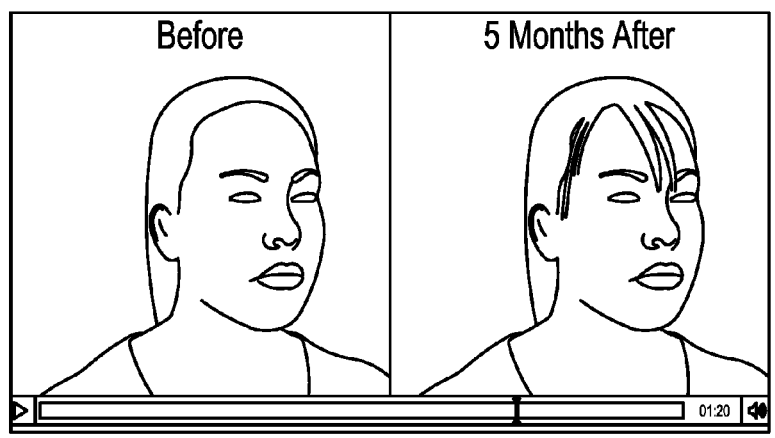
Figure 12:
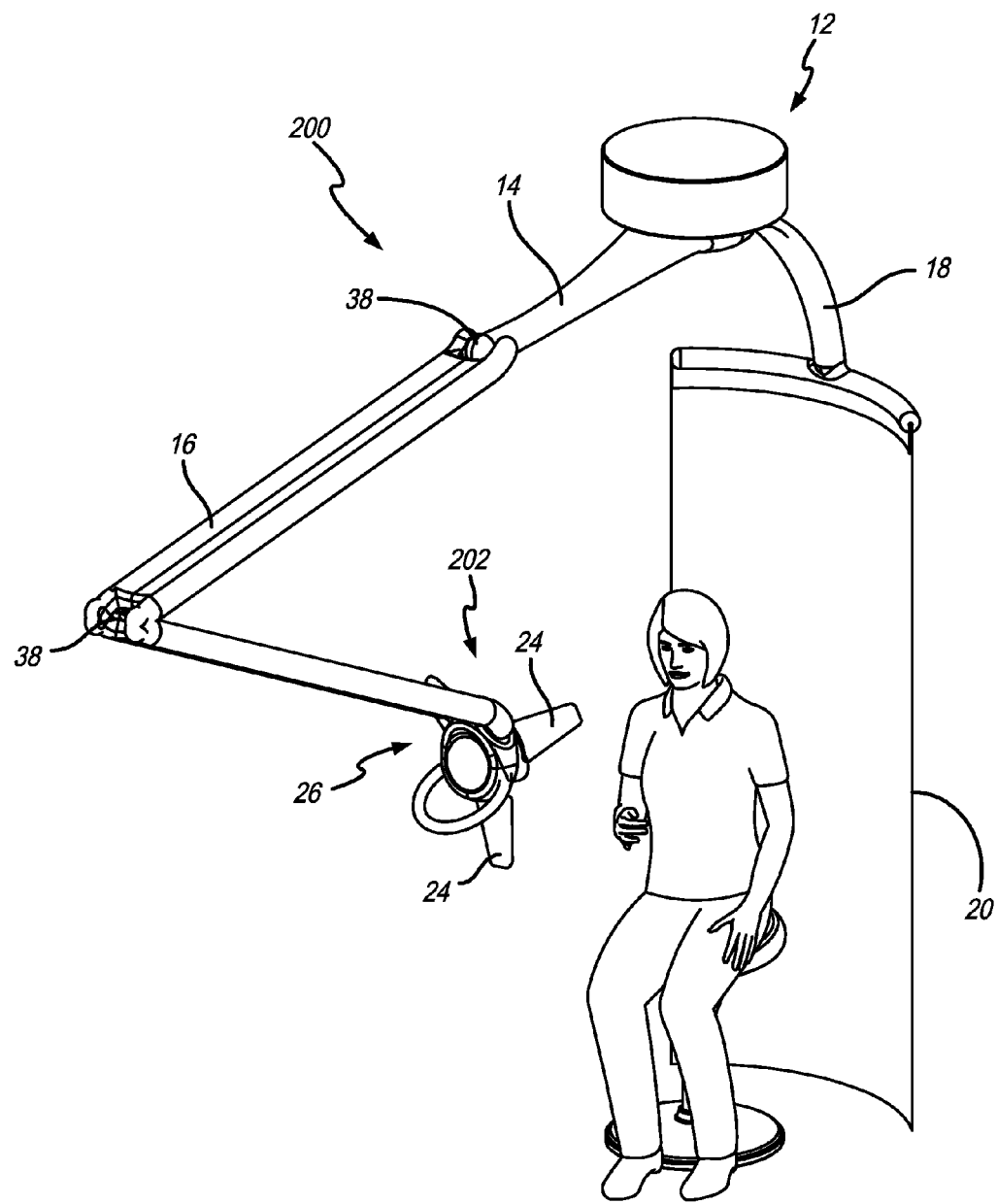
FIG. 12 is a perspective view of a 360° imaging system in accordance with a preferred embodiment of the present invention.

In a preferred embodiment, imaging system is used to capture and compare pre-surgical (or pre-event) images to post-surgical (or post-event) images of patients undergoing cosmetic procedures. Preferably, the image capturing system is configured to produce video as synchronized orbital shots of the patient. See, e.g., the images in FIGS. 11A-11C, which show a series of before and after images at different stages of a 360° rotation. Therefore, the viewer can see two rotating images next to each other that rotate in synchrony as a result of the images captured by the 360° imaging system.

Figure 13:
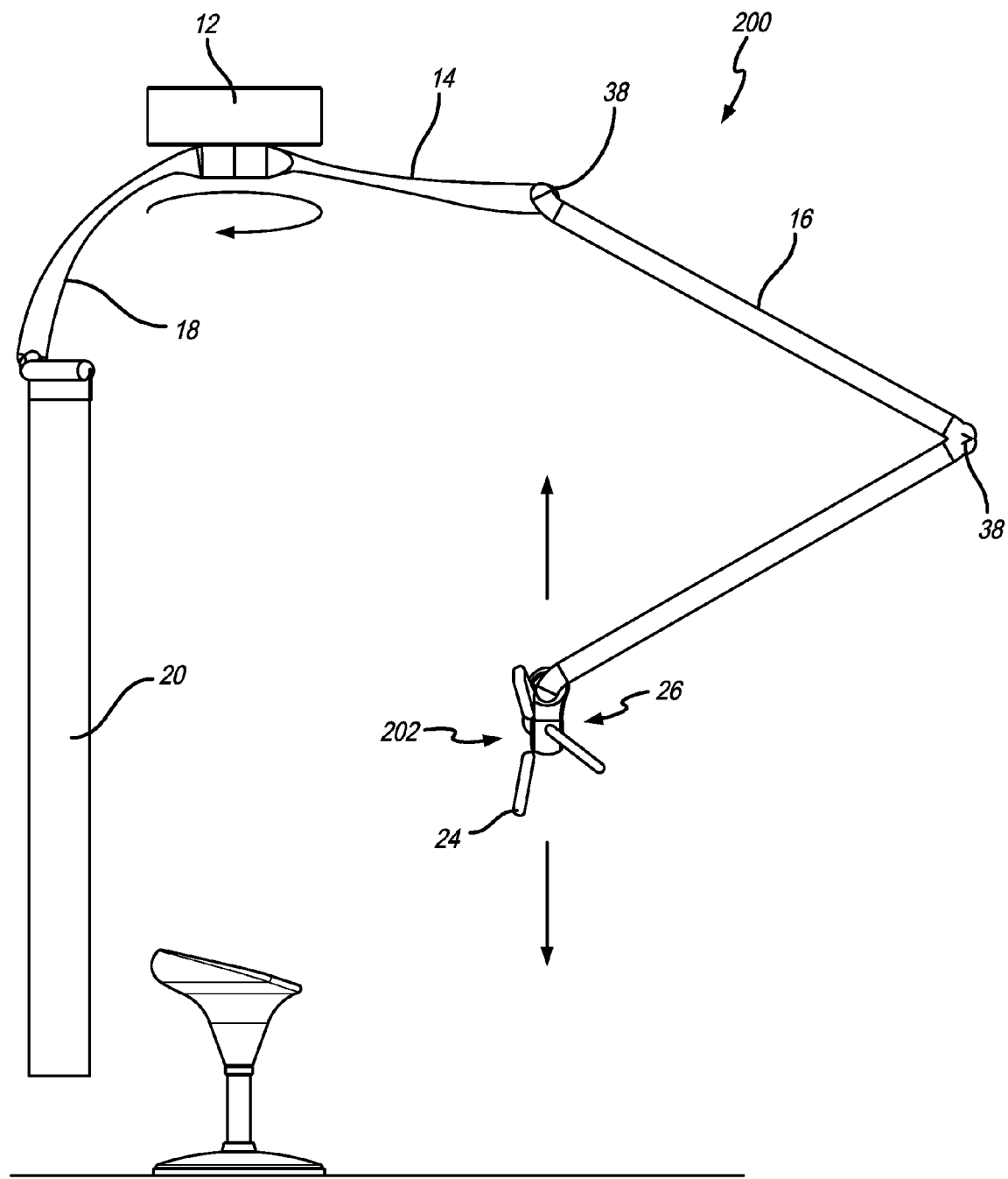
FIG. 13 is a side elevational view of the 360° imaging system of FIG. 12.
Figure 14:
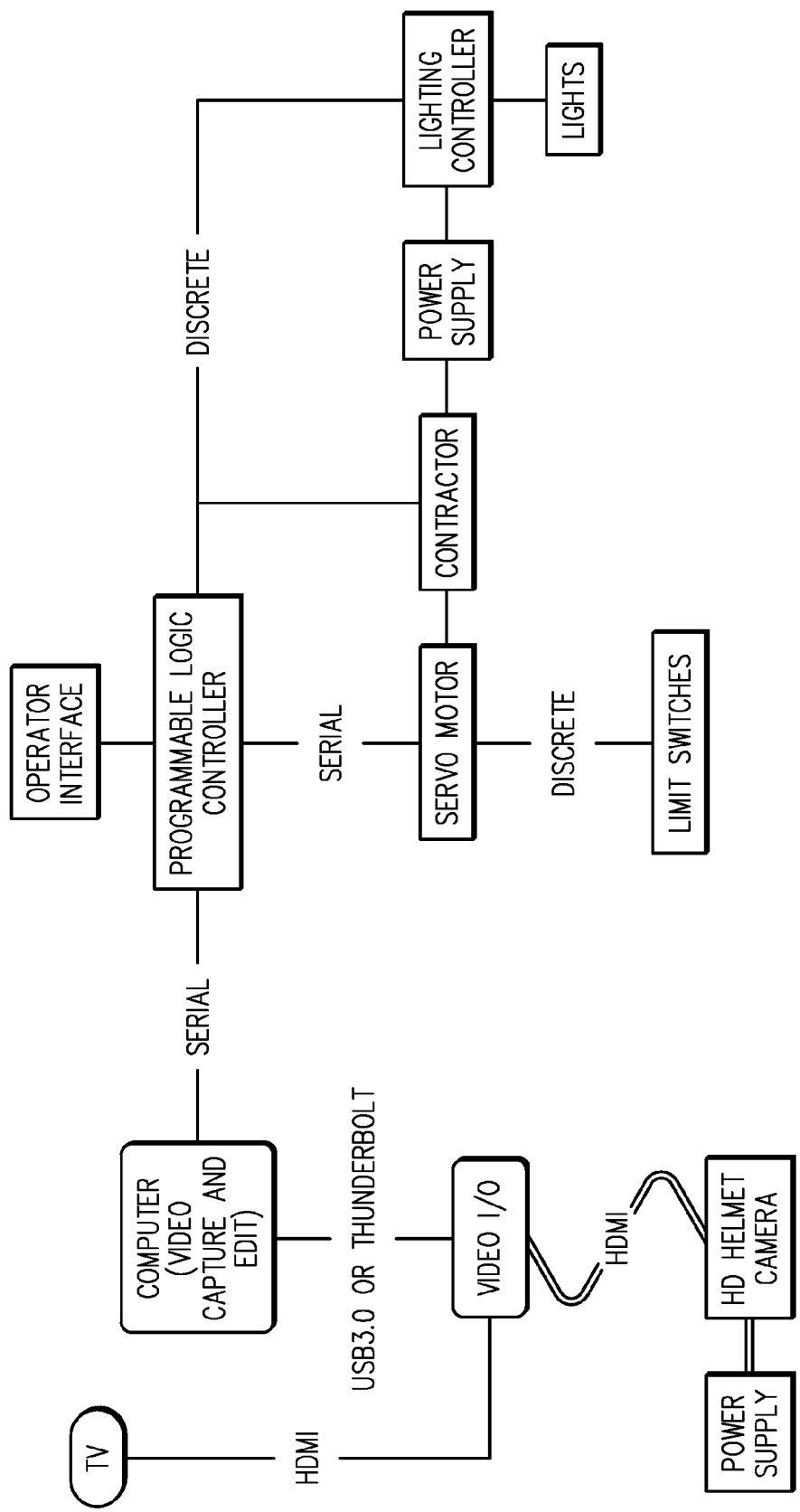
FIG. 14 is a flow diagram of exemplary electrical equipment used with the 360° imaging system of FIG. 12.
Figure 15:
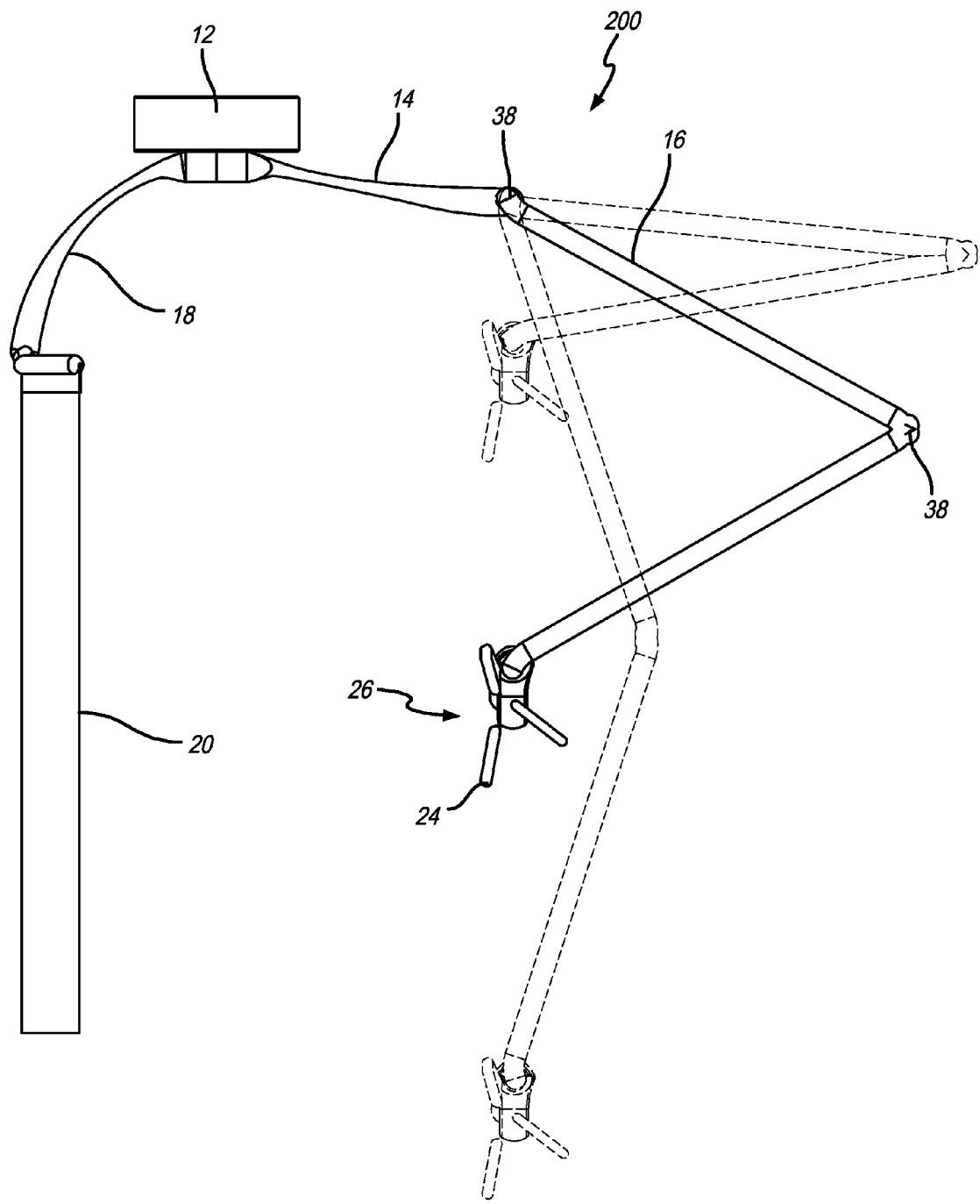
FIG. 15 is a side elevational view of the 360° imaging system of FIG. 12 showing the range of motion of the horizontal boom.

FIGS. 12-15 show another preferred embodiment of a 360° imagining system 200. Generally, the system 200 includes an upper boom 14, first and second downwardly extending vertical arms 16 and 18, backdrop 20 and camera or imaging device 26. As is shown in FIGS. 13 and 15, first downwardly extending vertical arm 16 includes joints or pivotal adjustment members 38 that allow camera or imaging device 26, and the assembly 202 in which it is housed, along with the lights 24, to movable upward and downwardly or toward or away from the subject to be imaged.

The 360° imaging system can be used in many different settings. For example, the system can be used by a dermatologist or other doctor to image a patient's skin to capture before and after images to observe changes over time in moles and other skin conditions. The system can also be used in a retail setting (e.g., a dressing room in a store) to allow a shopper to obtain a 360° image of the shopper wearing an outfit, shirt, pants, hat, etc. In this embodiment, the system can include means for downloading the image to a memory device, such as a flash drive, thumb drive, the shopper's phone, etc. This can be done wirelessly or via a data connection such as a USB or other known connection.

Figure 16:
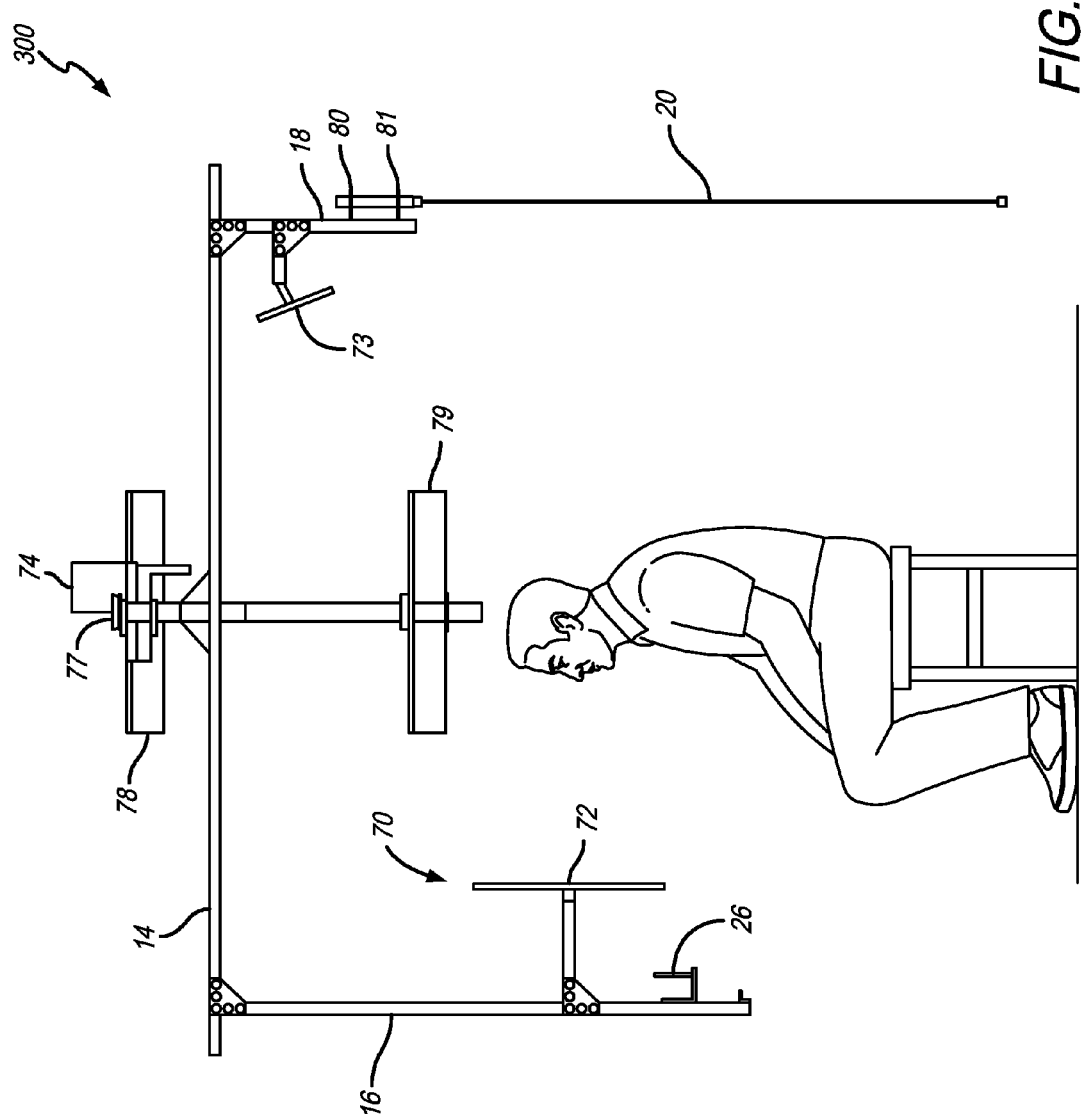
FIG. 16 is a side elevational view of a 360° imaging system in accordance with a preferred embodiment of the present invention.
Figure 17:
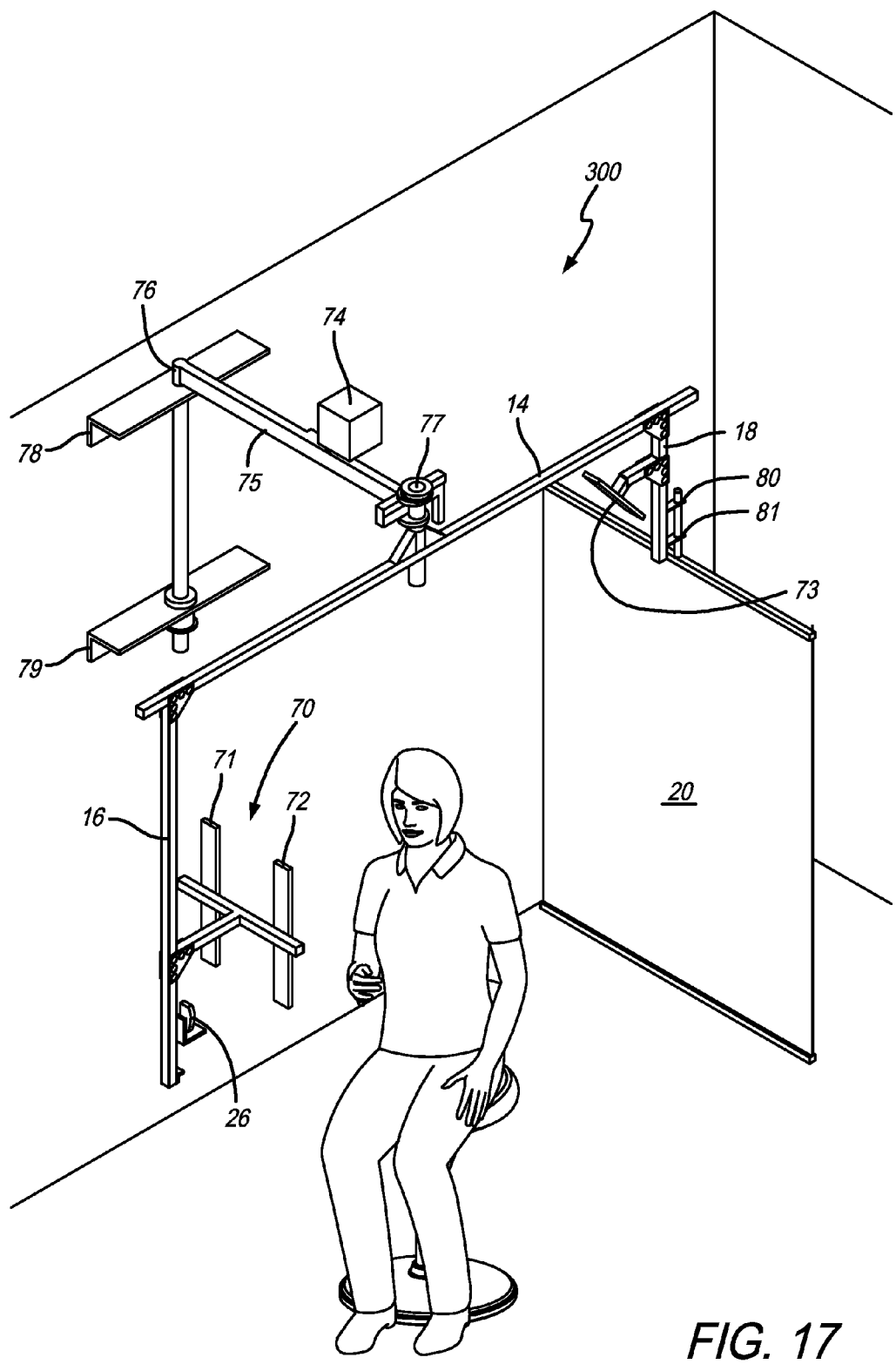
FIG. 17 is a perspective view of the 360° imaging system of FIG. 16.
Figure 18:
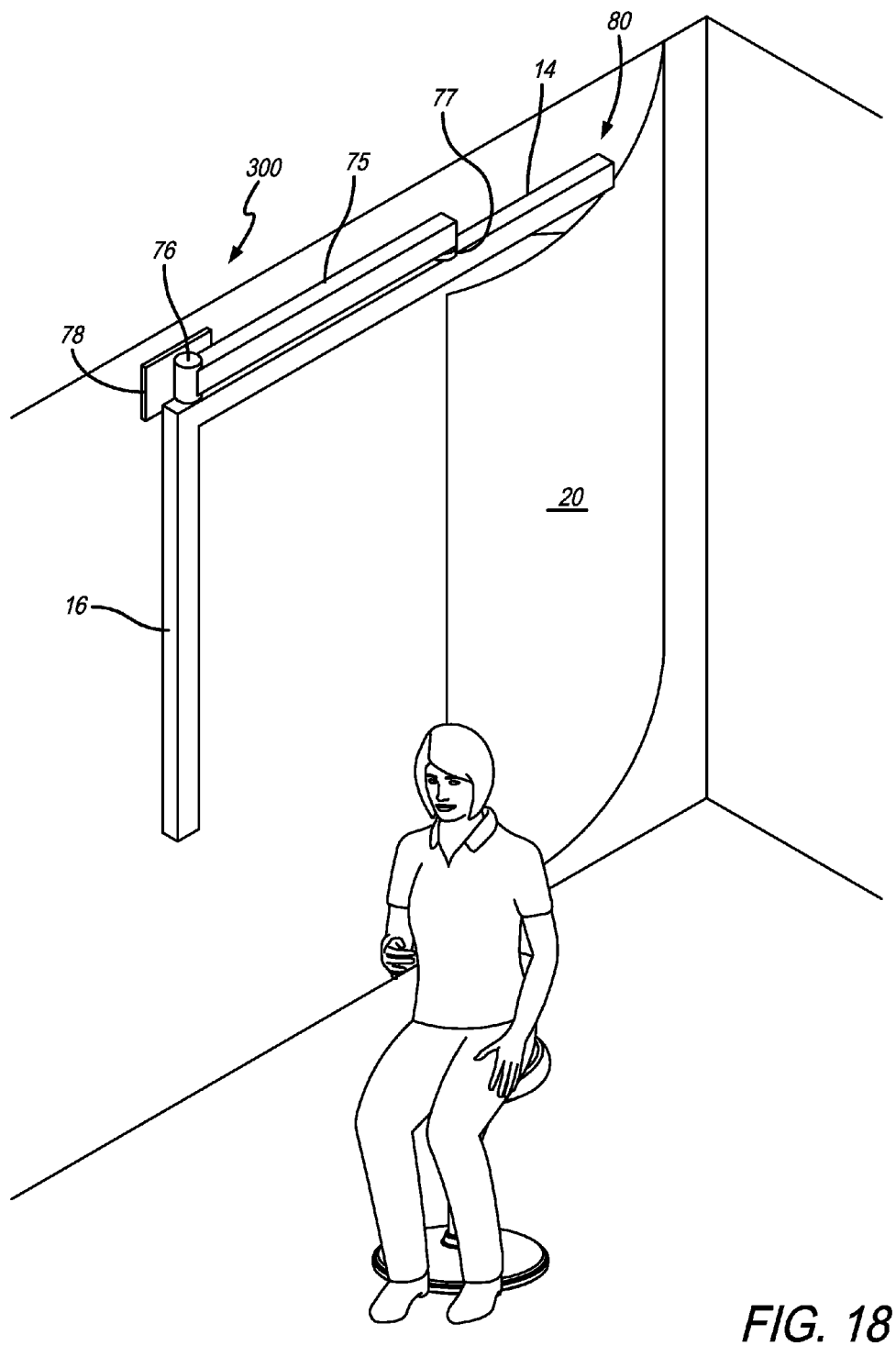
FIGS. 18 and 19 are a series of images showing fold-out and deployment movement of a 360° imaging system in accordance with a preferred embodiment of the present invention.

FIGS. 16-19 show another preferred embodiment of a 360° imaging system 300 that can fold flat or nearly flat against a wall or other surface when not in use (as depicted in FIG. 18). Generally, the system 300 includes a first horizontal boom 14, first and second vertical arms 16 and 18, backdrop 20, and camera 26. The system 300 is intended to be mounted to a wall, floor, or ceiling of a room or other fixture by way of mounting brackets 78 and 79. A single mounting bracket also may be used (as depicted by mounting bracket 78 in FIGS. 18 and 19). One end of a second horizontal boom 75 connects to mounting bracket 78 by way of a rotatable pivot 76, and the other end of the second horizontal boom 75 connects to the first horizontal boom 14 by way of another rotatable pivot 77, as can be seen in FIGS. 16-19. Camera 26 is intended to be a video camera, though it is contemplated that camera 26 could equally be a still camera, or any other imaging device known to a person of ordinary skill in the art (including any and all general or specific imaging devices discussed herein with respect to other embodiments). Moreover, multiple cameras (in any combination of video cameras, still cameras, or other imaging devices known to persons of skill or as discussed herein with respect to other embodiments), are contemplated and intended to be within the scope of the present invention.

Figure 19:
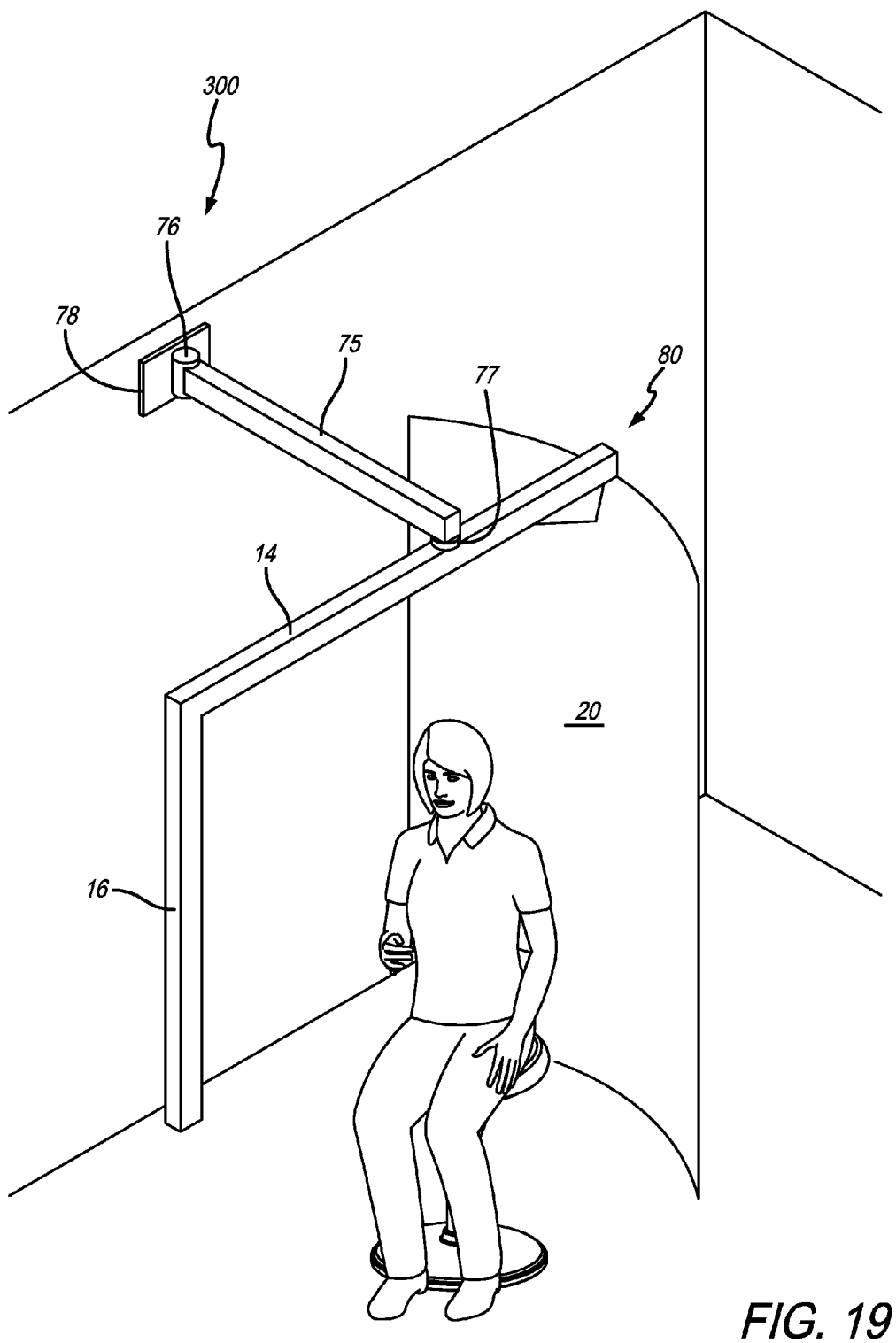

The system 300 includes a front lighting system 70, which includes lights 71 and 72. The system 300 includes a back fill light 73, which may be set at any angle, but is shown at a preferred angle of approximately 45 degrees. Backdrop 20, which may be flat (as depicted in FIGS. 16-17) or curved (as depicted in FIGS. 18-19), is attached to vertical arm 18 by way of pivots 80 and 81. It is contemplated that backdrop 20 may be attached to vertical arm 18 by way of a single pivot or any other fastening device or devices known to a person of ordinary skill in the art. Backdrop 20 also may be attached directly to first horizontal boom 14 by way of one or more pivots or other fastening device(s) known to a person of ordinary skill in the art.

In a preferred embodiment, the system 300 includes a motor system 74, which is preferably an electric motor, as shown in FIGS. 16 and 17. When the system 300 is not being used, it can be stored flat or nearly flat against a wall, as shown in FIG. 18. When the system 300 needs to be used, motor system 74 operates to swing the second horizontal boom 75 to a position that is essentially perpendicular to the mounting bracket 78, and concurrently, motor system 74 operates to swing the first horizontal boom 14 into a position that is essentially parallel to the mounting bracket 78. The movement of the first horizontal boom 14 in this manner is depicted in FIGS. 18 and 19. Because the backdrop 20 is mounted on one or more pivots (80 and/or 81), it is capable of rotating such that its plane becomes generally parallel to a patient's back when a patient is seated (as shown in FIGS. 16, 17, and 19). The movement of the backdrop 20 in this manner is depicted in FIGS. 18 and 19. Once the system 300 is placed into its operational position (shown in FIGS. 16, 17, and 19), motor system 74 causes the first horizontal boom 14 to rotate about the second rotatable pivot 77, while camera 26 captures images at a frequency and quality that can vary or be adjusted by the operator. In another embodiment, the movement of the first horizontal boom 14 and backdrop 20 can be achieved by hand or manual movement, without the use of a motor.

The operation and uses of system 300 are similar or identical to the operation and uses of the other preferred embodiments described and discussed herein, including for the purpose of capturing images before and after surgery or other medical procedures, such that the resulting images are standardized or taken under exactly the same conditions. Accordingly, because the lighting system 70 and backfill light 73 travel with the camera 26, the before and after images that can be captured are relatively consistent. Moreover, in order to standardize photographs, the system 300 may include a color scale light emitter, standing alone or directly connected to system 300, which allows for the standardization of color as among original and subsequent photographs. The system 300 also may include an LED (light emitting diode) centering light, either alone or directly connected to system 300, which projects a point of light at a standardized location (e.g., straight down from above), and allows the patient and/or camera system to be situated in the same or nearly the same position, as among original and subsequent photographs or image set capture.

And likewise, in system 300, a patient or subject is positioned in between the camera 26 and the backdrop 20. The camera 26 travels in a generally circular path around the patient or subject, preferably at least 360 degrees (though any number of degrees is contemplated as being within the scope of the present invention). The camera 26 captures multiple images (preferably at least five (5), but any number is contemplated), during the time camera 26 passes around the subject and a first image set is captured. At a later point in time (such as after surgery or following a given medical procedure), the above procedure is repeated, including the placement of the subject in the approximately or exactly the same position with respect to the original camera orientation, and a second image set is captured (again, preferably at least five (5) images, but any number is contemplated). The rate of camera movement during capture of the second image set may be the same or substantially the same as the rate of camera movement during capture of the first image set. A practitioner or other medical professional can then compare the first image set to the second image set and make any number of useful determinations or analyses, including the success of the surgery or medical procedure, progress of the patient post-surgery, and the like. From the resulting image sets, side-by-side comparisons also can be produced, as depicted, for example, in FIGS. 11A, 11B, and 11C.

Figure 22:
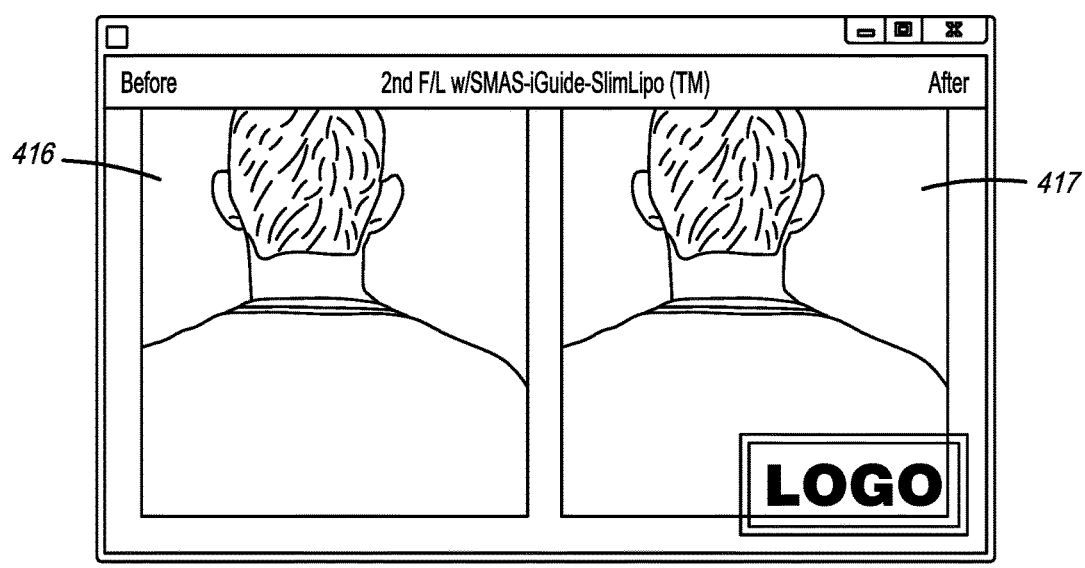
FIG. 22 is an exemplar screen shot of a computer implemented software preferred embodiment of the present invention.

In another preferred embodiment comprising computer implemented software 399 (the steps of which are shown and depicted in FIG. 20), the resulting before and after videos of systems 100, 200, and/or 300 are combined or "stitched" together into a single side-by-side video (FIG. 22), where the video frames of the before video generally (or exactly) match up with the corresponding frame of the after video. In other words, the before video is combined with and "synchronized" with the after video, to produce a single video where the before and after videos are displayed side-by-side, with the before video being displayed on the left side of the screen, and the after video being displayed on the right side of the screen (although any number of screen arrangements are contemplated and intended to be within the scope of the present invention, including but not limited to a top/bottom arrangement, and/or a reverse left/right arrangement). Multiple, individual "stitched" videos may be further combined with other "stitched" videos, sequentially, to produce a single video.

The computer implemented software additionally is capable of accommodating different lengths of before and after videos, i.e., the circumstance where the length of the before video is longer or shorter than the length of the after video. Synchronization is accomplished by offsetting the starting frame of the longer video, effectively "cropping out" the beginning and ending of the longer video, resulting in a video that is the same length as the shorter video. In practice, the starting frame of the shorter video is set to zero and the starting frame of the longer video is set to half of the difference in the number of frames of the two videos. The length of the resulting video is set to the length of the shorter video. In mathematical terms, the length of an input video is given by the frame rate (i.e., number of frames per second multiplied by the total number of frames). Because the before and after videos are recorded using the same software and camera systems 100, 200, or 300, the frame rate of the before and after video are generally or exactly the same.

The software implementation and operation for cropping the longer video can be understood through mathematical algorithm, where $N[Vx]$ represents the number of frames in video $Vx$, $S[Vx]$ represents the starting frame of video $Vx$, and $FLOOR(X)$ represents the truncated value of $X$. The videos are synchronized and stitched together by setting the starting frame of each video as follows:

For each specified pair of input videos of different lengths ($V_{SHORTER}$ and $V_{LONGER}$), where $N[V_{SHORTER}] \leq N[V_{LONGER}]$:

Let $S[V_{SHORTER}]=0$.
Let $S[V_{LONGER}]=floor((N[V_{LONGER}]-N[V_{SHORTER}])/2)$.
Stitch together $N[V_{SHORTER}]$ contiguous frames of each video.

Figure 20:
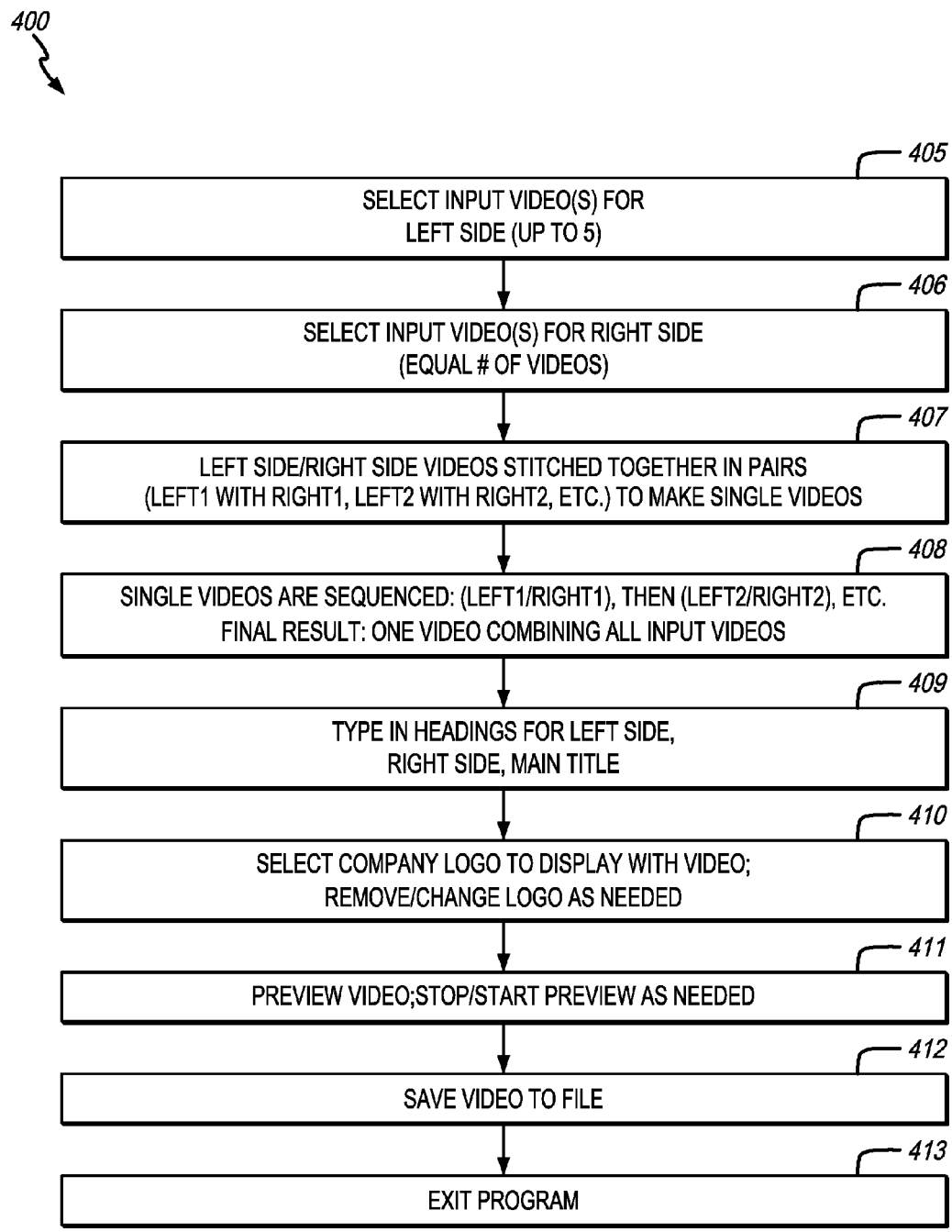
FIG. 20 is a flow chart showing the steps of a computer implemented software preferred embodiment of the present invention.
Figure 21:
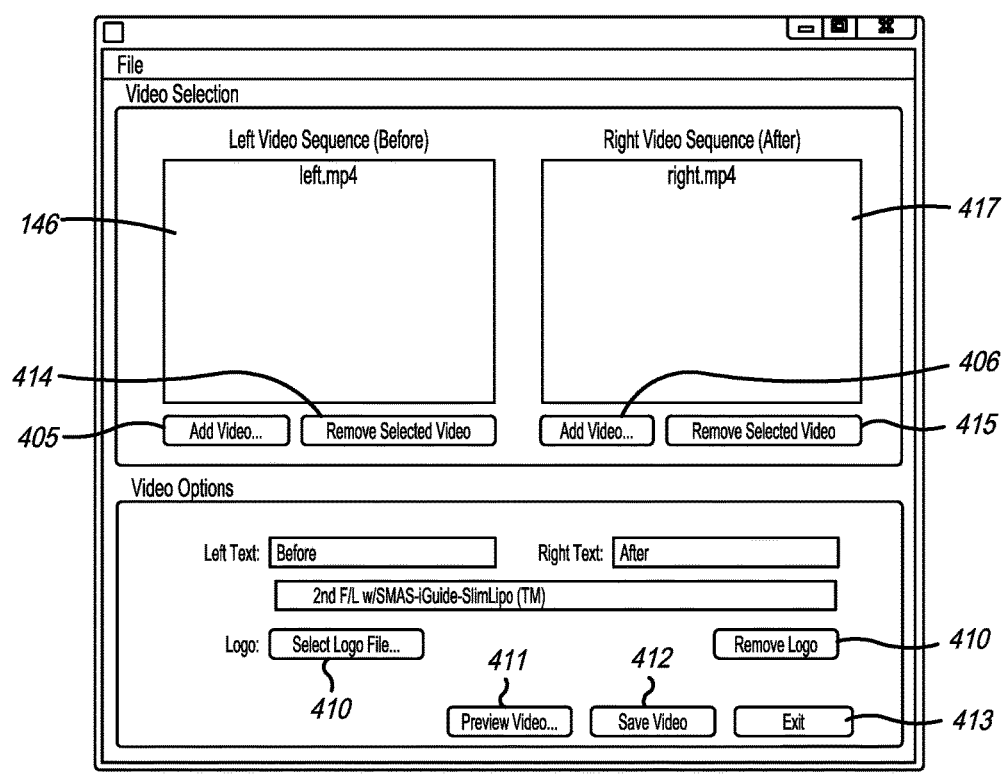
FIG. 21 is an exemplar screen shot of a computer implemented software preferred embodiment of the present invention.

Referring now to FIGS. 20-21, a flow chart is provided (FIG. 20) depicting the modules or steps of the software implementation of this preferred embodiment of the present invention, and an exemplar screen shot is provided (FIG. 21) depicting applicable on-screen buttons that correspond to one or more of the steps of FIG. 20. At module or step 405 of FIG. 20, the computer user selects up to five (5) input videos that are "before" videos (i.e., typically, but not necessarily, displayed on the left side of the screen). This module or step corresponds to button 405 of FIG. 21. At module or step 406 of FIG. 20, the computer user selects up to five (5) input videos that are "after" videos (i.e., typically, but not necessarily, displayed on the right side of the screen). This module or step corresponds to button 406 of FIG. 21. Also as shown in FIG. 21, one or more buttons 414 and 415 may be implemented to remove selected videos.

At module or step 407 of FIG. 20, the left side (before) and right side (after) videos are stitched together in pairs (e.g., Left1 with Right1, Left2 with Right2, etc.), to make single videos, using the mathematical algorithm for cropping and stitching described above. At module or step 408 of FIG. 20, single videos are sequenced, Left1/Right1, then Left2/Right2, etc., to form a final, single video that combines all input videos. At module or step 409 of FIG. 20, the computer user may type in headings for "Left Side" (Before) and "Right Side" (After), and a "main title" or similar. At module or step 410 of FIG. 20, a company logo can be selected and displayed. This module or step corresponds to button 410 of FIG. 21. At module or step 411 of FIG. 20, the resulting video can be viewed by the computer user. This module or step corresponds to button 411 of FIG. 21. At module or step 412 of FIG. 20, the video is saved to a storage medium, and at module or step 413 of FIG. 20, the user exits the computer program. These modules or steps correspond to buttons 412 and 413, respectively, of FIG. 21. The left (before) and right (after) videos are displayed, as shown at 416 and 417, respectively, in FIGS. 21 and 22.

Software and web or internet implementations of this preferred embodiment of the present invention are performed using standard programming techniques using rule based logic or other logic to accomplish the various modules or steps that have been described for this preferred embodiment, as will be known and understood to those of skill in the art. It should also be noted that the terms "component," "module," or "step," as may be used herein and in the claims, are intended to encompass implementations using one or more lines of software code, macro instructions, hardware implementations, and/or equipment for receiving manual inputs, as will be well understood and appreciated by those of ordinary skill in the art. Such software code, modules, or elements may be implemented with any programming or scripting language such as C, C++, C#, Java, Cobol, assembler, PERL, Python, PHP, or the like, or macros using Excel, or other similar or related applications, with various algorithms being implemented with any combination of data structures, objects, processes, routines or other programming elements known to those of skill in the art. Such programming code is intended to be stored on hardware storage devices, i.e., nonvolatile, computer readable storage media (e.g., hard disk, server, or other hardware devices known to persons of ordinary skill in the art), and the code comprises computer-executable instructions, data structures, program modules, and other data for a computing device, which are executed by a computer CPU (or a corresponding processor of such other components).

One or more of the modules or steps of this preferred embodiment also may be stored or recorded on a server, and/or transmitted over network, to be accessed and utilized by a computer device, or any other computing device that may be connected to the server and/or network. The computer implemented software 399 of this preferred embodiment of the present invention interacts with, and is implemented by, the machine of systems 100, 200, and/or 300.

Unless otherwise indicated, the terms "image set" and "video," as used herein, are intended to have the same meaning, and the terms "image" and "frame," as used herein, are intended to have the same meaning. Also, unless otherwise indicated, the term "side-by-side" is intended to include any configuration where images are adjacent to one another, including but not limited to a top/bottom configuration and a left/right configuration.

Figure 23:
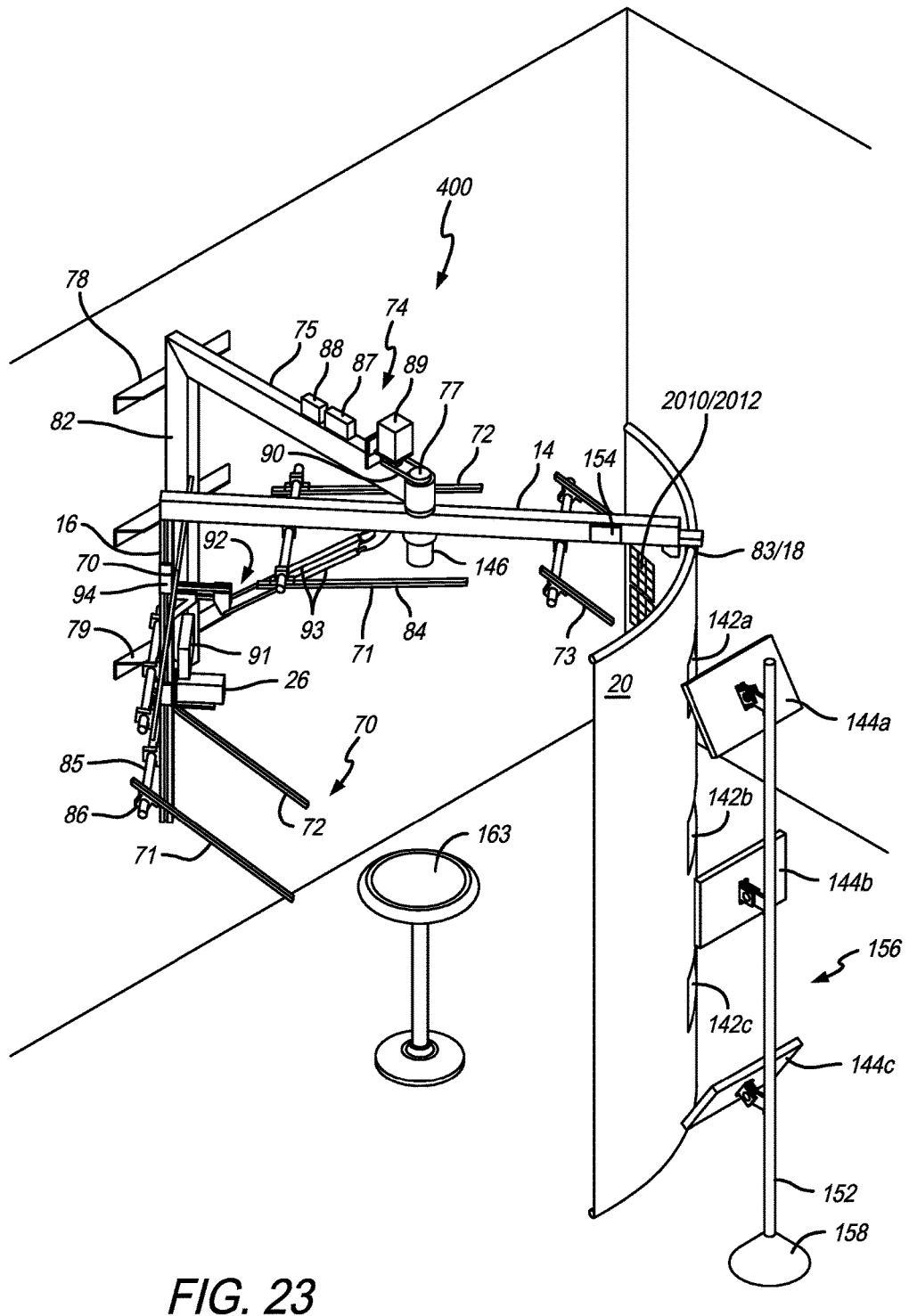
FIG. 23 is a perspective view of a 360° imaging system in accordance with a preferred embodiment of the present invention

FIGS. 23-32 show another preferred embodiment of a 360° imaging system 400. This system can be attached to a wall or other surface, as shown in FIG. 23 or can be portable. Generally, the system 400 includes a first horizontal boom 14, first and second vertical arms 16 and 18, backdrop 20, and camera 26. It will be appreciated that in this embodiment, the second vertical arm 18 and backdrop 20 are combined or the second vertical arm 18 is a bracket 83 for holding the back drop 20. The system 400 is intended to be mounted to a wall, floor, or ceiling of a room or other fixture by way of mounting brackets 78 and 79 and wall mount arm 82. A single mounting bracket or more than two mounting brackets also may be used. One end of a second horizontal boom 75 extends outwardly wall mount arm 82. The other end of the second horizontal boom 75 connects to the first horizontal boom 14 by way of a rotatable pivot 77. In a preferred embodiment, camera 26 is a video camera, though it is contemplated that camera 26 could equally be a still camera, or any other imaging device known to a person of ordinary skill in the art that can capture images (including any and all general or specific imaging devices discussed herein with respect to other embodiments). Moreover, multiple cameras (in any combination of video cameras, still cameras, or other imaging devices known to persons of skill or as discussed herein with respect to other embodiments), are contemplated and intended to be within the scope of the present invention.

Figure 24A:
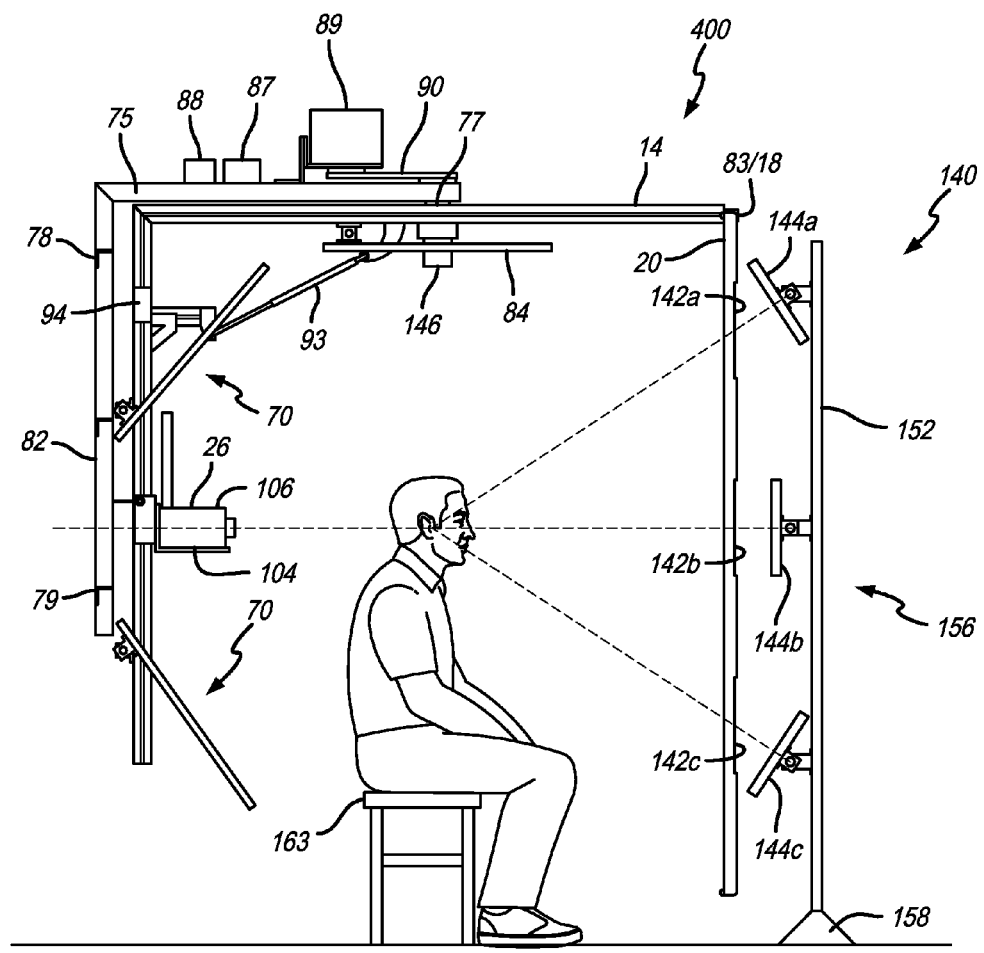
FIGS. 24A-24C are side elevational views of the imaging system of FIG. 23 and an alignment system in accordance with a preferred embodiment of the present invention.
Figure 24B:
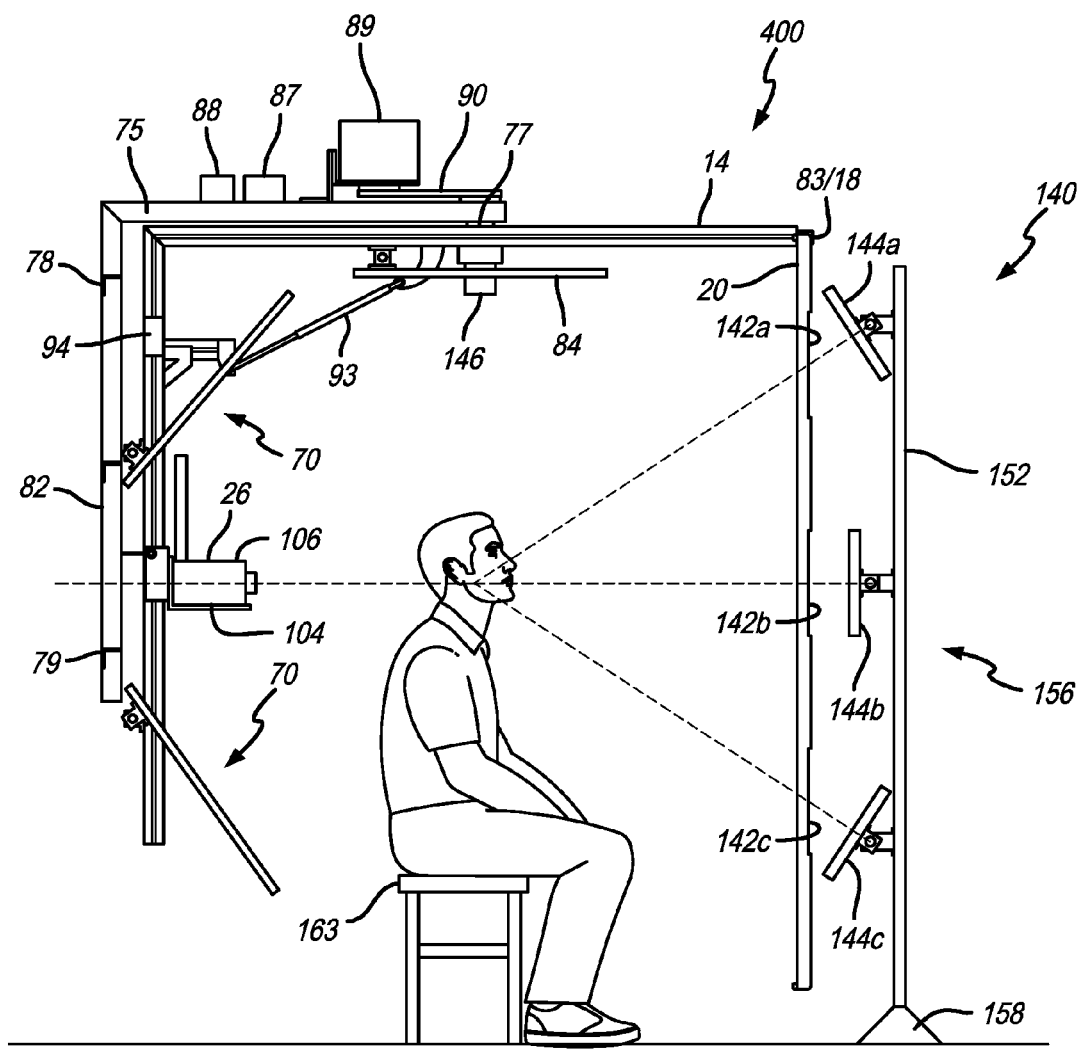
Figure 24C:
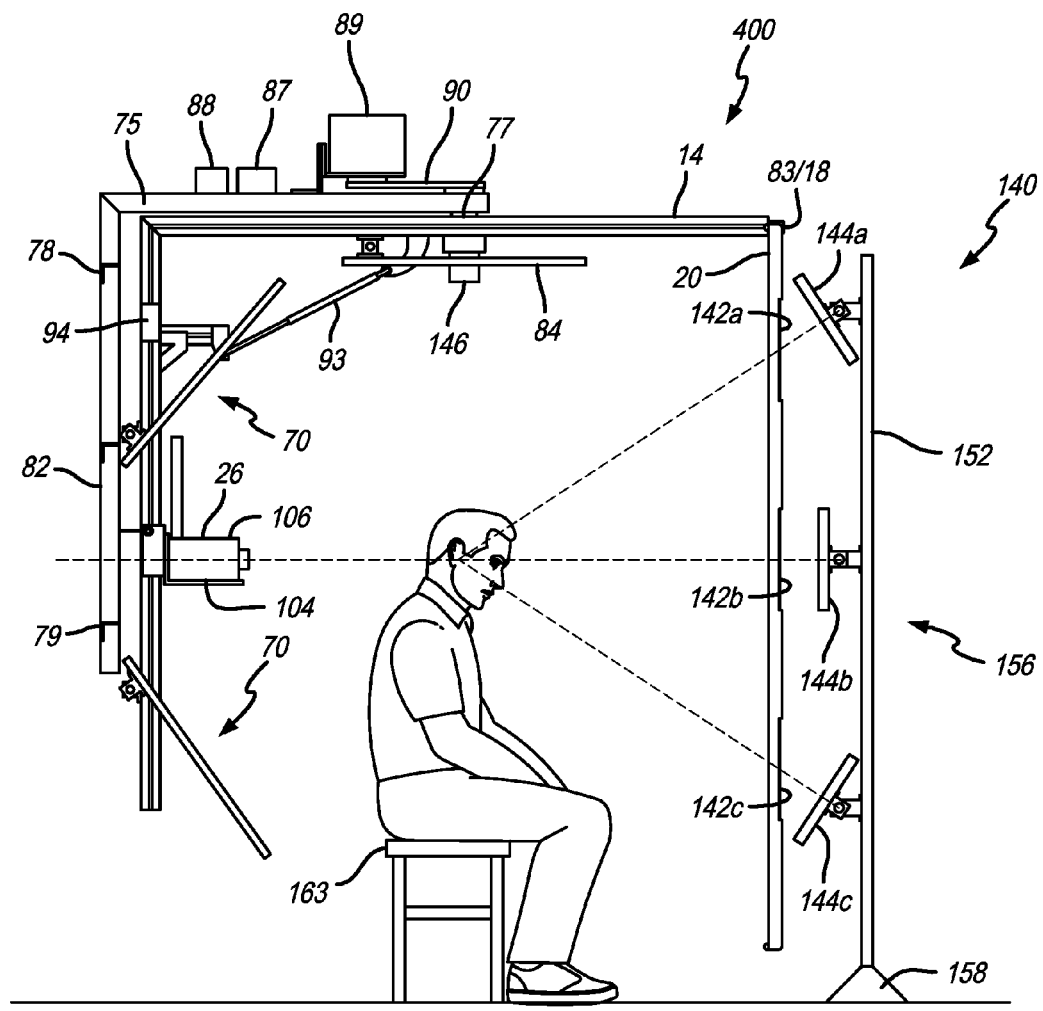

In a preferred embodiment, the system 400 includes at least one and preferably a multiplicity of lighting systems. As is best shown in FIGS. 23-24C, in a preferred embodiment, the system 400 includes at least one and preferably two front lighting systems 70, and an overhead lighting system 84, which each include lights 71 and 72. The system 400 can also include a direct front light 91. The system 400 can also include a back fill light 73, which may be set to shine light on the subject or on the backdrop 20. In a preferred embodiment, the lighting systems are movable and/or adjustable. For example, front lighting system 70 can be movable vertically on first vertical arm 16 and the lights 71 and 72 can be pivotal. Pivotal movement can be provided by a rod 85 that is received in a clamp 86 that can be tightened or loosened when desired.

In a preferred embodiment, at least a portion of the first vertical arm 16 can pivot to a horizontal or other non-vertical orientation when not in use. FIG. 23 shows a pivot assembly 92 that includes gas springs 93 and a hinge or pivot joint 94 about which the lower portion of the first vertical arm 16 can pivot.

In a preferred embodiment, the system 400 includes motor system 74 that operates or rotates the first horizontal boom 14 about rotatable pivot 77, while camera 26 captures images at a frequency and quality that can vary or be adjusted by the operator. In another embodiment, the movement of the first horizontal boom 14 and backdrop 20 can be achieved by hand or manual movement, without the use of a motor. Any type of motor system is that provides rotational movement is within the scope of the present invention. The motor system 74 is for providing rotation to the rotating unit (first horizontal boom, backdrop and camera and associated components). In a preferred embodiment, the motor system 74 includes a stepper motor controller 87, microstep driver 88, and a stepper motor 89 that together operate a belt 90 that operates rotatable pivot 77. The motor system 74 is in communication with a remote controller, such as a computer 123 (see FIG. 32). Wires (not shown) for electrical and data communication can run inside or outside the hollow arms or booms (14, 16, 75, 82, etc.) as desired.

The operation and uses of system 400 are similar or identical to the operation and uses of the other preferred embodiments described and discussed herein, including for the purpose of capturing images before and after surgery or other medical procedures, such that the resulting images are standardized or taken under exactly the same conditions. Accordingly, because the lighting systems travel with the camera 26, the before and after images that can be captured are relatively consistent.

Similar to the systems described above, in system 400, a patient or subject is positioned in between the camera 26 and the backdrop 20. The camera 26 travels in a generally circular path around the patient or subject, preferably at least 360 degrees (though any number of degrees is contemplated as being within the scope of the present invention). The camera 26 captures multiple images (preferably at least five (5), but any number is contemplated), during the time camera 26 passes around the subject and a first image set is captured. At a later point in time (such as after surgery or following a given medical procedure), the above procedure is repeated, including the placement of the subject in the approximately or exactly the same position with respect to the original camera orientation, and a second image set is captured (again, preferably at least five (5) images, but any number is contemplated). The rate of camera movement during capture of the second image set may be the same or substantially the same as the rate of camera movement during capture of the first image set. A practitioner or other medical professional can then compare the first image set to the second image set and make any number of useful determinations or analyses, including the success of the surgery or medical procedure, progress of the patient post-surgery, and the like. From the resulting image sets, side-by-side comparisons also can be produced, as depicted, for example, in FIGS. 11A, 11B, and 11C.

FIGS. 23-29 show systems for aligning a patient's head and may be particularly useful for repeatability in before and after images related to plastic surgery. It will be appreciated that the alignment systems and methods described herein can be used with any of the 360° imaging systems described herein. However, this is not a limitation on the present invention and the alignment systems can be used as desired.

FIGS. 23-29 show an embodiment of an alignment system 140 that can be used with system 400. The system 140 includes the curved backdrop 20 (the screen can also be flat or other shape) with upper, center and lower openings 142a, 142b and 142c defined therein. As shown in FIG. 24A, when the backdrop or screen 20 is at the home position, upper, center and lower monitors 144a, 144b and 144c are positioned behind the openings. As described herein, the three openings and associated monitors allow three different head positions that can be imaged for before and after images/videos. In another embodiment only a single opening and associated can be used. In another embodiment two or more than three openings and associated monitors can be used.

Figure 25:
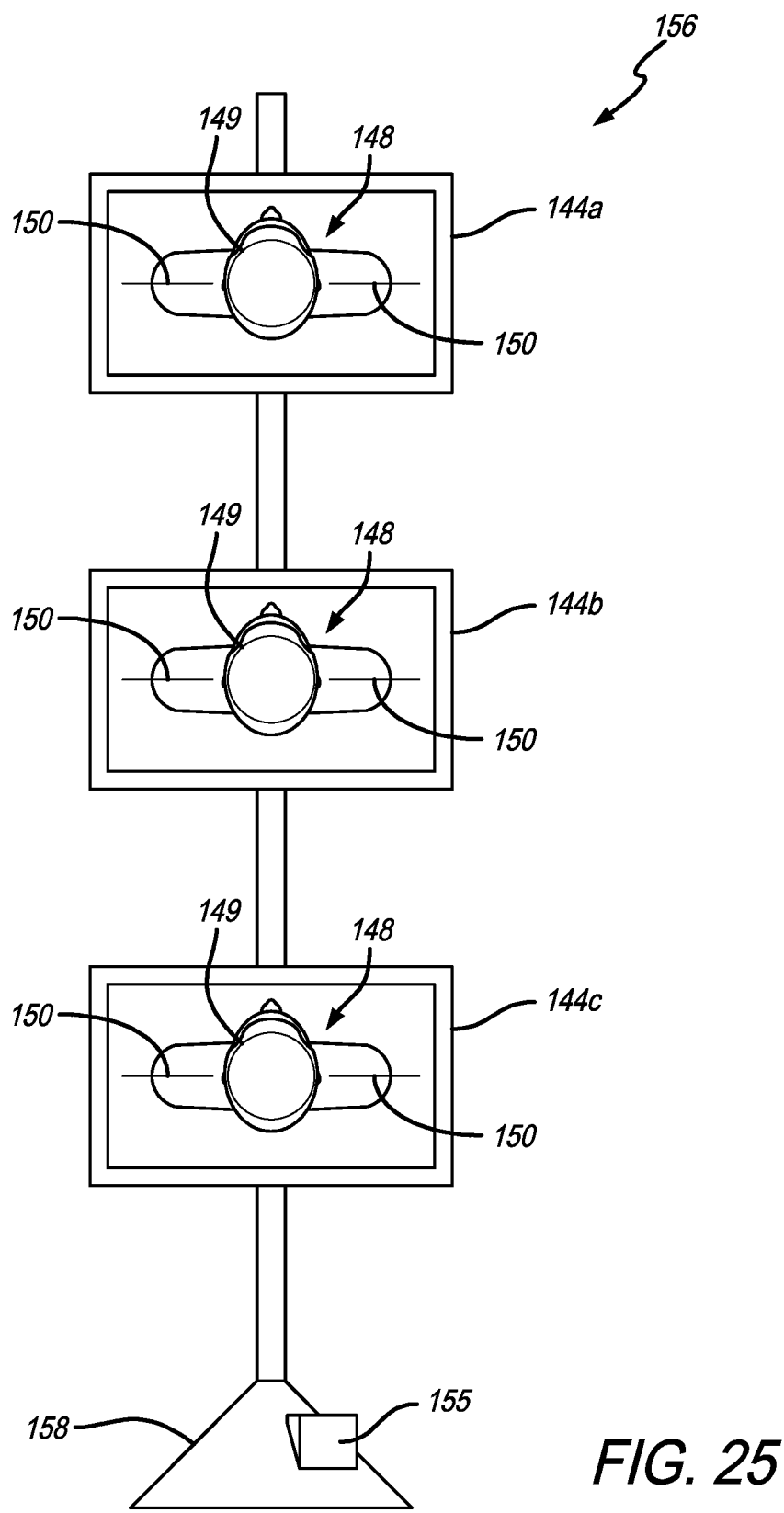
FIG. 25 is an elevational view of the monitor assembly used with the alignment system showing the alignment markings thereon and showing an image of a patient displayed on each of the monitors.
Figure 26:
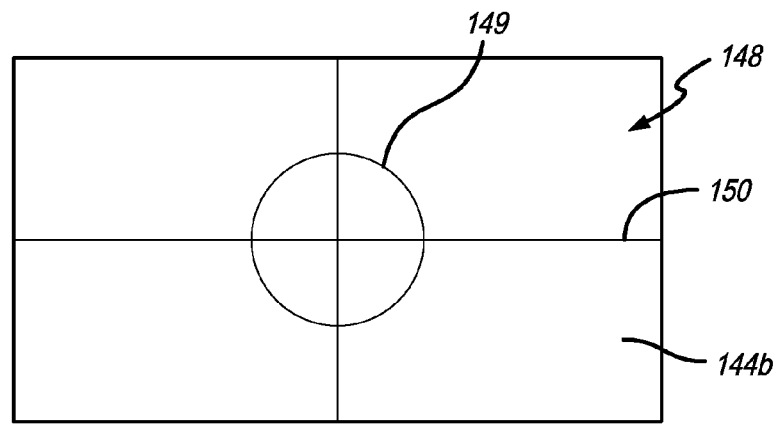
FIG. 26 shows a monitor that includes alignment markings thereon.

In a preferred embodiment, the openings 142a, 142b and 142c and monitors 144a, 144b and 144c are positioned such that a patient can look straight ahead (the central or neutral monitor 144b—see FIG. 24A) with their head tilted up (the tilt up or upper monitor 144a—see FIG. 24B) and with their head tilted down (the tilt down or lower monitor 144c—see FIG. 24C). The monitors are used in conjunction with an alignment camera 146 that is positioned above the patient and preferably is co-axial with the pivot axis of the camera 26 and backdrop 20 (rotatable pivot/pivot mechanism 77). The image captured by the alignment camera 146 can be viewed on the upper, center and lower monitors 144a, 144b and 144c. In a preferred embodiment, as shown in FIG. 25, the upper, center and lower monitors 144a, 144b and 144c each include alignment markings 148 thereon that aid with the patient's alignment and centering. For example, a circle 149 for positioning of the patients head and lines 150 for positioning of the patient's shoulders and to aid in centering can be included on the monitors. In use, the circle 149 is used to center the head and the patient can rotate or move their upper body so that their shoulders are aligned with the one or two horizontal lines 150. The markings 148 can be stickers or the like that are placed on the monitor or can be images projected thereon. The positioning of the monitors in conjunction with the alignment camera 146 allow a patient to keep the angle of chin flexing and extension approximately the same in both before and after images.

As shown in FIG. 25, in a preferred embodiment, the upper, center and lower monitors 144a, 144b and 144c are mounted on a pole 152 as part of a monitor assembly 156 with a base 158. In another embodiment, the monitors can be mounted on the wall or another type of standard or device. In another embodiment, the monitors c144a, 144b and 144c can be part of the rotating unit. The image from the alignment camera 146 can be communicated to the monitors via wiring or wirelessly. As shown in FIGS. 23 and 25, in an exemplary embodiment a wireless transmitter 154 is mounted on horizontally oriented boom 14 and a wireless receiver 155 is mounted on the base 158 of the monitor assembly 156. In an embodiment, the monitors can be adjustable vertically. As shown in FIGS. 24A-24C, in a preferred embodiment, the upper and lower monitors 144a and 144c are tilted toward the patient.

Figure 28:
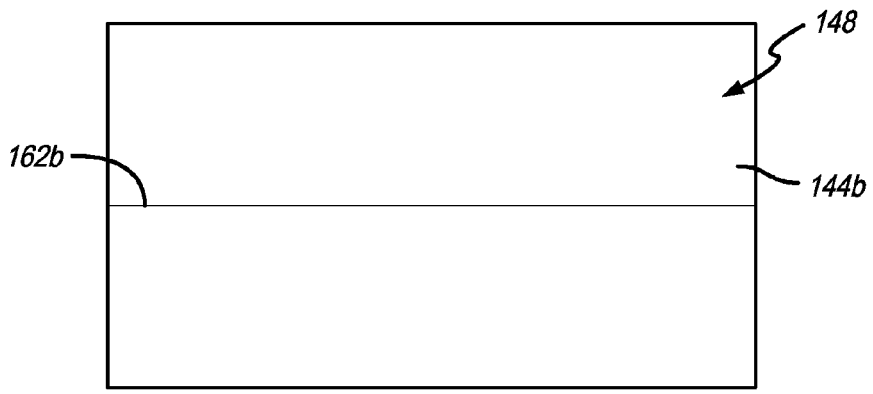
FIG. 28 shows a monitor that includes alignment markings thereon.

An exemplary alignment using the neutral or center monitor 144b will be described. Prior to starting the scan, the patient is seated in a chair or stool that is vertically adjustable. The patient adjusts the seat to a position such that their eyes are directly in line with the center opening 142b in the screen and the central monitor 144b behind it. As shown in FIG. 28, the monitor 144b can include a line there on for positioning the patient's sight line. Next, the imaging camera 26 is oriented such that it is directed towards the back of the patient's head, as shown in FIG. 24A. Therefore, the imaging camera 26 is aligned with the patient's head, which is aligned with the center opening 142b in the screen 20, which is aligned with the center monitor 144b therebehind. The alignment camera 146 is positioned directly above the patient and is directed downwardly toward the top of the patient's head. As discussed above, the alignment camera 146 is preferably positioned such that it is positioned directly in the center of the rotating system. The image from the alignment camera 146 appears on the center monitor 144b (and the tilt up and tilt down monitors when they are used). The patient can then use the alignment markings or template 148 to position, align and or center their head and body using the markings, so they are centered on the monitor.

A 360 degree (or more, e.g., 420 degree) scan is then taken. As the imaging camera 26 rotates the screen/backdrop 20 rotates opposite it and the center monitor 144b goes out of view and is not seen on the video as the scan continues around the circumference of the face, body etc. If desired, scans can be taken of the patient tilting their head upwardly (using the upper monitor 144a) and/or downwardly (using the lower monitor 144c). The head and shoulder alignment markings are used in the same manner.

After the desired scans are taken and plastic surgery is performed, the patient can come back at a later time to repeat the process and obtain "after" scans/images/videos. It will be appreciated that the alignment system 140 provides a high degree of repeatability such that the before and after scans are readily comparable.

This system 140 allows the patient to orient themselves in the XYZ planes. In other words, the patient can position himself/herself so that they are sitting up straight, they are in repose, their chin is not tilted up or down, they're not leaning left or right and they are looking directly through the center opening to the neutral monitor. In an embodiment, the system can be voice automated such that the patient can be prompted to look straight, up, down. The voice activation directs the patient through the specific imaging routine and protocol. The voice activation controls also preferably have the ability to command the rotating unit to rotate, record, approve and disapprove captured image, for example.

Figure 43:
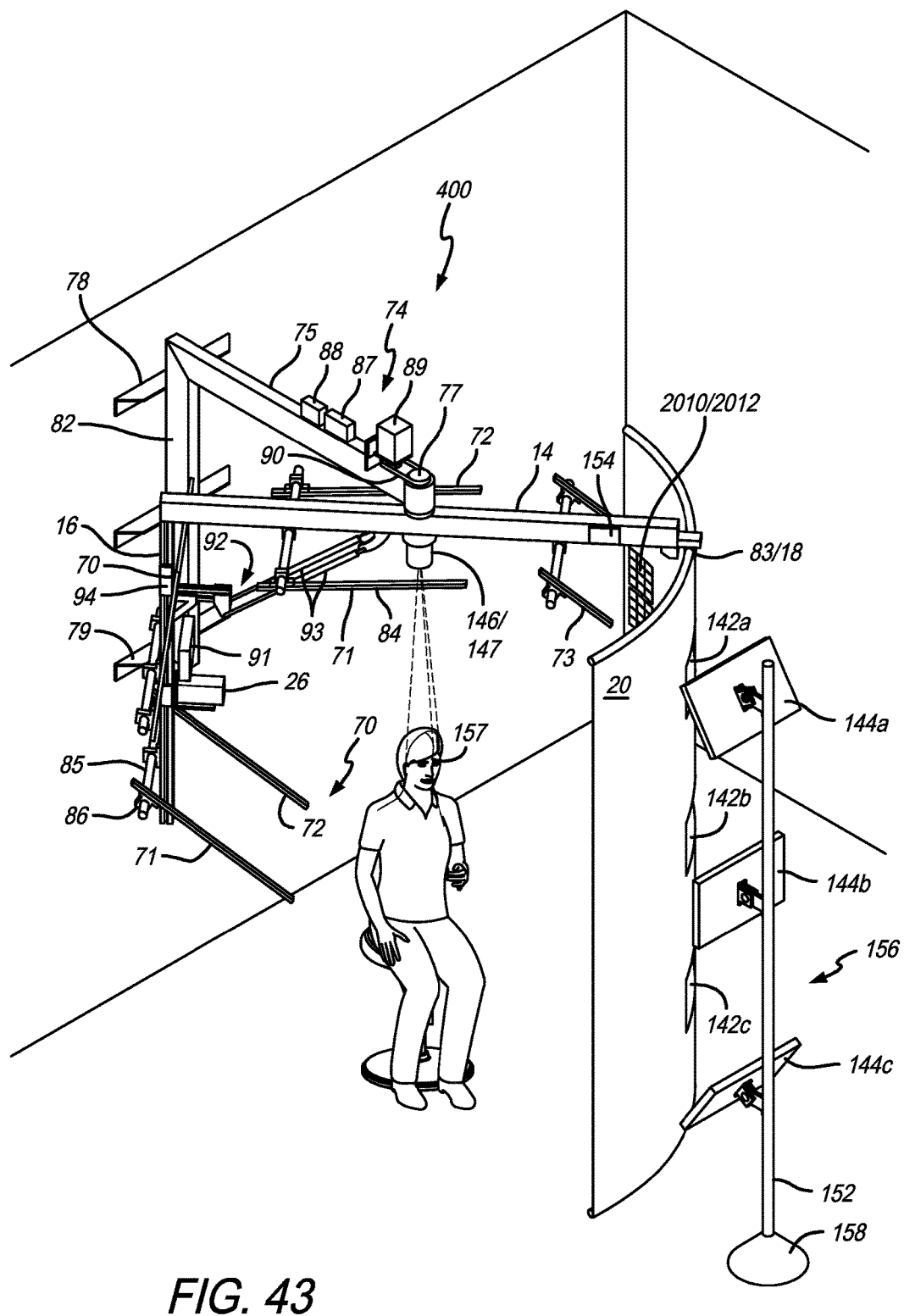
FIG. 43 is a perspective view of a 360° imaging system with a projected image alignment system in accordance with a preferred embodiment of the present invention
Figure 44:
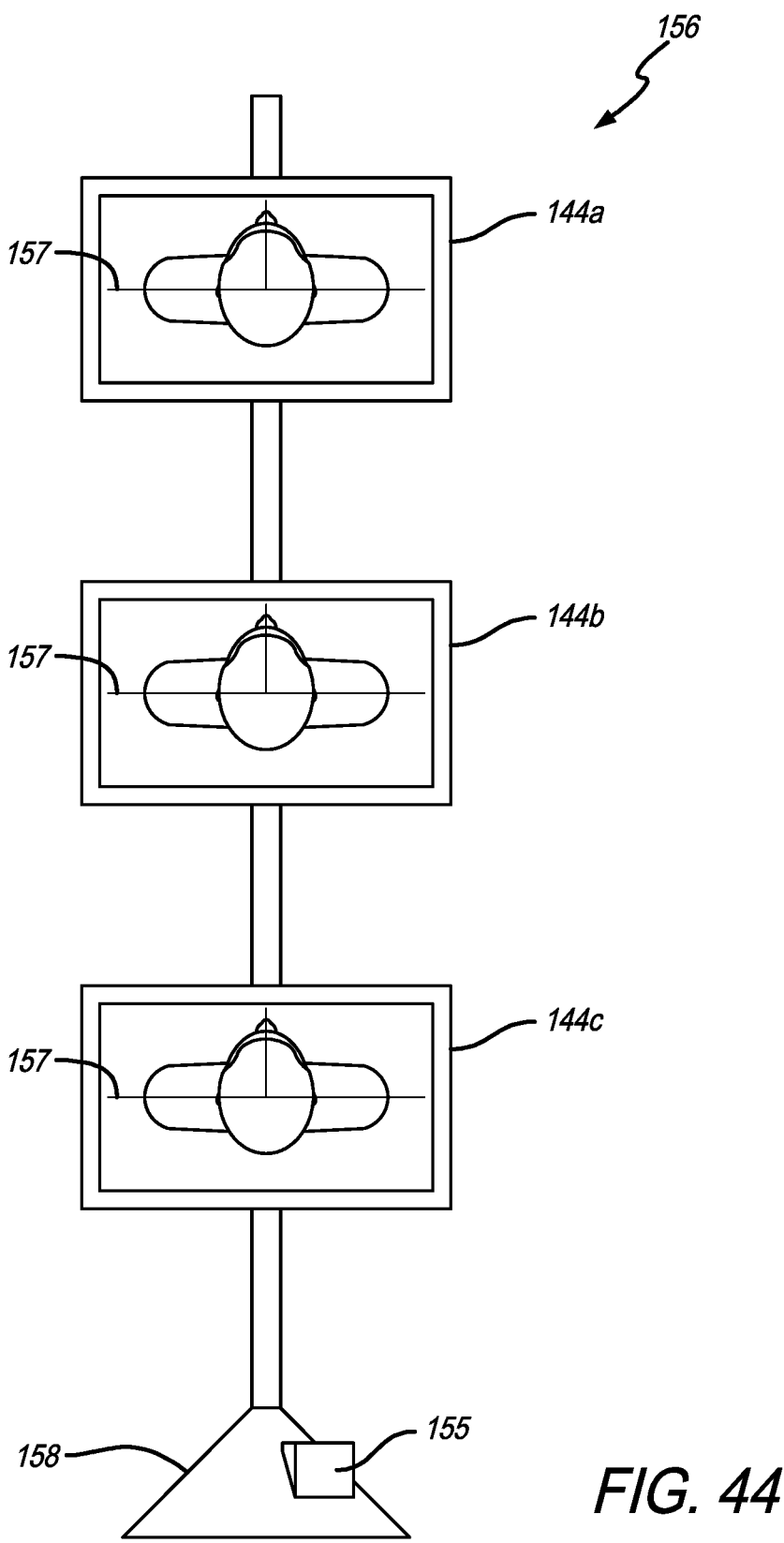
FIG. 44 is an elevational view of the monitor assembly used with the alignment system showing an image of a patient displayed on each of the monitors and showing the projected image on top of the patient's head.

As shown in FIGS. 43-44, in another embodiment, the alignment system 140 includes a light/projector 147 that projects or directs light downwardly on top of the patient's head. The light is preferably in the form of a projected image 157 that forms a "T", "+" or other grid. In use, similar to the embodiment above, the patient can view his or her head in the monitors 144a, 144b or 144c. However, instead of (or in addition to) using the alignment markings, the patient can use the projected image 157 to align themselves properly. In an embodiment using the T shaped projected image 157, the patient can align one portion of the T with their nose and the other portion with their ears, as shown in FIG. 44. The projected image 157 can come from any light source, e.g., laser, LED, incandescent, etc.

Figure 45:
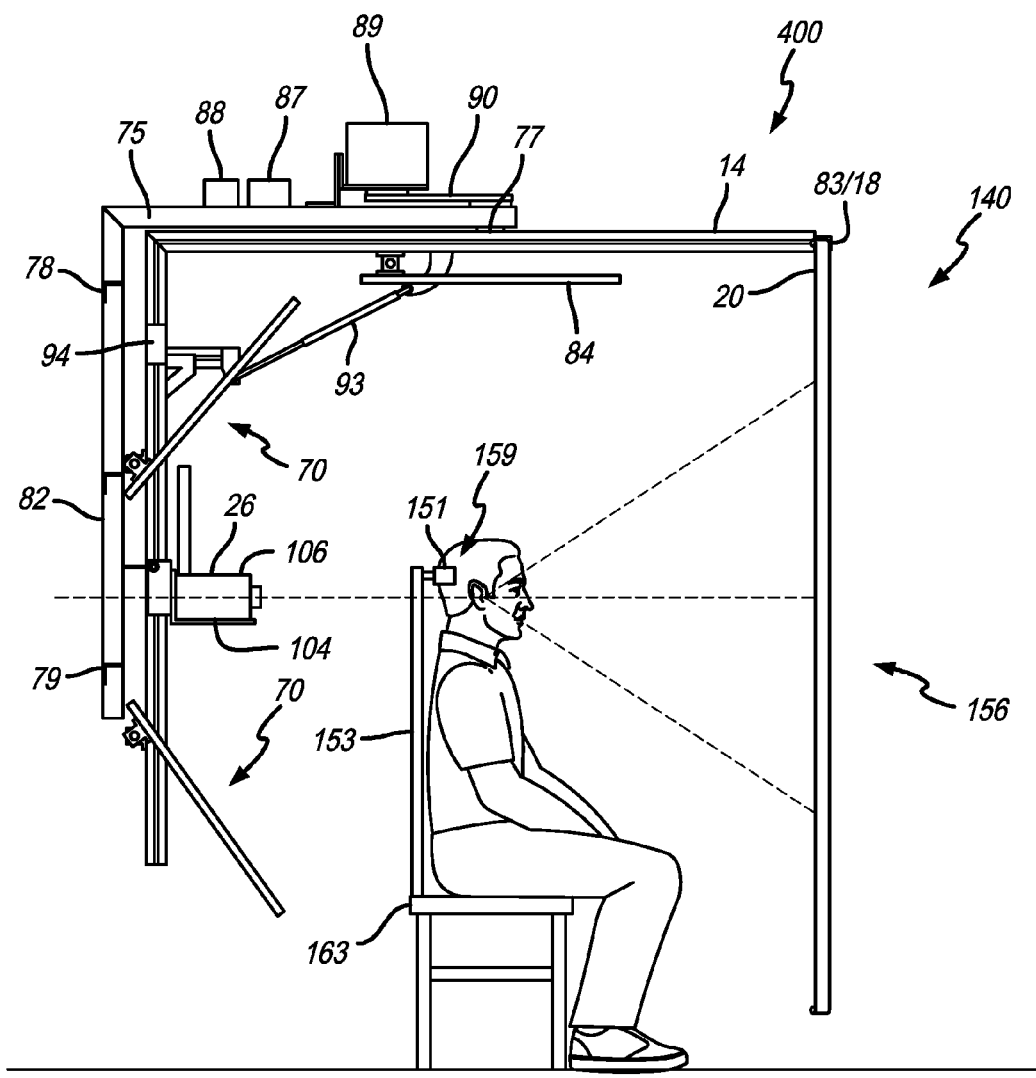
FIG. 45 is a side elevational view of the imaging system with another alignment system in accordance with a preferred embodiment of the present invention.

FIG. 45 shows another alignment system 151. Generally, the alignment system 151 is any surface (referred to herein as an alignment surface) against which the patient can rest or position their head so that before and after images are repeatable. In other words, for both the before and after scans, the patient rests his or her head against the same alignment surface 151 positioned in the same location. FIG. 45 shows an extension or back 153 extending upwardly from the seat 163 and a U-shaped member 159 that receives the patient's head. In another embodiment, the alignment system 163 can be a chair with a back 153 that includes an indentation 152 therein.

Figure 27:
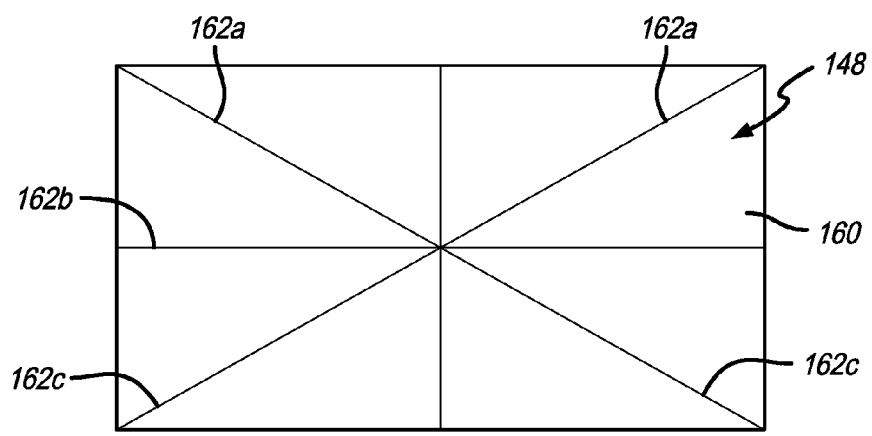
FIG. 27 shows a monitor that includes alignment markings thereon.
Figure 29:
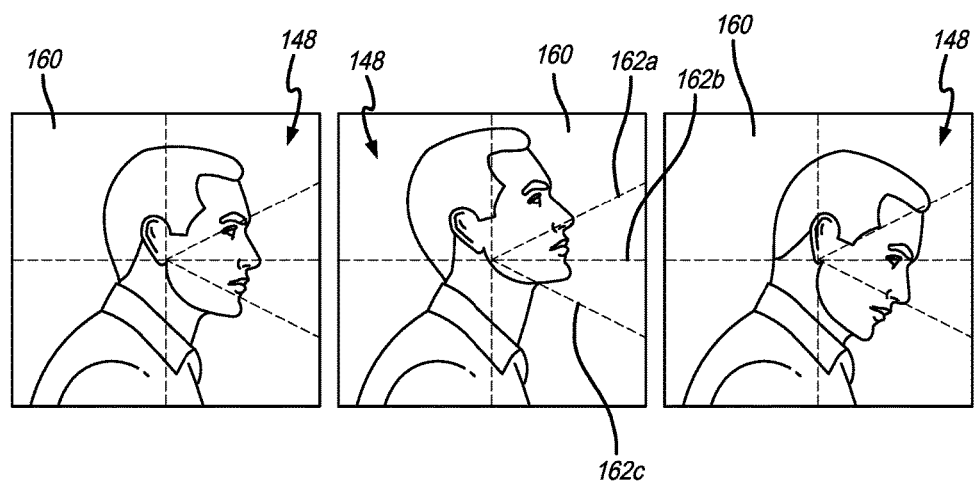
FIG. 29 shows a series of monitors with alignment markings thereon and a patient using the markings in repose, with head tilted up and head tilted down.
Figure 32:
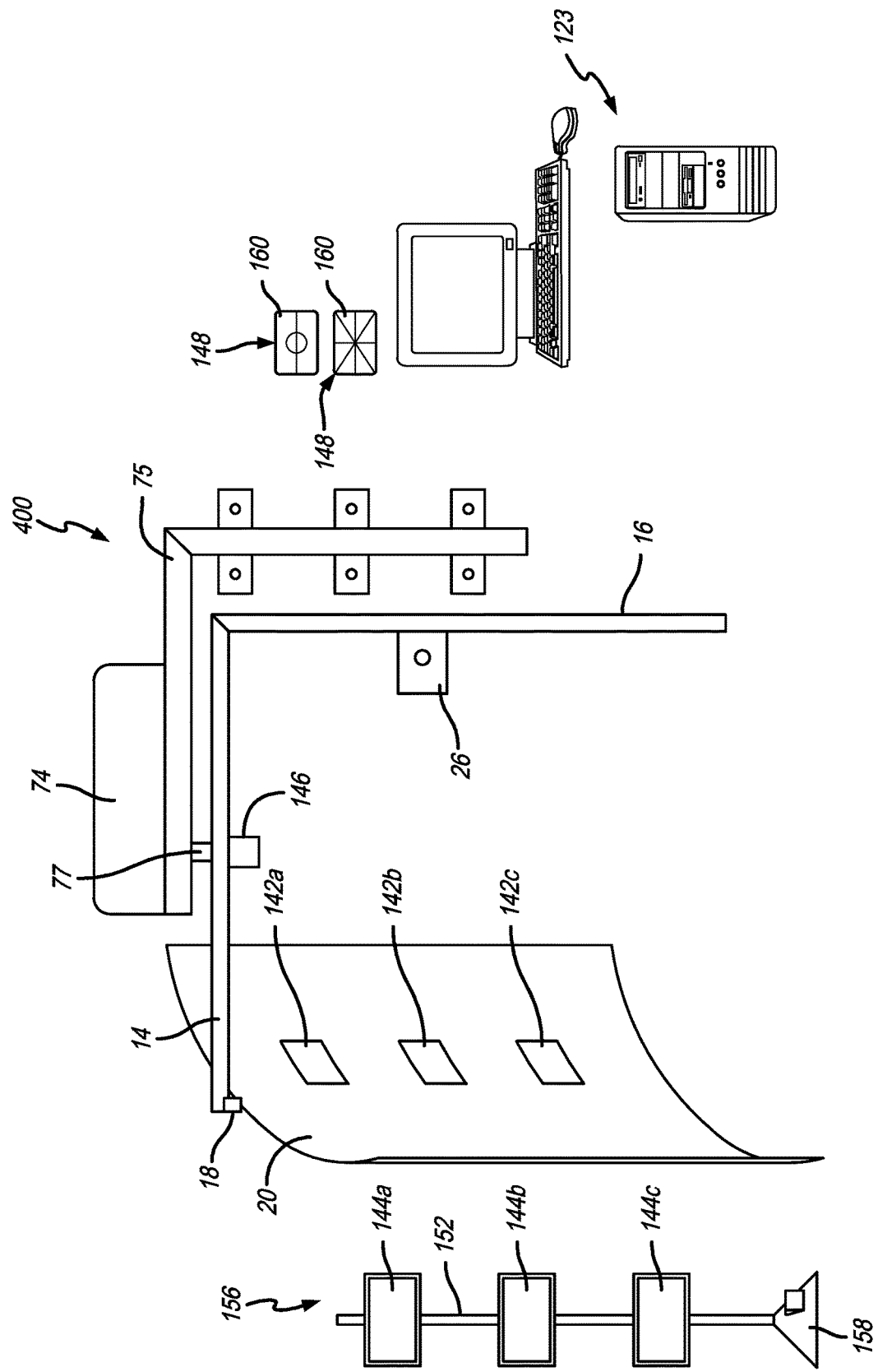
FIG. 32 is a schematic view of the components of the imaging system of FIG. 23.

As shown in FIG. 32, in a preferred embodiment, the alignment system 140 also includes at least one monitor 160 that is used by the person/technician that is performing the scan or operating the imaging system 400. This monitor 160 also includes alignment markings 148 thereon. The markings 148 can be the same as those shown in FIG. 25 or they can be those shown in FIG. 27. The markings 148 shown in FIG. 27 provide repeatability for head tilt. FIG. 29 shows an example of how the markings 148 can be used. The markings 148 preferably include a tilt up line 162a a center line 162b and a tilt down line 162c. Using these, the technician can tell the patient to, for example, tilt their chin up so that it aligns with the tilt up line 162a. By using this technique, when the patient comes back for an "after" scan, the image will match the "before" scan. The tilt up line 162a a center line 162b and a tilt down line 162c can also be provided on any of the monitors that are viewed by the patient. This way, the patient can align themselves without having to be told by the technician.

Figure 30:
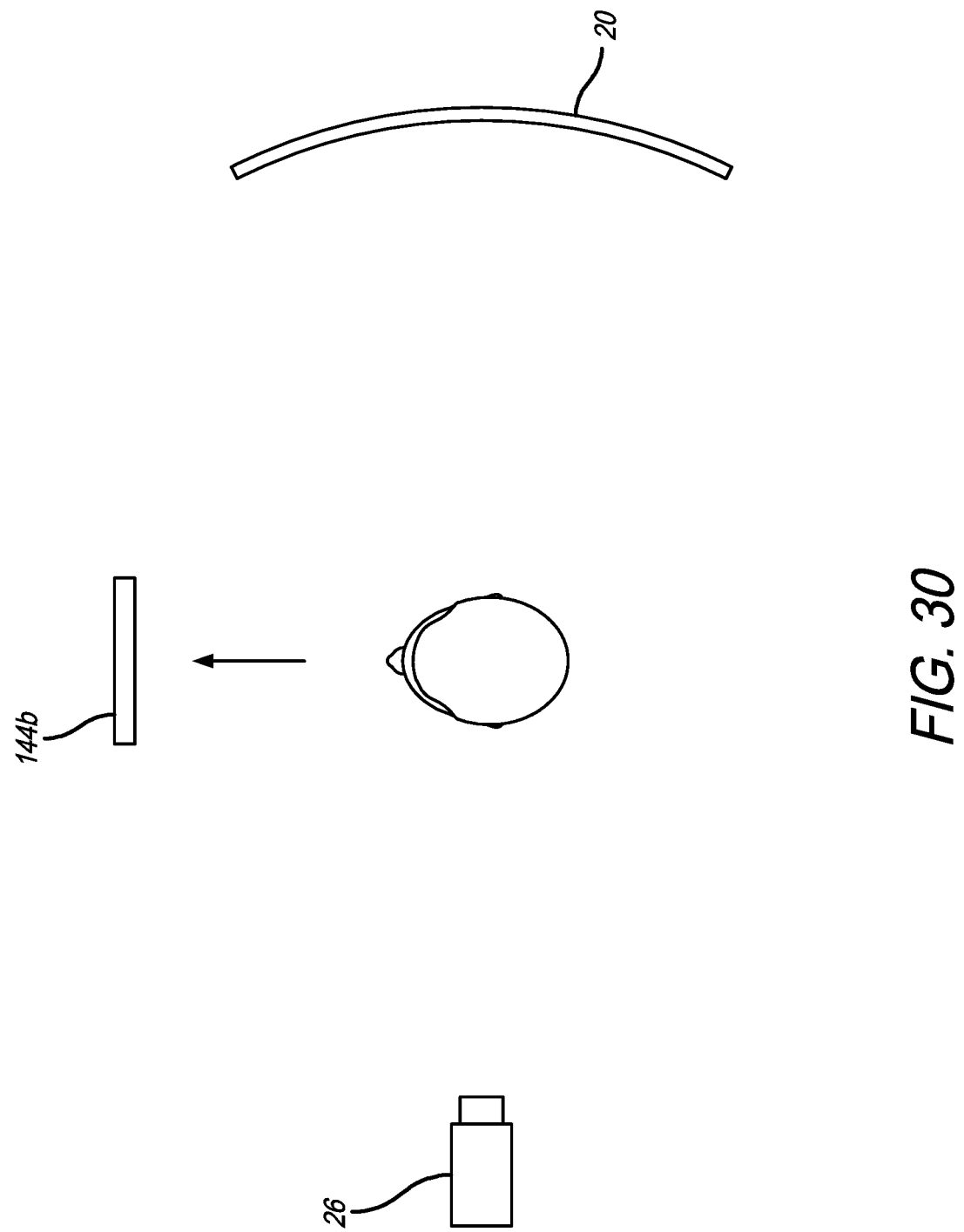
FIG. 30 is a plan view of an alignment system in accordance with a preferred embodiment of the present invention.

It will be appreciated that in order to perform the alignment using the markings shown in FIG. 27, the image must be taken from the side of the patient, as shown in FIG. 30. This can be accomplished by a separate camera that is positioned to the side of the patient (approximately 90° from the home position) or by positioning the screen 20 and imaging camera 26 such that they are on the right and left sides of the patient's head and are approximately 90 degrees from the monitor 144b viewed by the patient, as shown in FIG. 30. In a preferred embodiment, the operator's monitor 160 is part of the user interface of the system. For vertical positioning, the height is adjusted based on the operator looking at the gridlines, indicia (and particularly the horizontal line) on his screen. Alternatively, the patient can move their seat 163 up and down as desired so that their sight line is directly at the monitor.

FIG. 29 shows exemplary positioning of the patient's head for a neutral head position scan, a head tilted up scan and a head tilted down scan. As discussed, the alignment system allows repeatability for before and after scans. FIG. 29 shows alignment markings 148 with vertical 162d, horizontal 162b and upwardly extending 162a and downwardly extending 162c angled lines. The lines help provide a repeatable angle for before and after scans. 45° is not a limitation on the present invention. Any angle is within the scope of the present invention.

In an embodiment, any number of the alignment systems can be combined such that the imaging camera and screen are positioned at the sides of the patient's head, and the operator has a monitor with alignment indicia (like FIGS. 26-28), but three monitors (neutral, tilt up and tilt down) are provided for the patient. In this embodiment, both or one or the other of the patient and the operator can assist with desired alignment.

Figure 31:
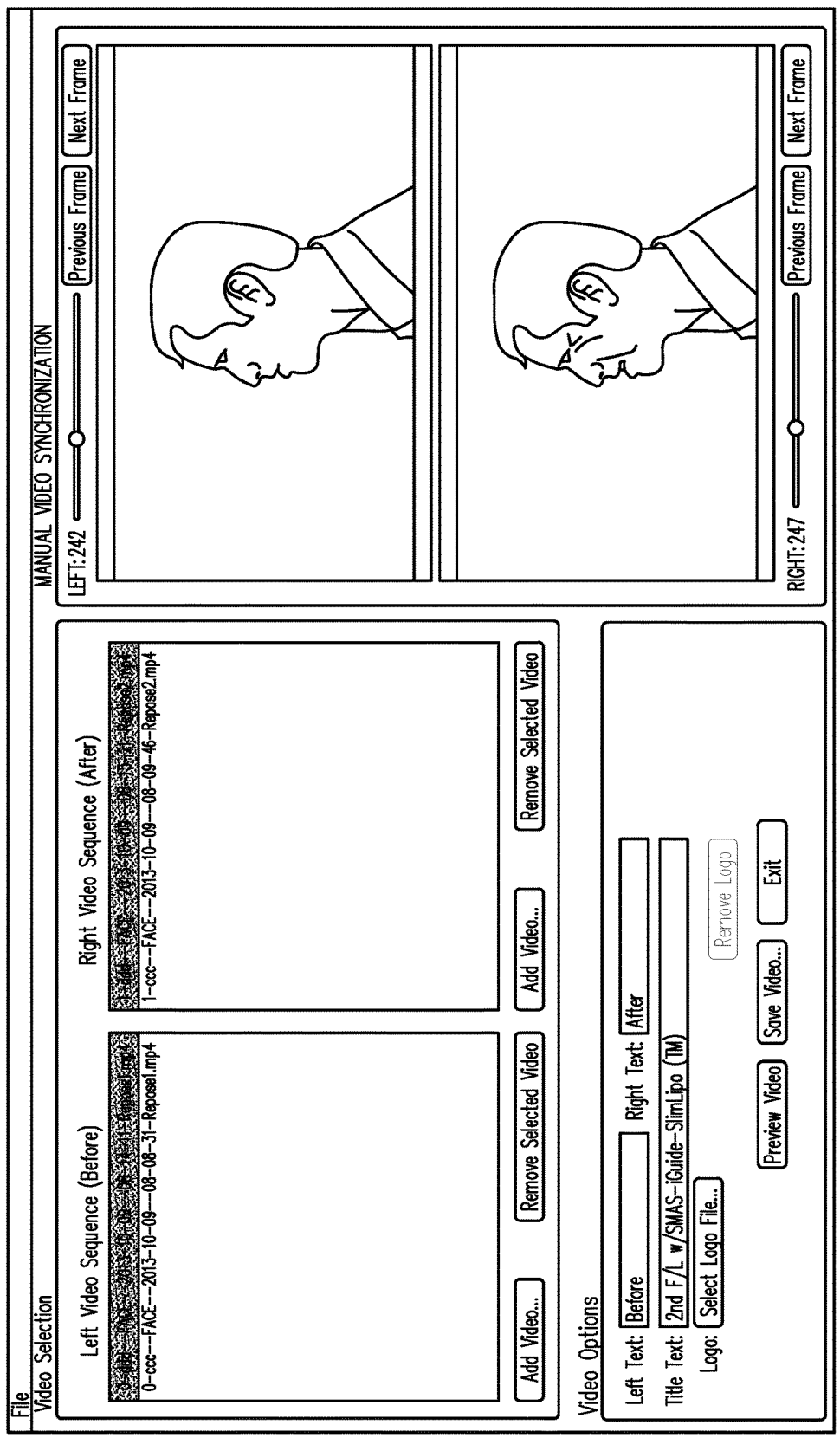
FIG. 31 is screen grab of a video capture graphical user interface.

FIG. 31 shows a screen shot of a processing screen that is part of the user interface of the imaging system and is used for manual synchronization of two videos. A slider and buttons are used to advance a single frame forward or backward to adjust both videos so they can be set to the same starting point relative to some feature of the patient's face. In a preferred embodiment, the starting point is the point at which the nose becomes visible from behind as the head rotates around. However, this is not a limitation and any starting point can be used. The user can preview the synchronized before-and-after video and adjust one or both of the individual videos accordingly until the desired level of synchronization is reached.

Figure 33:
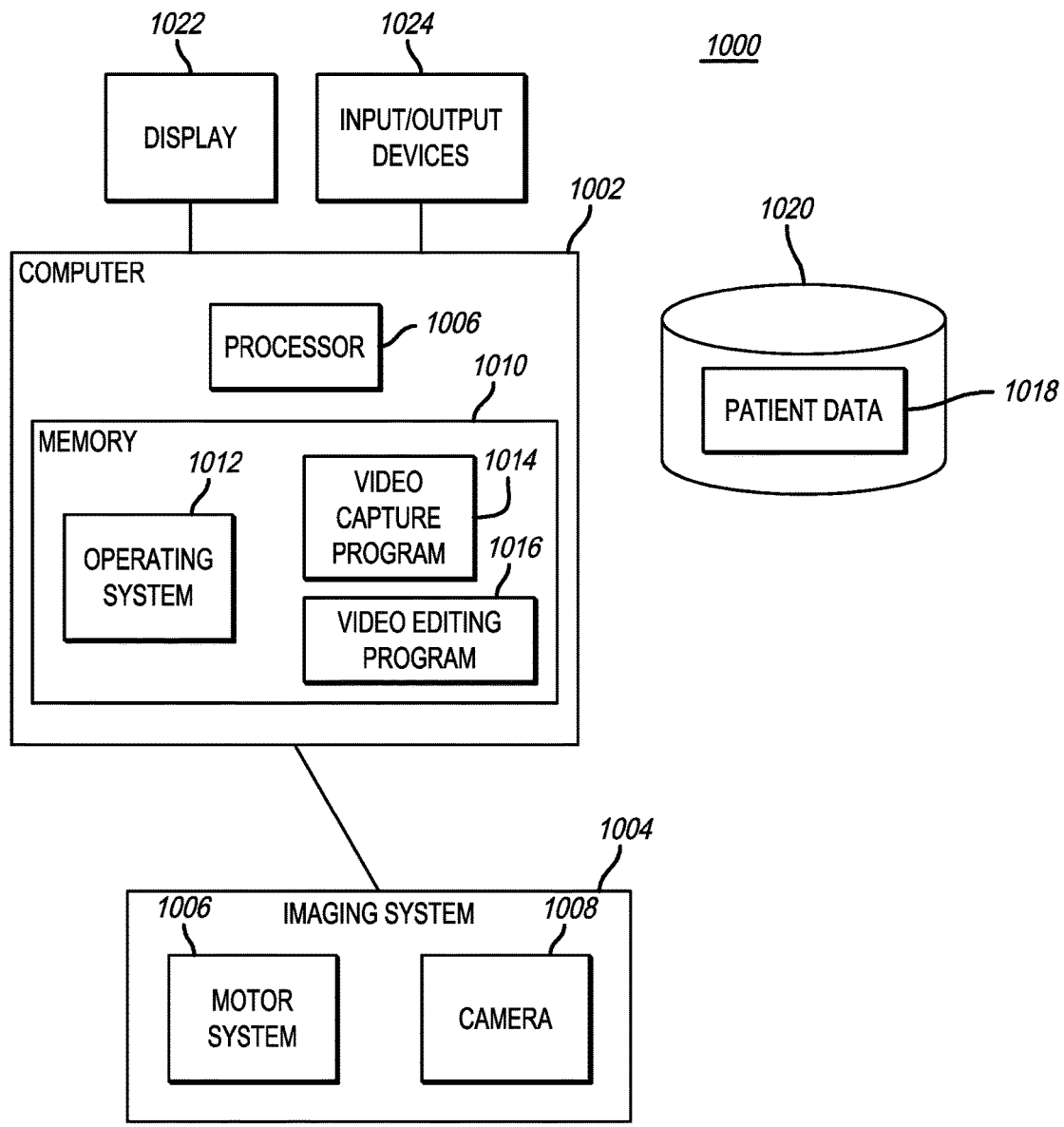
FIG. 33 illustrates an embodiment of a computing environment in which descried embodiments may be implemented.

FIG. 33 illustrates an embodiment of a computing environment 1000 that is integrated with the above imaging systems, including the system 400 shown in FIG. 23, to initiate video capture operations and perform video editing operations to generate a new video, referred to herein as a merged video, that combines the video images from two different videos taken at different times to allow for before and after comparison of the same views of the subject, which may be a patient that has undergone a medical procedure or treatment.

A merged video plays in the same frames the content from different before and after videos shot by the camera at different times to allow the two before and after views in the same pose to rotate at the same time to allow the doctor and patient to have a complete view of the before and after results of the medical procedure, such as cosmetic surgery, other surgical procedures, and other medical treatments, such as drug therapy, weight loss, physical therapy, etc. Although certain embodiments are described with respect to merging videos of a patient in a same pose before and after a surgical procedure, the videos subject to being merged according to the processes described herein may be of any content or subject, animate or inanimate, where comparison of the one or more subjects rendered in different videos is desired.

FIGS. 33-43 show a computing environment 1000 that includes a computer 1002 that is coupled to the components in an imaging system 1004, such as the imaging systems described above, e.g., 400 in FIG. 23. The computer 1000 may issue commands to control a motor system 1006 in the imaging system 1004, such as the motor systems described above, e.g. motor system 74 in FIG. 23, to cause the rotation of the camera 1008 (e.g., camera 26) along a path around the patient positioned in the imaging system 1004. The camera 1008 generates a video image comprising a sequence of frames generated according to video formats known in the art.

The computer 1002 includes a processor 1006, such as a microprocessor, virtual processor, etc., and a memory 1010, such as an electronic memory device (e.g., DRAM, RAM, flash memory, etc.) or virtual memory, having program code executed by the processor 1006. The program code includes an operating system 1012, a video capture program 1014, and a video editing program 1016. The computer 1002 may comprise a server, workstation, desktop computer, virtual machine, laptop, tablet, smartphone, and other computing devices known in the art. The video capture 1014 and video editing 1016 programs may create video images for subjects, e.g., patients, positioned in the imaging system 1004 and store the video images with patient data 1018 in a storage device 1020.

The storage device 1020 may comprise a non-volatile storage device, such as are implemented may comprise hard disk drives, solid state drives (SSD) comprised of solid state electronics, such as a EEPROM (Electrically Erasable Programmable Read-Only Memory), flash memory, flash disk, Random Access Memory (RAM) drive, storage-class memory (SCM), etc., magnetic storage disk, optical disk.

A display monitor 1022 maybe coupled to the computer 1002 to render video display out. Input/Output devices 1024 coupled to the computer 1002, such as a keyboard, mouse, microphone, touch screen, and other input devices.

Figure 34:
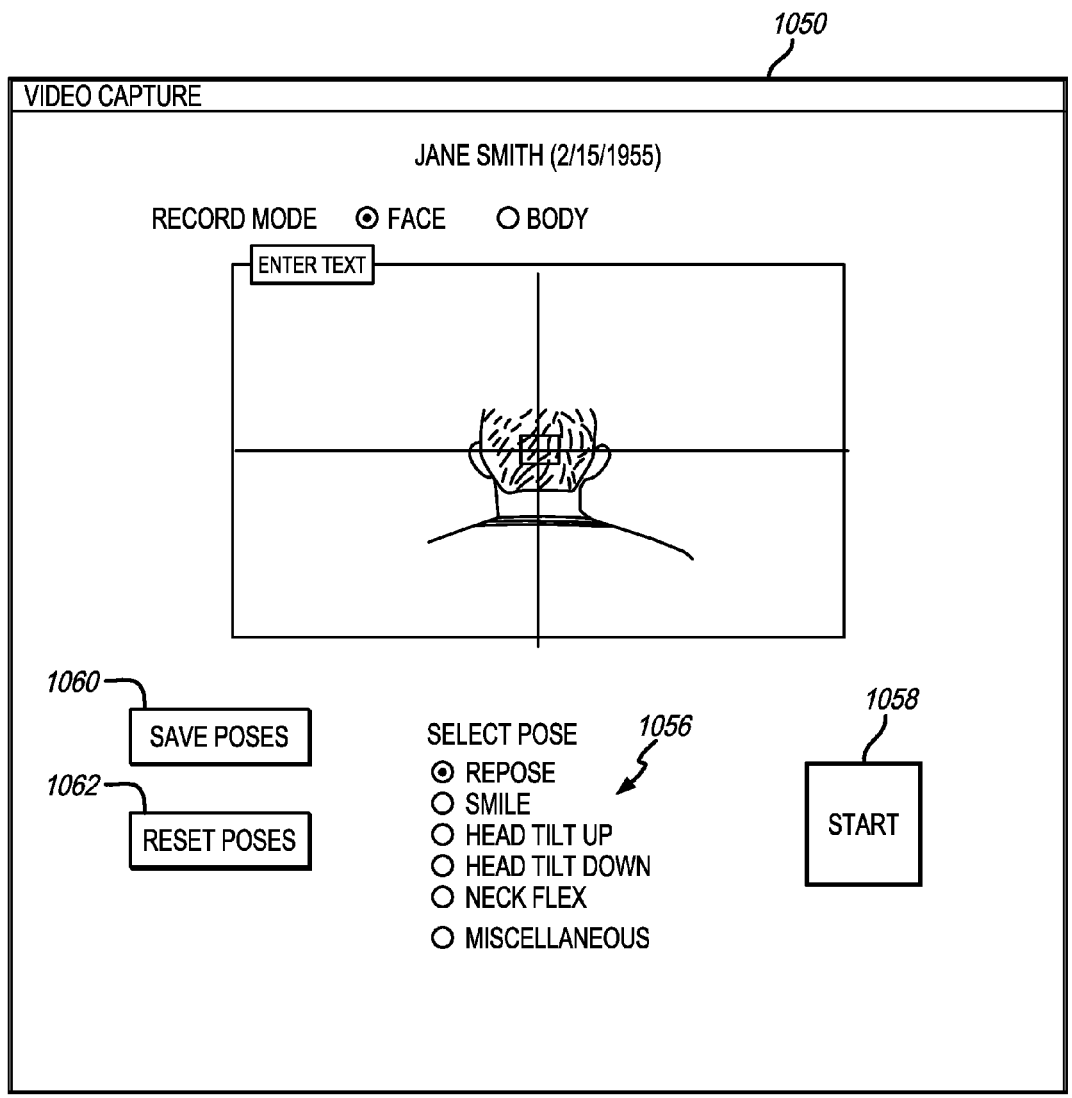
FIG. 34 illustrates an embodiment of a video capture graphical user interface.

FIG. 34 illustrates an embodiment of a video capture graphical user interface (GUI) 1050 the video capture program 1014 renders on the display 1022. The GUI 1050 has a video capture panel 1052 showing the view transmitted from the camera 1008, which in FIG. 34 shows a back of the head of the patient. The operator of the imaging system 1004 may have the patient adjust their position so that a focal point of the camera 1008 view, represented by the cross hair 1054, is at a predetermined position with respect to the patient's body. The operator may have the patient adjust their position in the imaging system 1004 so that the cross hair 1054 is positioned at a desired point. Alternatively, the operator may adjust the camera 1008 manually or through the video capture program 1014.

In the GUI 1050, the operator may select a pose that is to be captured by selecting one of the displayed poses 1056, including, but not limited to a repose, smile, head tilt up, head tilt down, and neck flex. For repose, the operator will have the patient look straight, no smile, and mouth slightly open and position the cross hair 1054 at the patient's eye level. For a smile pose, the operator will want the patient to show teeth and make sure that the cross hair 1054 is at the patient's eye level. For a head tilt up pose, the operator will have the patient pose chin up, eyes looking straight upward and position the cross hair 1054 at a top of the nose. For a head down pose, the operator will have the patient pose chin down, eyes looking straight down towards bottom screen and the cross hair 1054 at a top of nose. For a band stretch pose, the operator will have the patient stretch and relax neck muscles screen and position the cross hair 1054 at a top of nose.

After having the patient adjust their position according to the selected pose, the operator may select a start button 1058 to cause the motor system 1006 to rotate the video camera 1008 around the patient, such as described with respect to FIG. 23 and other embodiments to create a video image as the video camera 1008 rotates around the patient. After the operator has recorded a video image for a desired number of selected poses 1056, the operator may select the save poses 1060 control to save all the captured videos for one or more poses for the patient in the storage 1020 or select a reset poses 1062 to erase any captured videos during the current session, beginning when the user started capturing images since the last video images were saved or reset.

Figure 35:
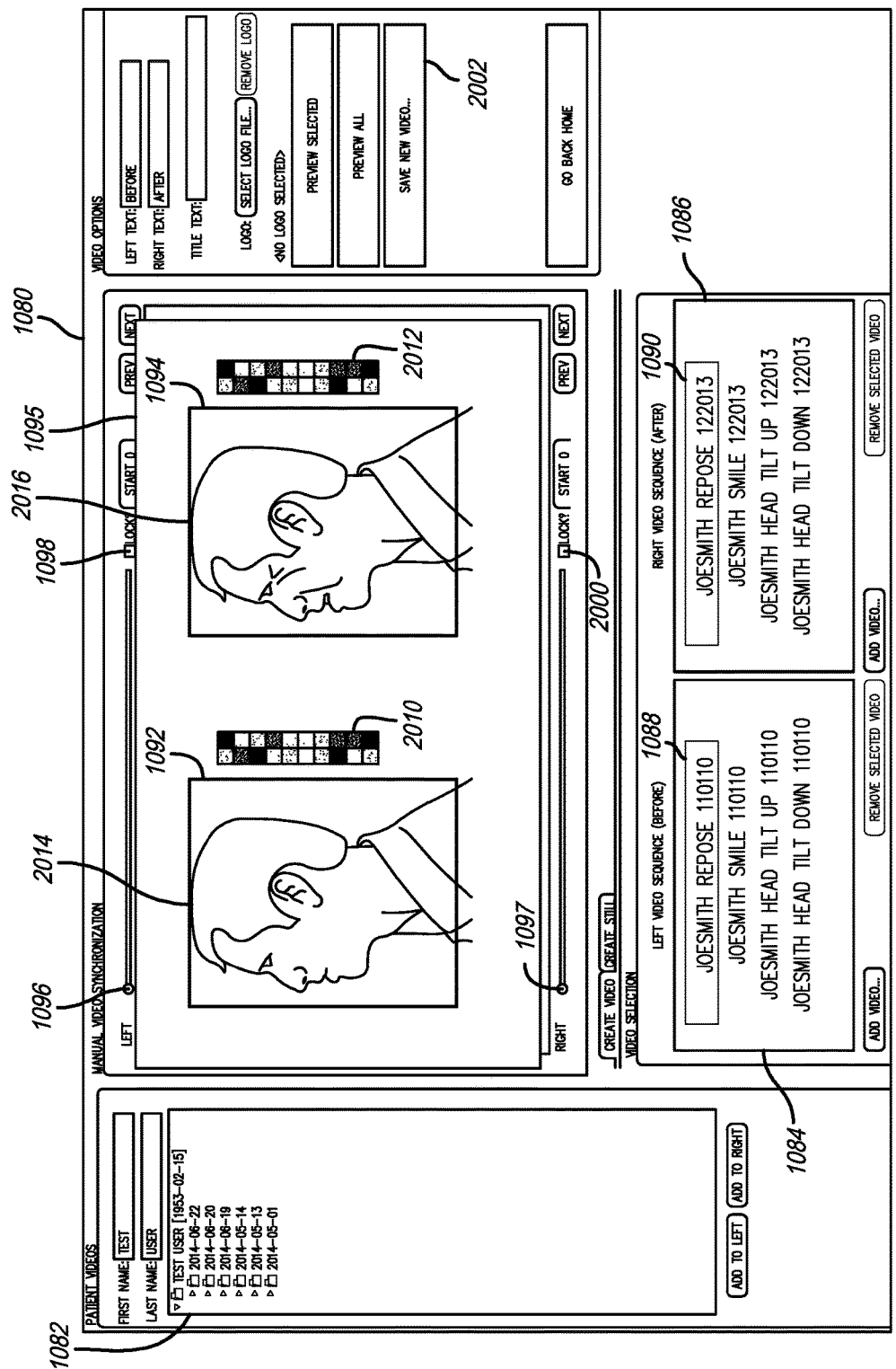
FIG. 35 illustrates an embodiment of a video editing graphical user interface.

FIG. 35 illustrates an embodiment of a GUI 1080 the video editing program 1016 renders on the display 1022 to enable the operator to select videos for the patient taken at different times to merge the views of the selected videos into a single video. The GUI 1080 has a file selection panel 1082 displaying folders having different sets of video images of poses of the patient taken at different times, e.g., dates. Upon expanding one of the folders for one date, the operator may select one or more video images for that date for a first panel 1084, which may be used for selecting the before videos. The operator may then select video images from another of the folders for a later date in the file selection panel 1082 for a second panel 1086, which may be used for selecting the after videos.

Within the first 1084 and second 1086 panels, the user may select a video for one of the poses from the different sets of videos for the different selected times. FIG. 35 shows the repose pose selected 1088, 1090 in the before 1084 and after 1086 panels. Upon selecting a video for one of the poses from each of the first 1084 and second 1086 panels, the GUI 1080 may then display a first 1092 and second 1094 video players in a merge video panel 1095 in which the selected videos 1088, 1090 may be independently and simultaneously controlled to play. These two video images may then be combined into a single merged video image that has frames with the pose from the two selected video images 1088, 1090.

In certain embodiments, the videos 1088, 1090 may be captured with a color chart 2010, 2012 that is positioned in proximity to the subject during image capturing. The color charts 2010, 2012 appearing in the captured videos 1080, 1090 may comprise a Macbeth color chart that is used for color calibration of the video images during the video editing operations, as described below. Further, the video players 1092 and 1094 may display an outline 2014 and 2016, respectively, showing where the image will be cropped during editing so as to remove the color charts 2010, 2012 from the video frames.

The GUI further renders first (left) scroll controls 1096 and second 1097 (right) scroll controls to allow the user to scroll through the frames of the video image 1088 displayed in the first video player 1092 and through the frames of the video image 1090 displayed in the second video player 1094, respectively. The scroll controls 1096 and 1097 enable the user to independently scroll through the frames of the rendered video images 1088, 1090. The operator may use the scroll controls 1096 and 1097 to select frames at which to start forming the first (before) and second (after) views in the final merged video image. The operator may use the scroll controls 1096 and 1097 if the position of the patient in the different video images 1088, 1090 is not the same for the same number frames in the sequence. In other words, given the patient's position, the angle of the patient view may be different in the same numbered frames in the sequences. Scrolling allows the user to select different starting frames so that the patient's position matches at the starting frames in the two different video images 1088, 1090 so the merged frames have the patient at substantially similar angles and perspective of view in each merged frame. The user may also scroll through the video images to select a starting frame as a preferred starting point for the merged video.

Upon reaching a desired point for the starting frames, the operator may select the lock control 1098 and 2000 to select a starting frame at which to start combining frames. If the user does not select a starting frame, then the first frame is used as a default. Other scroll controls to scroll through the selected videos 1088, 1090, such as the previous ("PREV") and next ("NEXT") buttons provide another mechanism for scrolling. Upon saving the selected views, such as selecting the save control 2002, the merged frames are formed from the content from the different selected videos 1088, 1090. This final merged video image allows the user to play the video image to show each of the images 1092 and 1094 of the patient to rotate next to each other in the merged video image.

FIGS. 36-39 illustrate operations performed by the video capture program 1014 to capture vides of a patient in different poses. FIG. 36 illustrates an embodiment of operations performed by the video capture program 1014 to start the capture process. Upon initiating (at block 2020) video capture operations in response to activating the video capture program 1014, the video capture program 1014 generates (at bock 2022) a folder in a file system of the operating system 1012 having a name identifying the patient, or other subject, and a date, such as the folders shown in panel 1082 of FIG. 35. The video capture program 1014 generates (at block 2024) the video capture graphical user interface (GUI) 1050 to display on the display monitor 1024 a video capture panel 1052 providing a transmitted view captured by the video camera, a graphical element 1054 that shows a focal point of the video camera positioned on a subject to be filmed, and information on selectable poses 1056.

FIG. 37 illustrates an embodiment of operations performed by the video capture program 1014 to capture the video from the video camera 1008. Upon receiving (at block 2040) operator selection to capture the raw video, such as by selecting the start button 1058, the video capture program 1014 sends (at block 2042) one or more commands to control the motor system 1006 to direct the video camera 1008 along a predefined path around the patient or subject positioned with respect to the focal point (cross hairs 1044) to capture a video image filmed along the path by the video camera 1008. The path of the camera 1008 as controlled by the motor system 1006 may rotate around the patient centered at the focal point for a predefined number of degrees of rotation, e.g., greater than 360 degrees, may move toward the patient, move away from the patient; and/or move vertically up or down with respect to the patient. The path may be determined by the motor system 1006 or the video capture program 1014.

A folder is generated (at block 2044) in a file system for the patient identifying the date or time period of a current video session, such as the folders displayed in panel 1082. The video capture program 1014 names (at block 2046) the captured video image in the current session with a name identifying the pose associated with the video image and other information, such as the patient name and date. Each named video image, comprising the raw captured video, is saved (at block 2048) in the storage 1020 and the named video image indicated in the file system as included in the generated folder. As mentioned, the captured raw video may include color charts 2010, 2012 placed near the patient so they are captured in the video image and available for use during video editing for color calibration.

In the embodiment of FIG. 37, patient video images are associated with a patient using file names and the hierarchical file system by organizing video image files for a patient in a patient folder and date folders to identify video images created on a particular date. In an alternative embodiment, video images and information on the video images, such as the pose, date taken, etc., may be associated with a patient by using a database or content management system.

Figure 38:
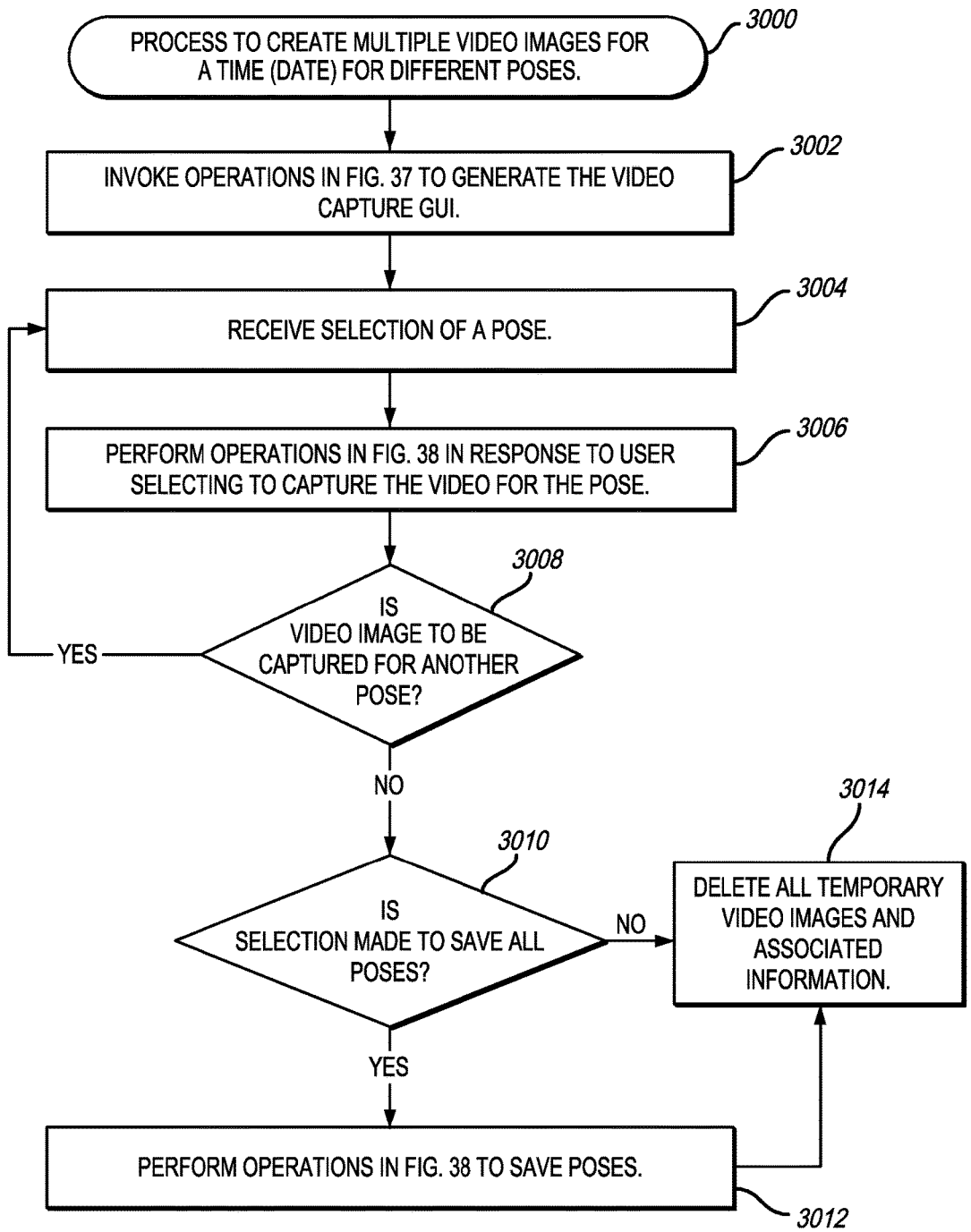

FIG. 38 illustrates an embodiment of operations to capture multiple sets of videos for different poses. The operations of FIG. 38 may be initiated on different dates to create sets of video images at different times that may be used for before and after comparisons of the patient in different poses. The operations of FIG. 38 to use the video capture program 1014 may be initiated by an operator of the program 1014 or the program 1014 itself, or a combination of the operator and program 1014. Upon initiating (at block 3000) the process to create a set of video images for different poses for a session or date, the operations in FIG. 36 may be invoked (at block 3002) to generate the video capture GUI 1050. If the operations of FIG. 38 are performed only by the video capture program 1014, then the GUI 1050 may not be generated because the video capture program 1014 may initiate operations without the use of the GUI 1050. Upon receiving (at block 3004) selection of a pose (through controls 1056 if the GUI 1050 is used), the video capture program 1014 is invoked (at block 3006) to perform the operations of FIG. 38 to control the imaging system 1004 to capture a video image for the selected pose.

If (at block 3008) a determination is made to capture a video image for another pose (by the operator or program 1014) in the current session, then control returns to block 3004. If (at block 3008) no more poses are to be filmed, upon selection (at block 3008) to save the poses, the video capture program 1014 (at block 3010) performs (at block 3012) the operations in FIG. 37. After saving (at block 3012) the set of video images for that session/date or if selection is made (from the no branch of block 3008) to not save the video images captured for the current, which the operator can indicate by selecting the reset poses 1062 graphical control, then the video capture program 1014 may delete (at block 3014) all temporary video images and associated information generated for that session.

After generating the sets of video images of poses for the patients on different dates, the operator may use the video editing program 1016 to create merged video images that combine the content of video images taken on different dates for the same pose in a single video images where the video and frames of that pose on the different dates can be compared. This allows the patient and doctor to compare how the patient appeared in the pose before and after the medical procedure or therapy. FIGS. 39-42 provide embodiments of operations to generate a merged video image that merges content taken from different video images on taken different dates.

Figure 39:
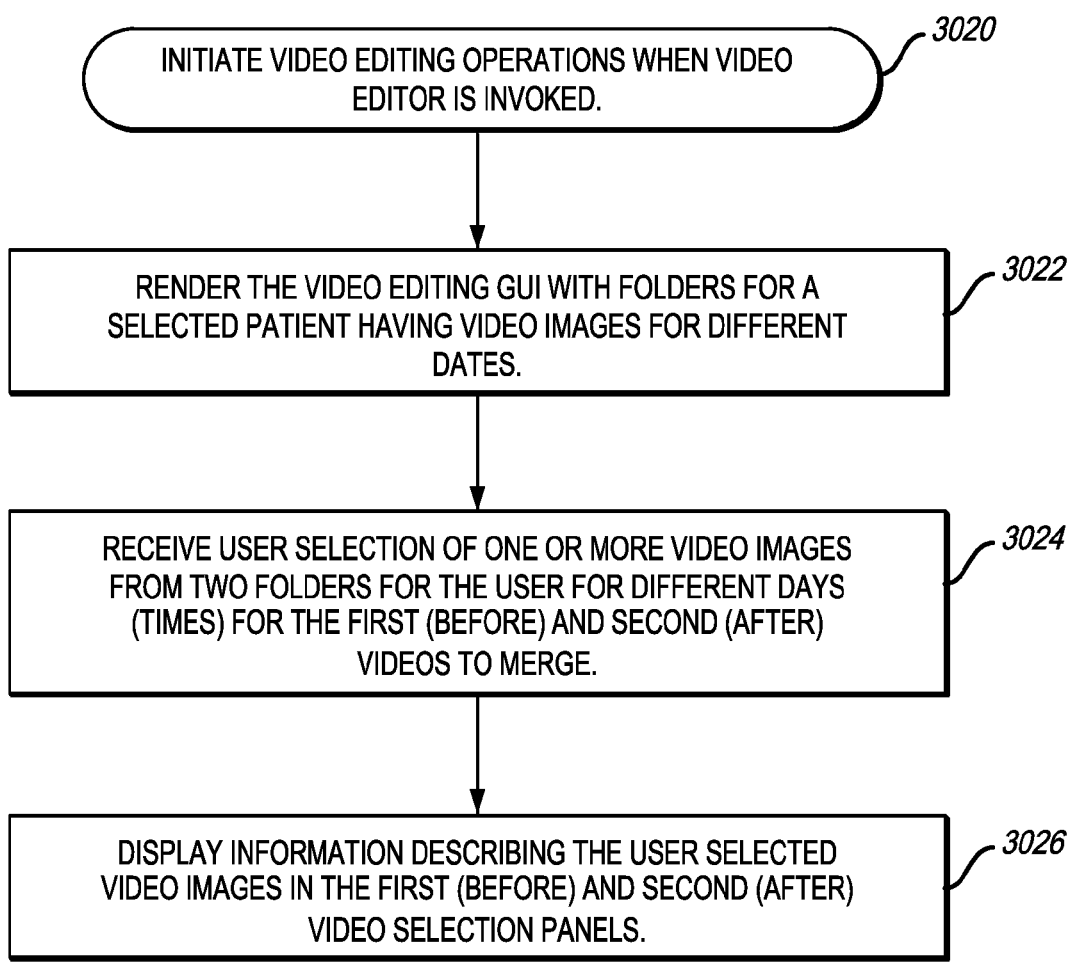

With respect to FIG. 39, upon being invoked (at block 3020), by the operator or a program, the video editor program 1016 renders (at block 3022) the video editing GUI 1080 having the file selection panel 1082 rendering folders for a selected patient having sets of video images for different poses for different dates. The video editor program 1016 receives (at block 3024) through the video editing GUI 1080 user selection from the file selection panel 1082 of one or more video images from two folders for the patient for different days (times) for the first (before) and second (after) video images to merge together. The video editor program 1016 displays (at block 3026) information describing the user selected video images in the first (before) 1084 and second (after) 1086 video selection panels. The displayed information may comprise a description of the content of the video image, such as patient name, pose and date, a file name, etc.

In certain embodiments, the operator selects video images for a same pose taken on different dates to combine the content of a same pose taken before and after a medical procedure. However, the operator may select different combinations of video images for a patient to combine in a merged video image, such as video images for different poses on a same or different date or video images for a same pose on a same or different dates, and the dates of the selected images may be for before the medial surgery or after. Further, in certain embodiments, two video images are selected to combine their content in a merged video image. In an additional embodiment, more than two video images may be selected to combine the content or view of a pose of a patient from more than two video images into the merged video image.

Figure 41A:
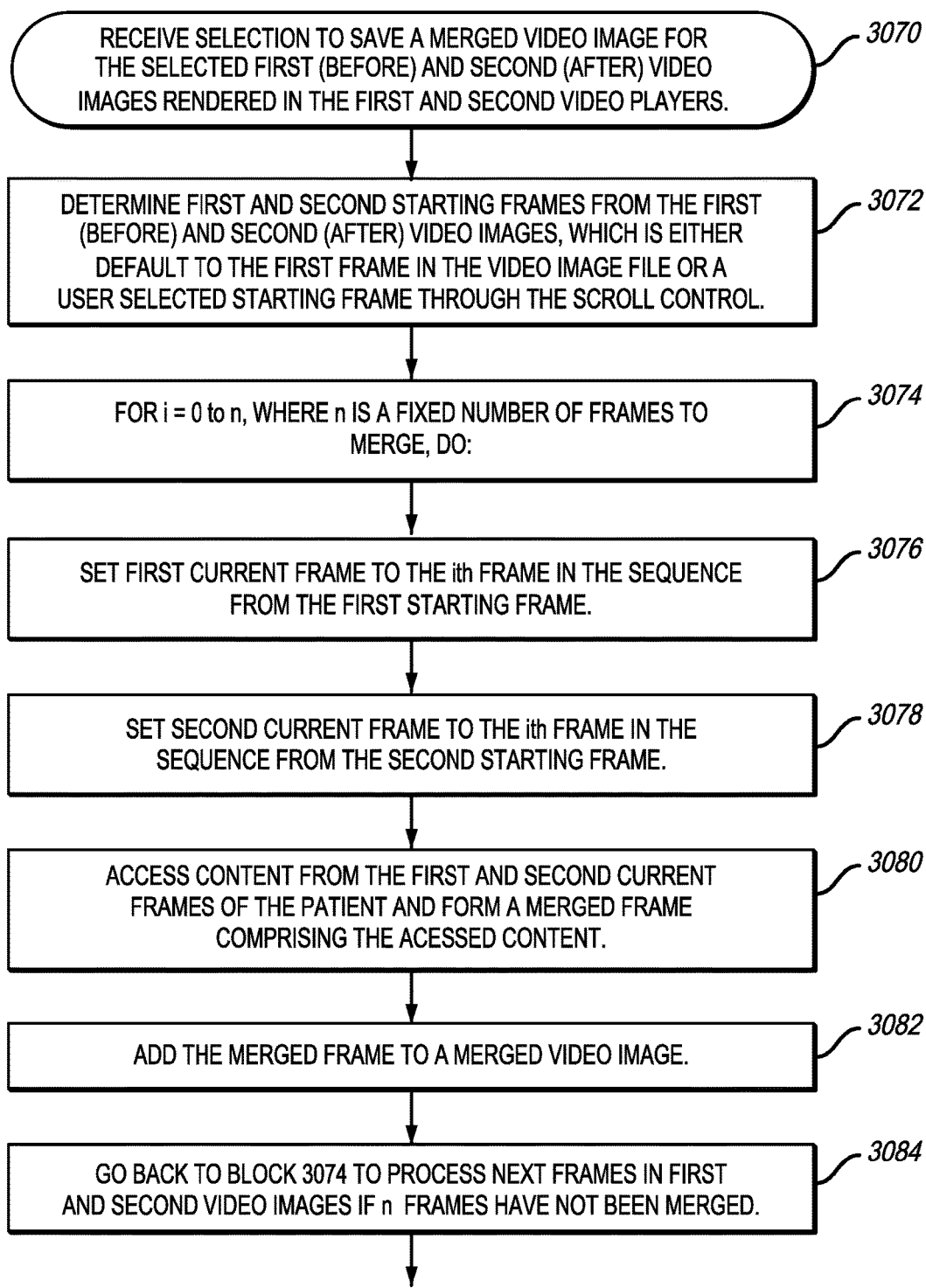
Figure 41B:
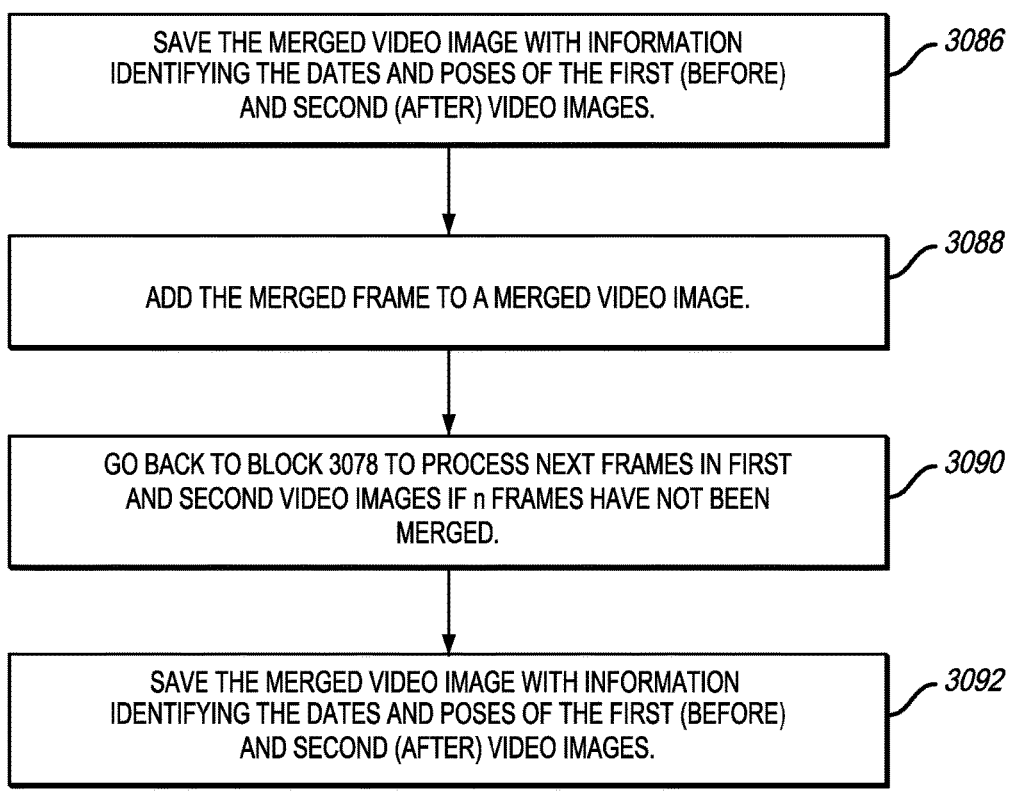

FIG. 41 illustrates an embodiment of operations performed by the video editor program 1016 to prepare user selected video images from the panels 1084 and 1086 for merging. After populating the panels 1084 and 1086 with one or more before and after video images for different poses, the video editing GUI 1080 may receive (at block 3040) user selection of a video image from each of the first (before) 1084 and (second) after 1086 video selection panels. FIG. 35 shows video images 1088 and 1090 selected for a "repose" pose for different dates in the before 1084 and after 1086 panels, respectively. The video editing program 1016 renders (at block 3042) in the merge video panel 1095 (FIG. 36) a first video player window 1092 to render the selected video image 1088 from the first panel 1084 and a second video player window 1094 to render the selected video image 1090 from the second panel 1086. Initially upon selection, the first frame in the sequence of frames from each of the selected first 1088 and second 1090 video images is rendered in the first 1092 and second 1094 video player windows, respectively.

The video editing GUI 1080 further renders (at block 3044) graphical controls, such as the scroll bars 1096 and 1098 and, PREV and NEXT buttons, to enable the user to simultaneously and independently control the play of the first 1088 and second 1090 videos. The controls may comprise the user selecting the video players 1092 and 1094 or comprise a graphical element. The GUI 1080 renders (at block 3046) the first selectable scroll control 1096 to enable the user to scroll through the frames of the before video 1088 rendered in the first video player window 1092 and a second selectable scroll control 1097 to enable the user to scroll through the frames of the after video 1090 rendered in the second video player window 1094. The GUI 1080 further renders (at block 3048) a first and second lock controls 1098 and 2000 to enable the user to select the starting frames for the first 1088 and second 1090 video images.

FIG. 41 illustrates an embodiment of operations performed by the video editing program 1016 to form the merged video image from the selected first (before) 1088 and second (after) 1090 video images. Upon receiving (at block 3070) selection, by the operator or program 1016, to save a merged video image for the selected first (before) 1088 and second (after) 1090 video images rendered in the first 1092 and second 1094 video players, the video editing program 1016 determines (at block 3072) first and second starting frames from the first (before) 1088 and second (after) 1090 video images. The starting frames may comprise either a default first frame in the sequence of frames in the video image file 1088, 1090 or a user selected starting frame the user selected through the scroll 1096, 1097 and lock 1098, 200 controls.

If the selected video images 1088, 1090 include color charts 2010, 2012, then in certain embodiments, the video editing program 1016 may perform (at block 3074), for each of the first 1088 and second 1090 videos, a color calibration of all the frames based on the color chart included in the frames resulting in color corrected first and second vides. For instance, the video editing program 1016 may invoke a color calibration process to calibrate all the frames based on the colors presented in the color charts 2010, 2012 using video editing tools such as used in SPEEDGRADE® by ADOBE®, that are capable of color calibrating all video frames using a color chart in one or more of the video frames to synchronize the calibration across all of the frames of the video. (SPEEDGRADE and ADOBE are registered trademarks of Adobe Corporation in the United States and other countries). For each of the color corrected first and second videos, the video editing program 1016 may crop (at bock 3076) the content in the frame, as shown by the cropping region 2014 and 2016 in FIG. 36 to remove the color charts 2010, 2012 from the frames of the first 1088 and second 1090 videos, respectively.

The video editing program 1016 performs a loop of operations at blocks 3078 through 3090 to merge a fixed number of frames from the first 1088 and second 1090 video images. The fixed number of frames to merge may be predetermined in the video editing program 1016 or based upon predefined or user entered settings. For instance, if the merged video image is to provide a 360 degree view of the patient pose, then a number of frames may be selected based on the camera 1008 film speed and or frame capture rate and the rate of rotation of the camera 1008 by the motor system 1006, where the fixed number is the number of frames needed to capture the desired degree of rotation, such as 360 degrees. The video capture program 1014 may capture more than the desired degree of rotation to allow for adjustment of the starting point. Thus, if a video is typically created for a desired 360 degree of rotation, then more than that, such as frames for 420 degrees of rotation, is captured so that during editing the program 1016 may select the fixed number of frames to merge for the desired degree of ration when the starting frames are at an offset from the first captured frame in the sequences.

The loop of operations at blocks 3078 and 3090 is performed for i=0 to n, where n is the fixed number of frames to merge to obtain the desired degree of rotation in the merged video. The variable "n" may be less than the total number of frames captured in the video images 1088, 1090. The video editing program 1016 sets (at block 3080) a first current frame to the ith frame in the sequence of frames from the determined first starting frame and sets (at block 3082)

the second current frame to the ith frame in the sequence from the second starting frame. The video editing program accesses (at block 3084) content from the set first and second current frames of the patient or subject, and forms (at block 3086) a merged frame comprising the accessed content from the different video images 1088, 1090. The accessed content may comprise the color calibrated frames that are cropped to remove the color charts 2010, 2012 from the frames. In an embodiment that does not perform color calibration, the operations at blocks 3074 and 3076 may not be performed. In merging the content, the video editing program 1016 may juxtapose the content from the different video images side-by-side, stacked on top of each other, superimposed, etc., to allow comparison of the content from the different video images 1088, 1090 in the merged frame. The merged frame is then added (at block 3088) to the merged video image, as either the first frame if i equals zero or following the last added (i−1)th frame if i is greater than zero. After adding the fixed number (n) of merged frames to the merged video image file, the merged video image is saved (at block) in the storage 1020 with information identifying the dates, poses, and patient of the first (before) 1088 and second (after) 1090 video images.

FIG. 42 illustrates an embodiment of operations to merge video images for multiple different poses taken before and after an event, such as a medical procedure. The operations of FIG. 42 to use the video editing program 1016 may be initiated by an operator of the program 1016 or the program 1016 itself, or a combination of the operator and program 1016. Upon initiating (at block 400) the process to merge multiple video images from first (before) and second (after) sets of video images for first and second times (dates) in the first 1084 and second 1086 video panels, the video editing program 1016 performs (at block 4002) the operations in FIG. 39 to generate the video editing GUI to receive from the operator selection of selection of first (before) and second (after) video images from the first and second sets in the file selection panel 1082 to render lists of selected first and second video images in the first 1084 and second 1086 panels, respectively. If the process is performed by the video editing program 1016, then the operation at block 4002 may not be performed to render the GUI 1080 because the selection of video images to merge may be made by the program 1016 executing code.

If the operator is using the GUI 1080, then the operations in FIG. 40 are performed (at block 4004) when the video editing program 1016 receives from the GUI 1080 selection of first and second video images from the first and second sets displayed in the first (before) 1084 and second (after) 1086 panels to render in the first 1092 and second 1094 video players in the merge video panel 1095. If the process is performed by the video editing program 1016, then the operation at block 4004 may not be performed to render selected video images 1088, 1090 in the merge video panel 1095 because the selection of video images to merge may be made by the program 1016 executing code.

In response (at block 4006) to selection, by the operator selecting the save control 2002 in the GUI 1080 or the video editing program 1016, to save the merged video for the selected pose captured in the selected first 1088 and second 1090 video images, the video editing program performs the operations in FIG. 41 to generate and save the merged video. If (at block 4000) there are further pairs of video images to merge, such as before and after video images for the same or different poses, then control proceeds back to block 4004 to form further merged video images.

In the described operations, of FIGS. 36-42, operations described as performed by the operator to make selections using one of the GUIs 1050, 1080 may instead be performed by the programs 1014 and 1016 by executing program code and making function calls.

The described operations of the video capture program 1014 and video editing program 1014 may be implemented as a method, apparatus or computer readable storage medium using standard programming and/or engineering techniques to produce software, firmware, hardware, or any combination thereof. The described operations may be implemented as code or logic maintained in a "computer readable storage medium", which may directly execute the functions or where a processor may read and execute the code from the computer storage readable medium. The computer readable storage medium includes at least one of electronic circuitry, storage materials, inorganic materials, organic materials, biological materials, a casing, a housing, a coating, and hardware. A computer readable storage medium may comprise, but is not limited to, a magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs, DRAMs, SRAMs, Flash Memory, firmware, programmable logic, etc.), Solid State Devices (SSD), etc. The computer readable storage medium may further comprise digital logic implemented in a hardware device (e.g., an integrated circuit chip, a programmable logic device, a Programmable Gate Array (PGA), field-programmable gate array (FPGA), Application Specific Integrated Circuit (ASIC), etc.). Still further, the code implementing the described operations may be implemented in "transmission signals", where transmission signals may propagate through space or through a transmission media, such as an optical fiber, copper wire, etc. The transmission signals in which the code or logic is encoded may further comprise a wireless signal, satellite transmission, radio waves, infrared signals, Bluetooth, etc. The program code embedded on a computer readable storage medium may be transmitted as transmission signals from a transmitting station or computer to a receiving station or computer. A computer readable storage medium is not comprised solely of transmission signals, but includes tangible components, such as hardware elements. Those skilled in the art will recognize that many modifications may be made to this configuration without departing from the scope of the present invention, and that the article of manufacture may comprise suitable information bearing medium known in the art.

Figure 46:
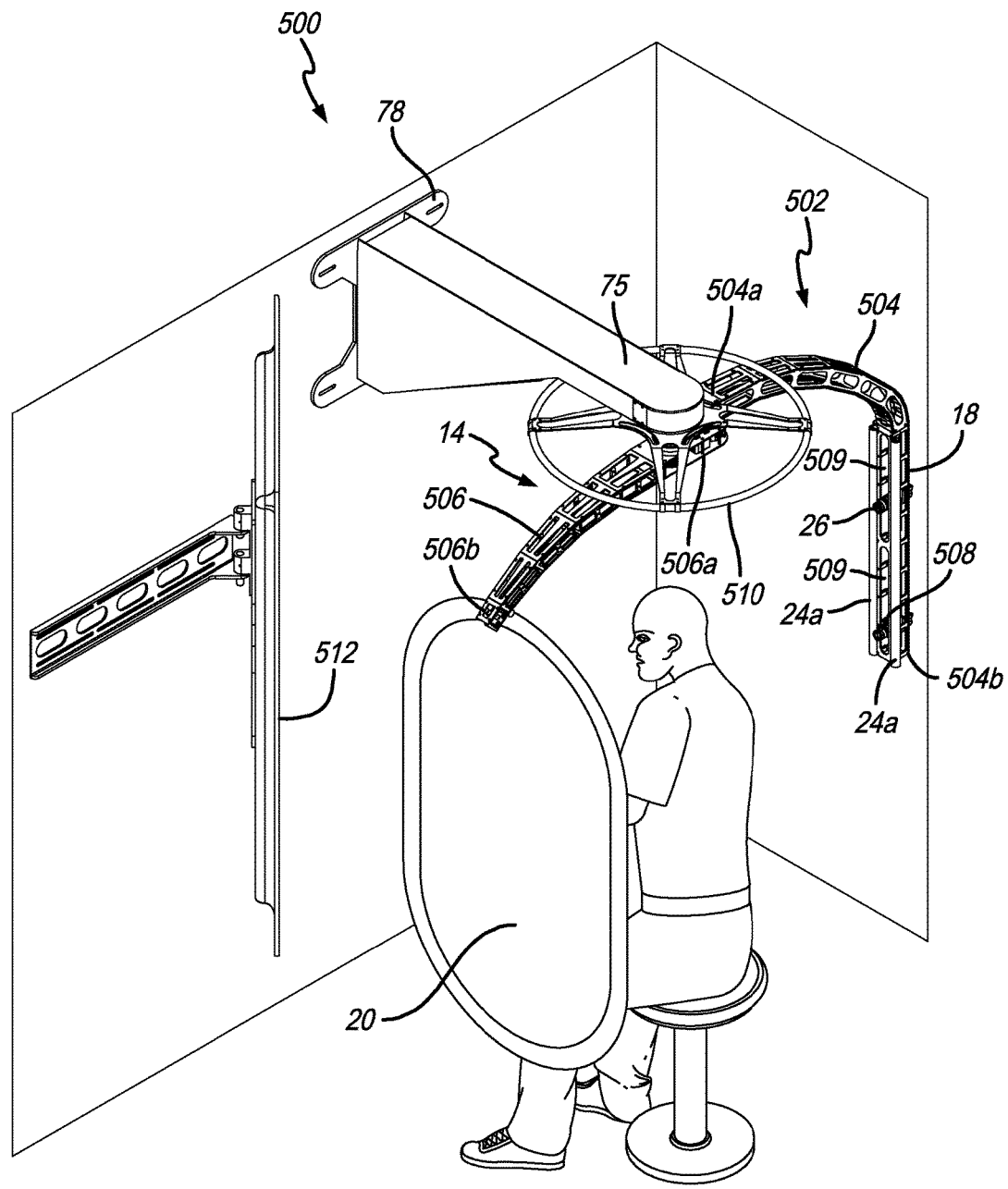
FIG. 46 is a perspective view of a rotatable imaging system showing the rotating unit during rotation in accordance with another preferred embodiment of the present invention.
Figure 47:
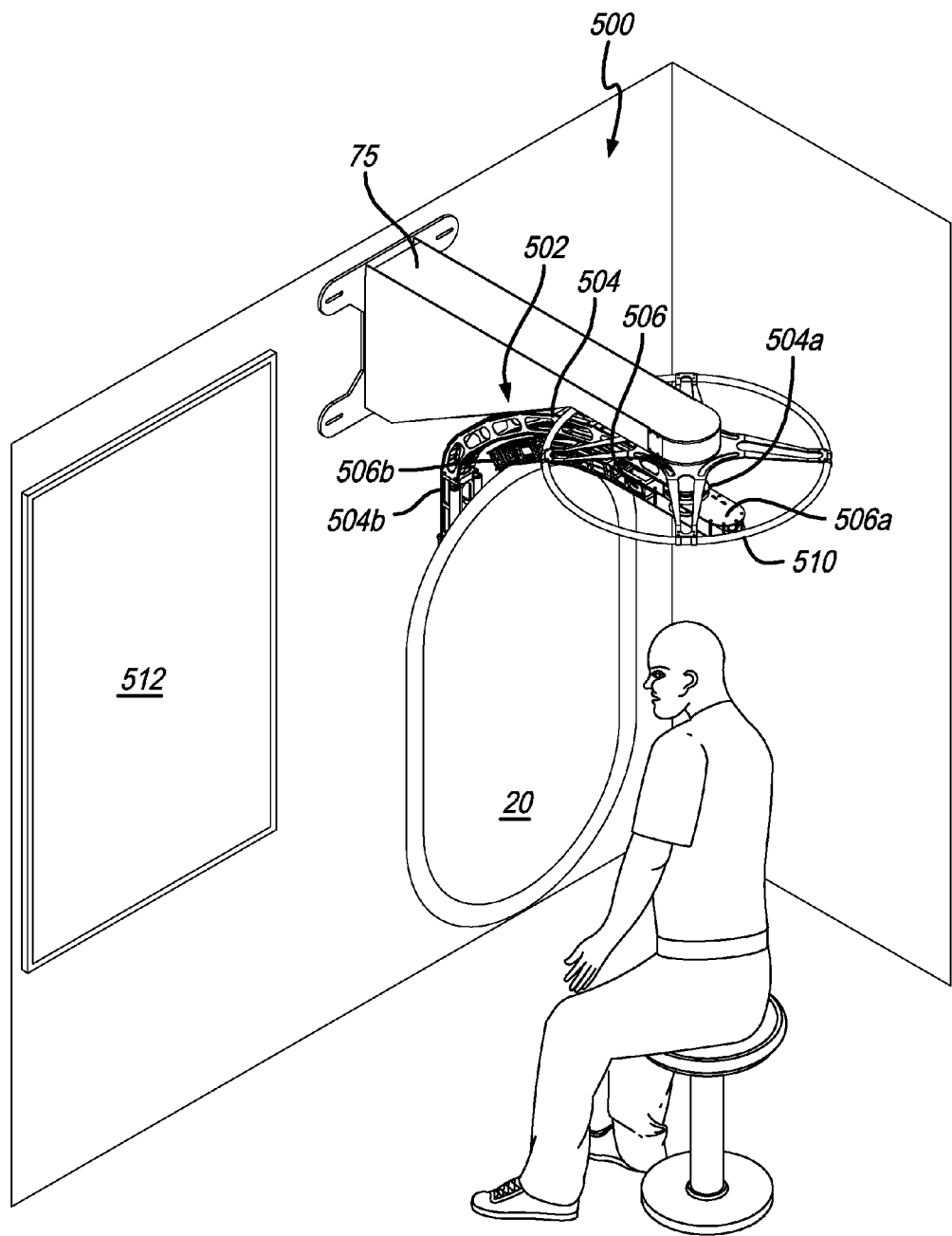
FIG. 47 is a perspective view of the rotatable imaging system of FIG. 46 with the rotating unit in the stowed position.

FIGS. 46-50 show another embodiment of a rotatable imaging system 500. The system 500 operates similarly to the imaging systems described above. However, the rotating unit 502 of the system 500 includes a first portion 504 and a second portion 506 that allow the rotating unit 502 to be stowed, as shown in FIG. 47. The first portion 504 and the second portion 506 together form the horizontally oriented boom 14 that rotates about the rotation axis with the imaging camera 26 on one side and the backdrop/screen 20 on the other side. In other words, the rotatable pivot extends through both the first portion and the second portion 504 and 506. It will be appreciated that the horizontally oriented boom 14 is not necessarily completely horizontal (as the first and second portions are curved), but is referred to herein as horizontal because the boom 14 rotates about a vertically oriented axis.

The first portion 504 and the second portion 506 each have a proximal end 504a and 506a through which the rotation axis extends and a distal end 504b and 506b that is positioned away from the rotation axis. The imaging camera 26 is associated with the distal end 504*b* of the first portion 504 and the backdrop 20 is associated with the distal end 506*b* of the second portion 506. The backdrop 20 can be flat or curved. Preferably, the first vertical arm 16 extends downwardly from the distal end 506*b* of the second portion 506. A second imaging camera 508 can be included. In a preferred embodiment, both of the imaging cameras are adjustable vertically. In the embodiment shown in the figures the imaging cameras 26 and 508 are positioned in slots 509 that allow the cameras to be adjustable vertically. Preferably, lights 24*a* are positioned on opposite sides of the imaging cameras. In a preferred embodiment, the system 500 also includes a light ring 510 that is coaxial with the rotation axis and provides downward lighting for lighting the subject.

As shown in FIG. 46, the system 500 includes a horizontal boom 75 having a first end that is secured to the wall or another vertically oriented object (see, e.g., FIGS. 56-57) and a second end to which the rotating unit 502 is rotatably attached. In a preferred embodiment, the components for rotating the rotating unit 502 (e.g., the motor control unit, computer components, motor, cooling fan, etc.) are housed within, connected to or shrouded by the horizontal boom 75.

As shown in FIG. 47, the first portion 504 and the second portion 506 are rotatable to and from a stowed position where the first portion 504 and the second portion 506 are in substantial vertical alignment. In other words, the second portion 506 is located vertically under the first portion 504 or vice versa. It will be appreciated by those of ordinary skill in the art that the imaging camera 26 and backdrop 20 both move along a 360° rotation path. In the stowed position, the distal ends of the first and the second portion And a home position where the distal ends of the first and second portions 504 and 506 are located at approximately the same position along the rotation path. In the stowed position, the first portion 504 and the second portion 506 are preferably in substantial vertical alignment with the horizontal boom 75. In another embodiment, the horizontal boom 75 can include a rotatable pivot at the end connected to the wall or other vertical object so that it can be stowed against the wall (similar to the embodiment shown in FIGS. 18-19).

Figure 48:
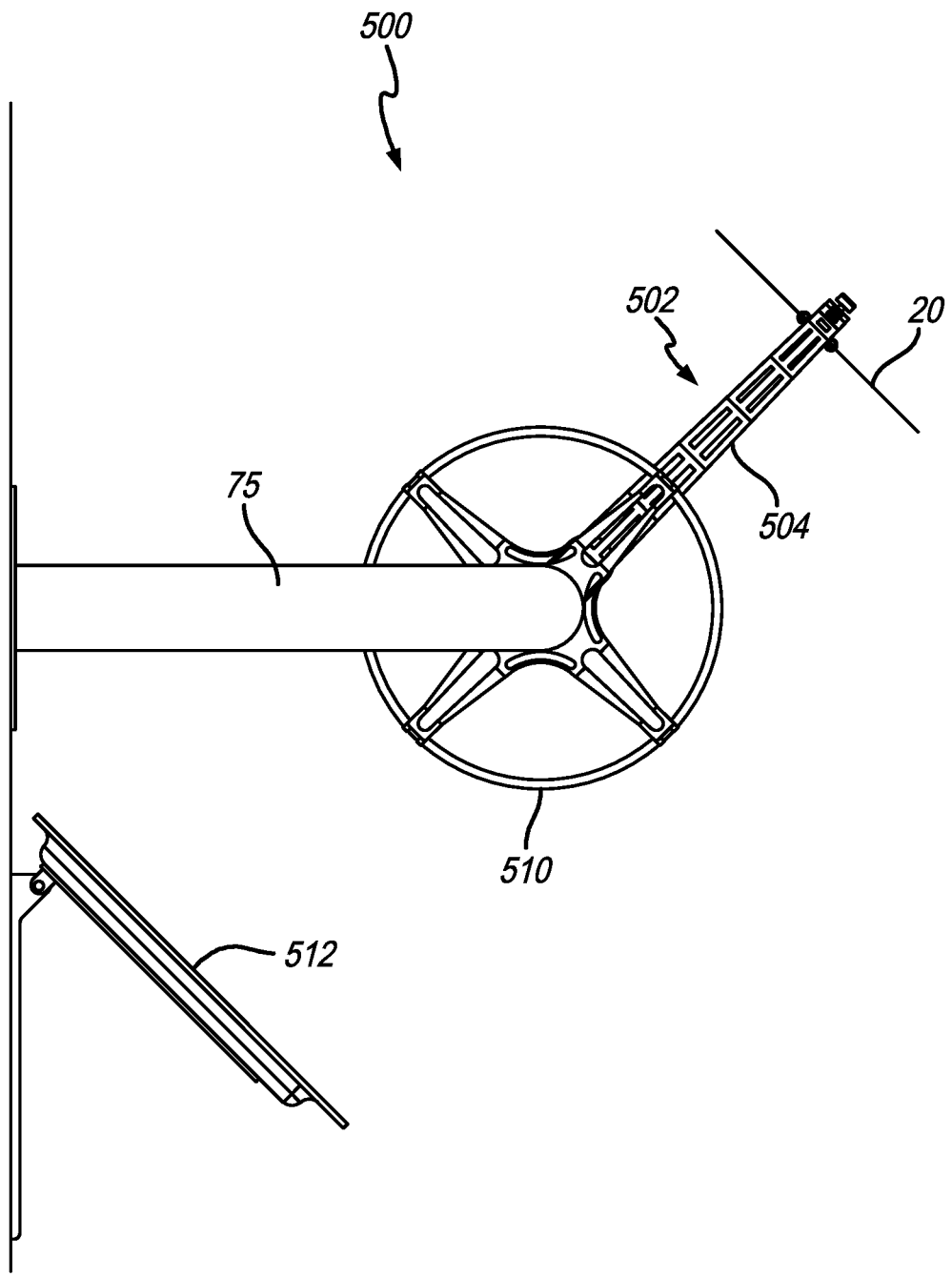
FIG. 48 is a top plan view of the rotatable imaging system of FIG. 46 with the first portion and the second portion rotated together to an intermediate position.
Figure 49:
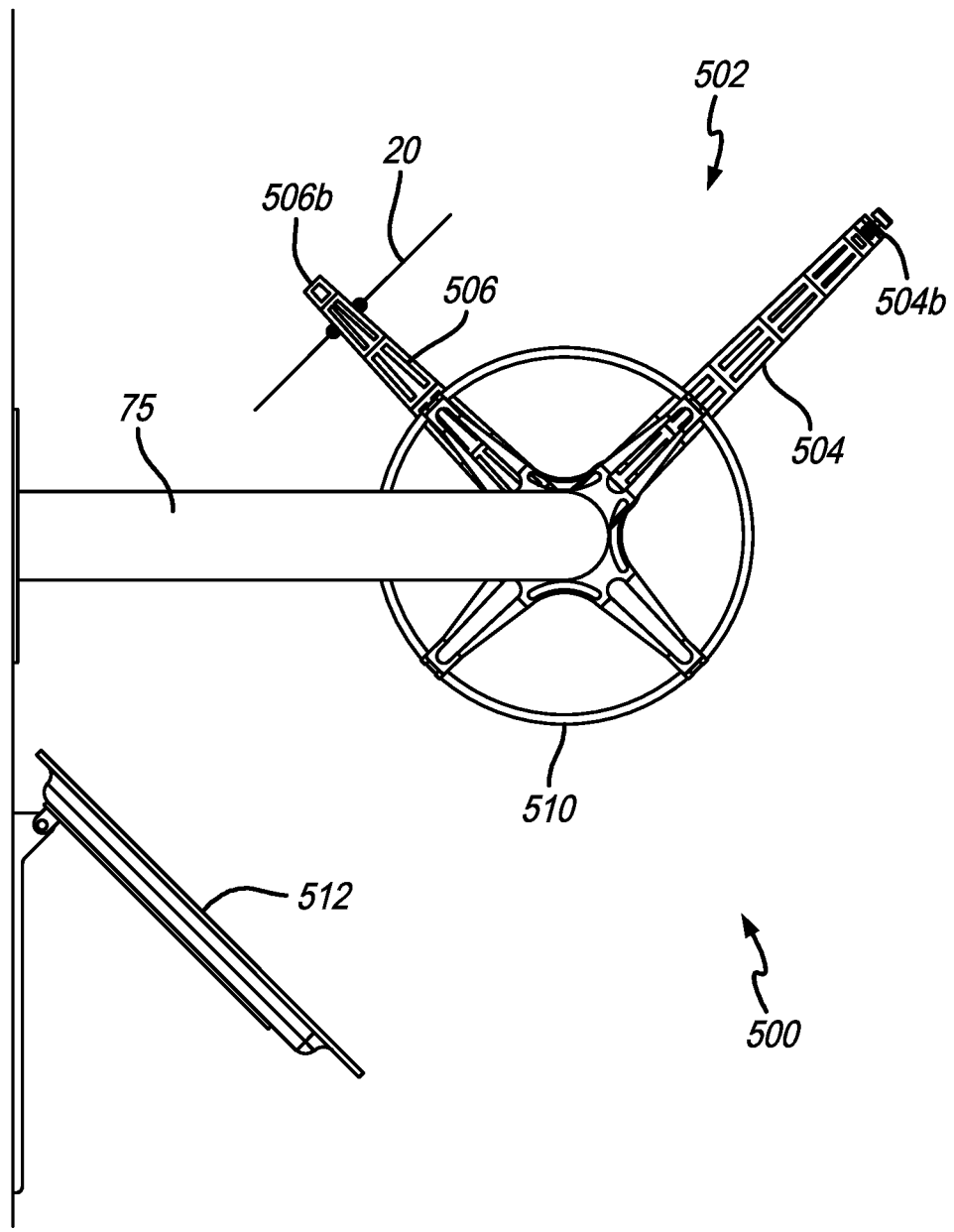
FIG. 49 is a top plan view of the rotatable imaging system of FIG. 46 with the first portion and the second portion in an alignment position.

When the system 500 is to be used, the first and second portions 504 and 506 are rotated to the home position so that a scan can be taken. As shown in FIG. 48, the first and second portions 504 and 506 (and the entire rotating unit 502) rotate together until the first portion 504 is in the home position (referred to herein as the intermediate position). FIG. 49 shows the first and second portions 504 and 506 (and the entire rotating unit 502) in an alignment position where the second portion 506 has rotated separately from the first portion 504, which is still in the home position. As shown, the second portion 506 forms and approximately 90° angle with the first portion. In this position, the subject is able to view the alignment image taken by the overhead alignment camera 146 (see FIG. 23 or FIG. 58) on the alignment monitor 512. In another embodiment, the alignment position can be the position where the first and second portions 504 and 506 overlap, as is shown in FIG. 48. Any position that allows the subject to review the alignment monitor 512 is within the scope of the invention.

Figure 50:
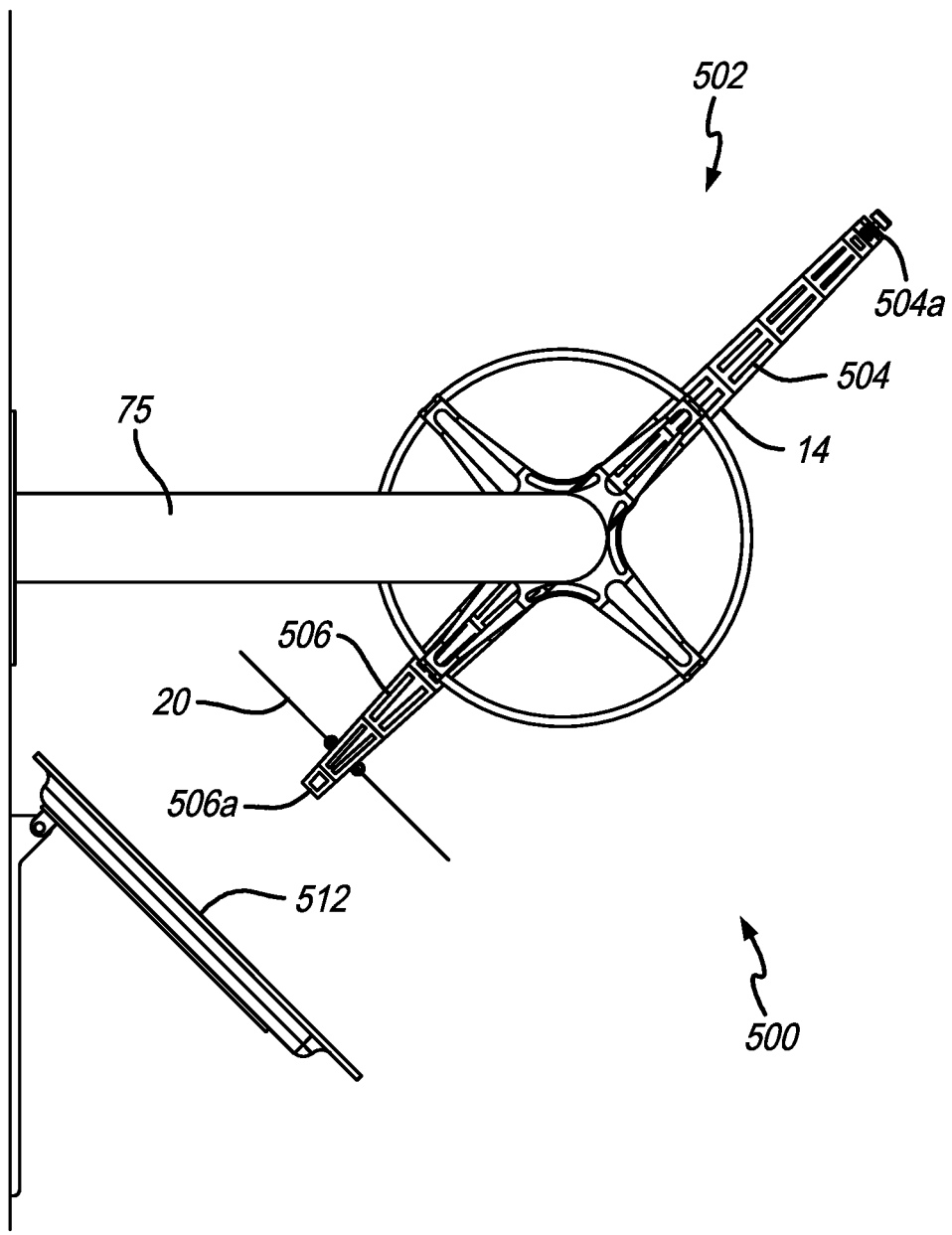
FIG. 50 is a top plan view of the rotatable imaging system of FIG. 46 with the first portion and the second portion in the home position.
Figure 51:
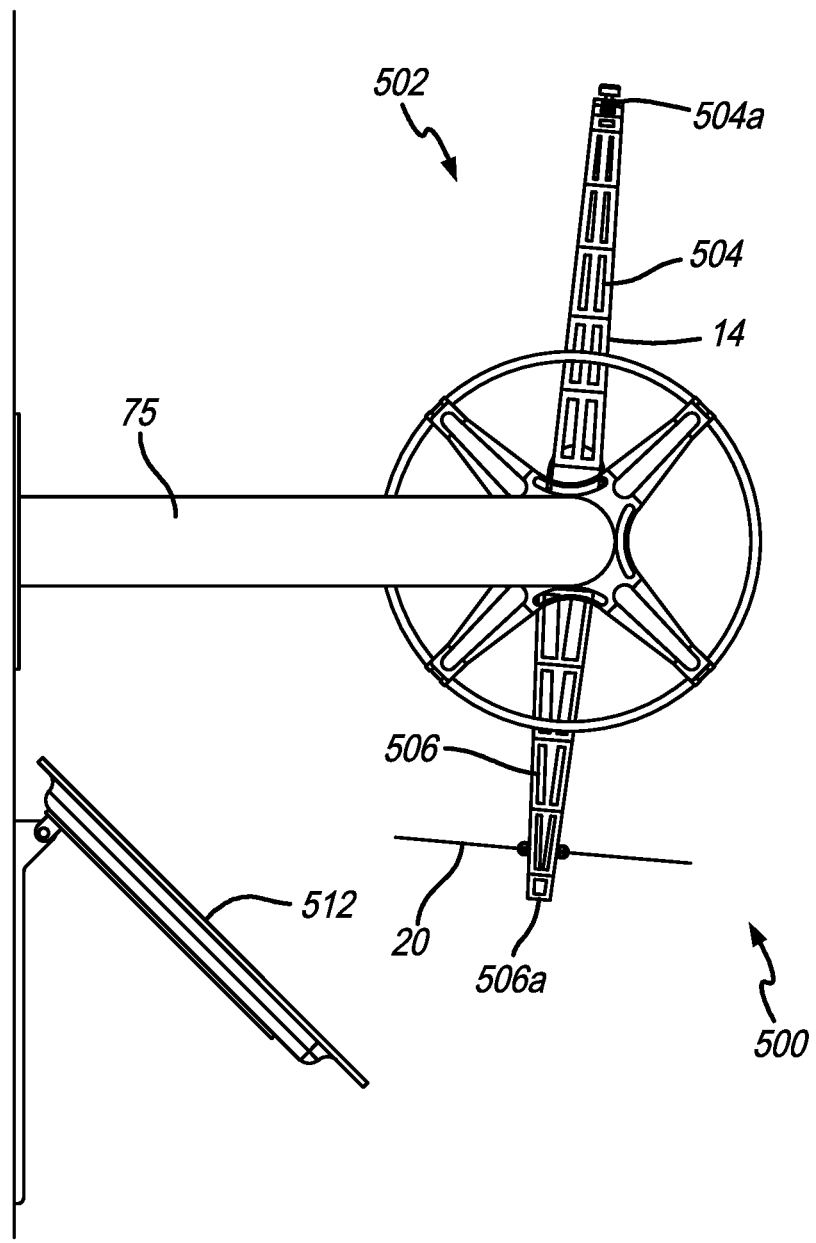
FIG. 51 is a top plan view of the rotatable imaging system of FIG. 46 with the rotating unit rotating during a scan.

After proper alignment has been made (discussed further below), the second portion 506 rotates to the home position, as shown in FIG. 50. At this point, the first and second portions 504 and 506 (and the entire rotating unit 502) are in the home position and the system 500 is ready to take a scan of the subject. In this position, the distal ends 504*b* and 506*b* of the first and second portions 504 and 506 (and the imaging camera(s) and the backdrop) are approximately 180° from one another. In another embodiment, the step shown in FIG. 48 can be omitted and the first portion 504 and the second portion 506 can rotate separately from the stowed position to the alignment position, and/or the home position. Either way, after the rotating unit 502 is in the home position, as shown in FIG. 51, the first portion 504 and the second portion 506 are rotatable together about the rotation axis between the home position and the finish position such that the imaging camera 26 can capture a first scan of a subject positioned generally co-axially with the rotation axis.

Figure 52:
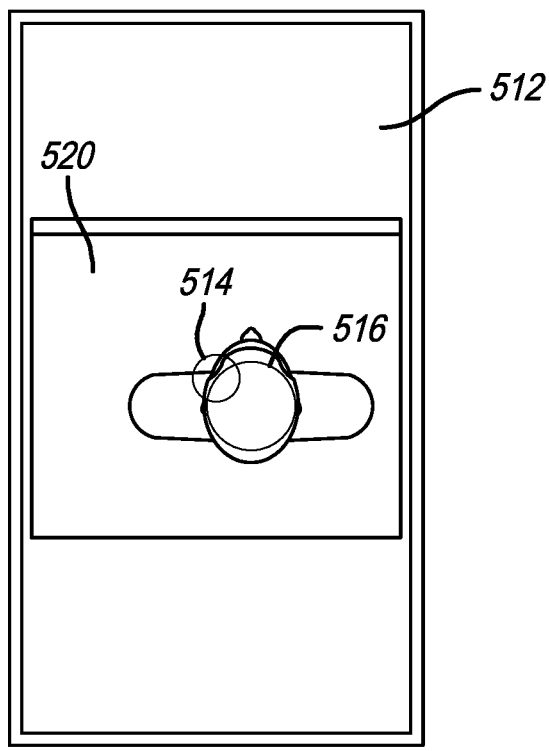
FIG. 52 is a front elevational view of the alignment monitor of the rotatable imaging system of FIG. 46 showing a subject prior to alignment.
Figure 53:
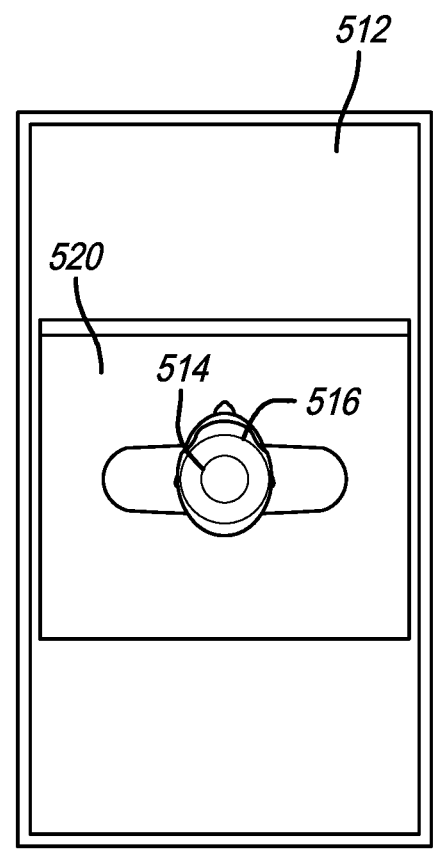
FIG. 53 is a front elevational view of the alignment monitor of the rotatable imaging system of FIG. 46 showing a subject after alignment.

In a preferred embodiment, the alignment monitor 512 includes an alignment system incorporating alignment markings. As discussed above, the alignment markings can simply be circles, lines, arrows or the like that are shown on the monitor. However, in a preferred embodiment the alignment system includes a stationary alignment marking 514 and a movable alignment marking 516. FIGS. 52 and 53 show the stationary alignment markings 514 and the movable alignment markings 516 to be circles for ease of explanation. The alignment camera 146 and alignment system includes the software associated therewith. The stationary alignment marking 514 indicates the optimal alignment position. The movable alignment marking 516 moves with the subjects head (as described below, in a preferred embodiment, the movable alignment marking 516 is actually an image of the subject's head) (or other object to be aligned). The goal of the subject in aligning his/her head is to move the movable alignment marking 516 into concentricity with the stationary alignment marking 514. In other words, the goal of the subject is to move the axis of the movable alignment marking 516 into concentricity with the rotation axis, which is the axis of the stationary alignment marking 514. Because this may be difficult, a predetermined tolerance zone is permitted. In other words, once the movable alignment marking 516 is moved within the tolerance zone, the subject is considered to be aligned and the scan can begin. For example, once the subject is 80% aligned (or within the tolerance zone), the scan can begin. In a preferred embodiment the tolerance zone is between 50% and 100%, in a more preferred embodiment the tolerance zone is between 70% and 100%. In the most preferred embodiment the tolerance zone is between 80% and 100%. Concentricity tolerance (referred to herein as "concentricity") is the diameter of the cylindrical tolerance zone within which the axis of the features, in this case the rotation axis, must lie. For an explanation of concentricity and tolerance zones see U.S. Pat. No. 6,742,936, the entirety of which is incorporated herein by reference. The '936 patent deals with the concentricity of ferrules, but the same principles of alignment can be applied to the alignment system described herein.

Figure 54:
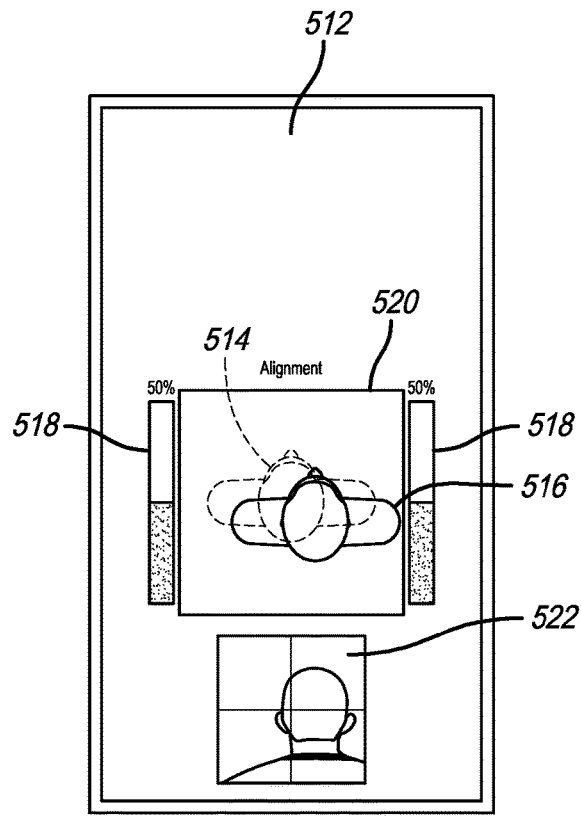
FIG. 54 is a front elevational view of the alignment monitor of the rotatable imaging system of FIG. 46 showing a subject outside of the tolerance zone.
Figure 55:
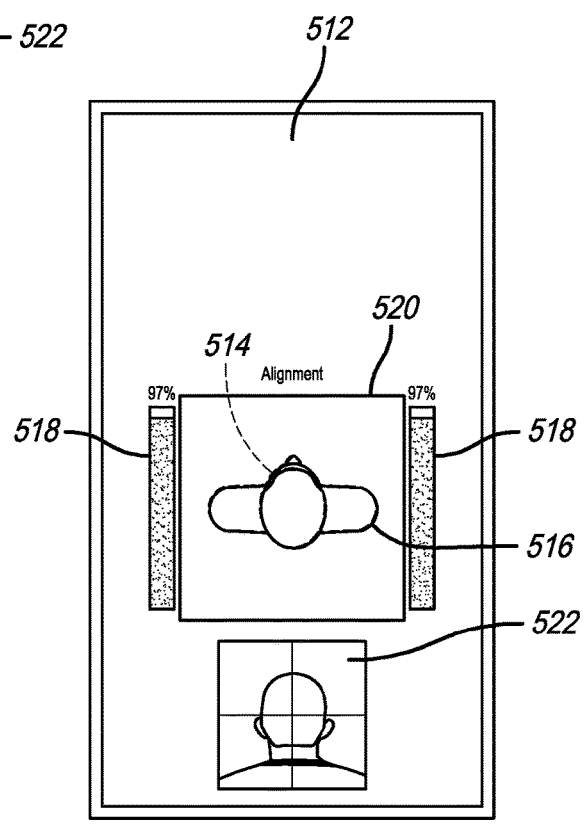
FIG. 55 is a front elevational view of the alignment monitor of the rotatable imaging system of FIG. 46 showing a subject within the tolerance zone.

FIGS. 54-55 eliminate the circles of FIGS. 52-53 and instead show a stationary alignment marking 514 in hidden lines that is a snapshot image of the subject and a movable alignment marking 516 shown in solid lines that is the actual live image being taken in real time by the alignment camera 146. In use, the software snaps a picture or image of the subject in the optimal centered position (which becomes the stationary alignment marking 514) and then presents it as a transparent overlay to the live image, which is the movable alignment marking 516. This provides the subject with a point of reference (the stationary alignment marking 514) to align to. It will be appreciated that the stationary alignment marking 514 image is taken by the alignment camera 146 as the subject moves their head around and shown on the alignment monitor 512. Establishing the stationary alignment marking 514 can be done manually or automatically. If it is done manually, the operator chooses a point where they believe the patient is optimally centered and then snaps the picture (by pushing a button, clicking a mouse, etc.). This establishes the stationary alignment marking 514. In a preferred embodiment, this action (pushing the button) also begins the arms rotating to the home position to take the scan. The subject then uses the movable alignment marking 516 (the live image), the meters 518 (described below) and arrows 519 on the screen to stay centered during the scan. As shown in FIGS. 54-55, in a preferred embodiment, the monitor includes meters 518 on either side of the alignment window 520 to show the quality of the alignment. Prior to establishment of the stationary alignment marking 514, the meters 518 indicate to the subject how close they are to being centered (as described below). After establishment of the stationary alignment marking, and during the scan, the meters 518 indicate to the subject how close the movable alignment marking 516 (the live image of their head) is to the stationary alignment marking. In other words, during the scan, the meters 518 show the concentricity and help the subject move until they are within the tolerance zone. As shown, in FIG. 54, the subject is outside of the tolerance zone at 50%. As shown, in FIG. 55, the subject is inside the tolerance zone at 97%, and a scan can now be taken. The meters 518 can be colored so that when the person is out of the tolerance zone the meters are red or yellow and when the person is in the tolerance zone the meters are green. The window 522 below the alignment window 520 displays the live view of the imaging camera 26.

With reference to FIGS. 54-55, in a preferred embodiment, the use of the system to generate the stationary alignment marking 514 in a preferred embodiment is as follows. First, the software takes an empty image, which is an image without the person in the frame, using the overhead alignment camera 146 and then stores it to memory. Preferably, the memory is random access memory. However, those of ordinary skill in the art will appreciate that the memory can be flash memory, a hard disk drive, networked storage, or any other form of data storage that is accessible by the software. Then, the person steps into the frame, and a top-down image including the person's head, captured by the overhead alignment camera 146, is visible on the alignment monitor 512. The software creates a differential map, which is a pixel map or bitmap that indicates the differences between the empty image and the top-down image including the person's head, to detect the person's head (the person's head as indicated on the differential map hereinafter referred to as the "detected head"). In a preferred embodiment, the software is receiving a live feed from the overhead alignment camera 146 and is thus constantly creating new differential maps of the live feed against the empty image. Preferably, the software averages a number of differential maps generated over a period of time. When the software detects that the differential map or average differential maps includes an equal number of pixels from the empty image in front of the detected head and behind the detected head, then the person's head is considered to be aligned along the front-rear axis. Similarly, when the software detects that the differential map includes an equal number of pixels on the left side of the detected head and on the right side of the detected head, the person's head is considered to be aligned along the left-right axis. When the software considers that the person's head is aligned along the front-rear and left-right axis, the software determines that the person's head is ideally aligned. Then, the software can indicate via the meters 518 that the person's head is ideally aligned or within a certain percentage of ideally aligned. As explained in the preceding paragraph, a stationary alignment marking 514 image can then be either manually or automatically generated, using the overhead alignment camera 146 as explained in the preceding paragraph.

After the stationary alignment marking 514 image is generated, the software uses a similar process to align the moveable alignment marking 516 with the stationary alignment marking 514. That is, the software creates one or more differential maps between the stationary alignment marking 514 image and the live feed image containing the person's head. Then, using the differential map(s) to determine the location of a detected head in relation to the stationary alignment marking 514 using the same process described above, the software can provide a display on the alignment monitor 512 that indicates via the meters 518 whether the person's head is aligned (within a certain range) with the stationary alignment marking 514, as described above. This is referred to herein as a comparison percentage. In an embodiment, if the person moves outside of the preferred range or tolerance zone, an arrow appears on the monitor indicating to the subject to move the indicated direction to get back into the tolerance zone or in better alignment. For example, if the subject moves too far to the right, not only will the percentage drop on the meters, but a left arrow will appear on the alignment monitor 512.

In a preferred embodiment, the differential map is generated and the subject's head is detected using functions in the open-source OpenCV library. However, it will be understood by those of ordinary skill in the art that any image processing library or software capable of object detection can be used.

In a preferred embodiment, the alignment monitor 512 is large enough so that the alignment window 520 can be shown centrally, as shown in FIGS. 52-55, or at the top or the bottom of the alignment monitor 512. This allows for scans taken with the subject looking straight ahead, tilted up or tilted down, similar to the embodiments shown in FIGS. 24A-24C. Also, as shown in FIGS. 47-48, in a preferred embodiment, the alignment monitor 512 is pivotal between a stowed position (FIG. 47) and a use position (FIG. 48) where it is generally perpendicular to a vertical plane that bisects the first and second portions 504 and 506 when they are in the home position.

Figure 56:
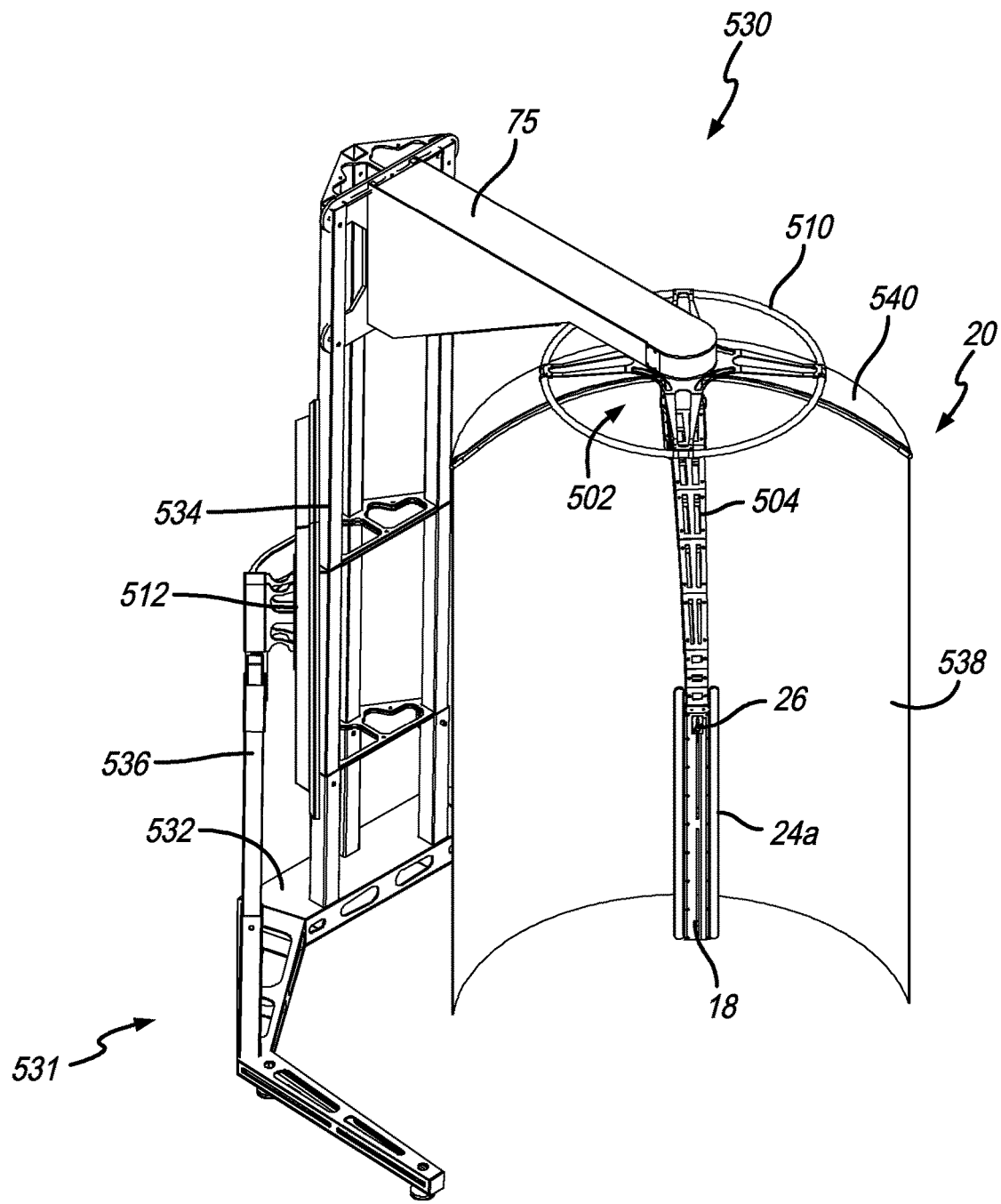
FIG. 56 is a perspective view of a rotatable imaging system in accordance with another preferred embodiment of the present invention.
Figure 57:
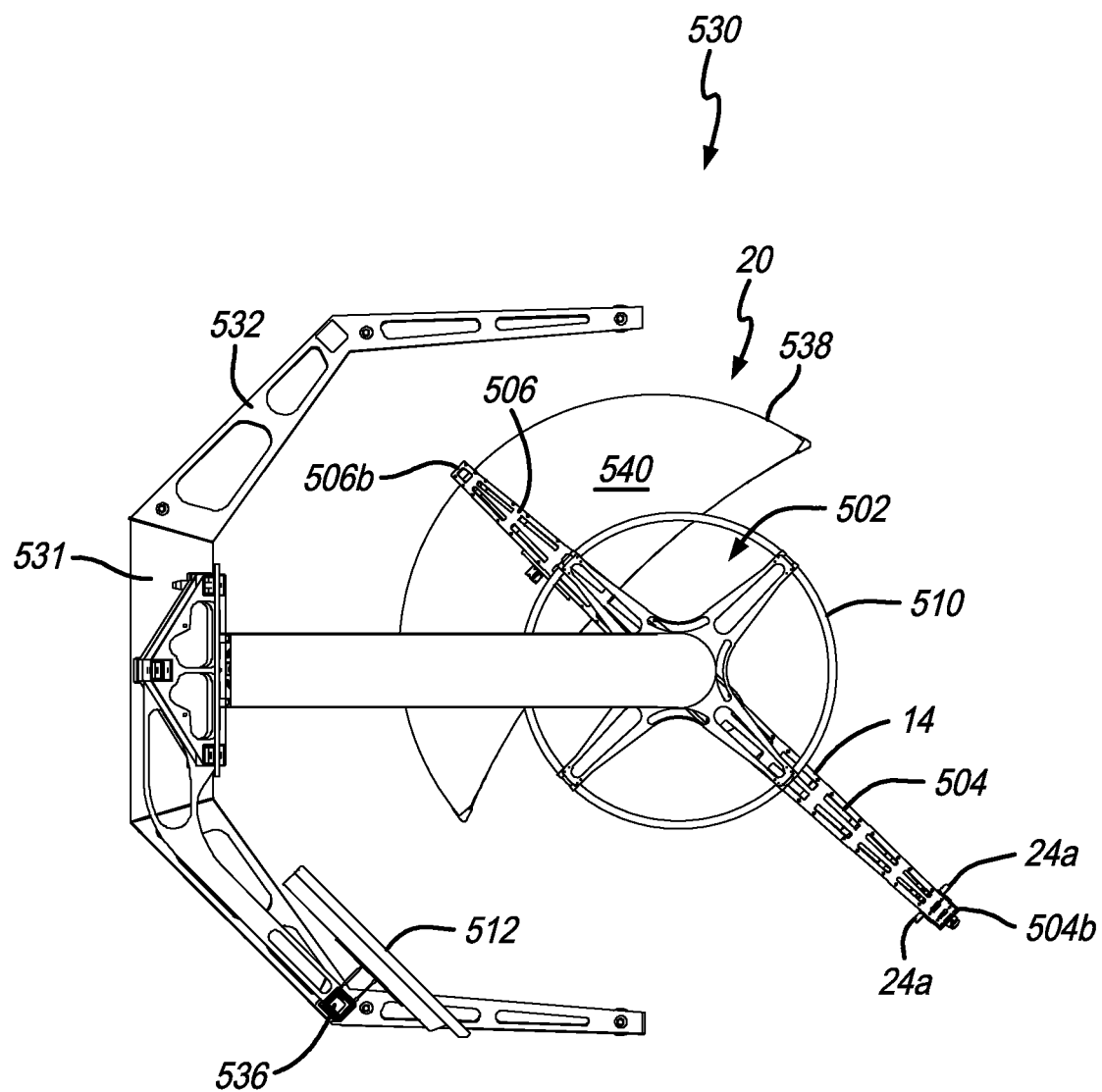
FIG. 57 is a top plan view of the rotatable imaging system of FIG. 56.
Figure 58:
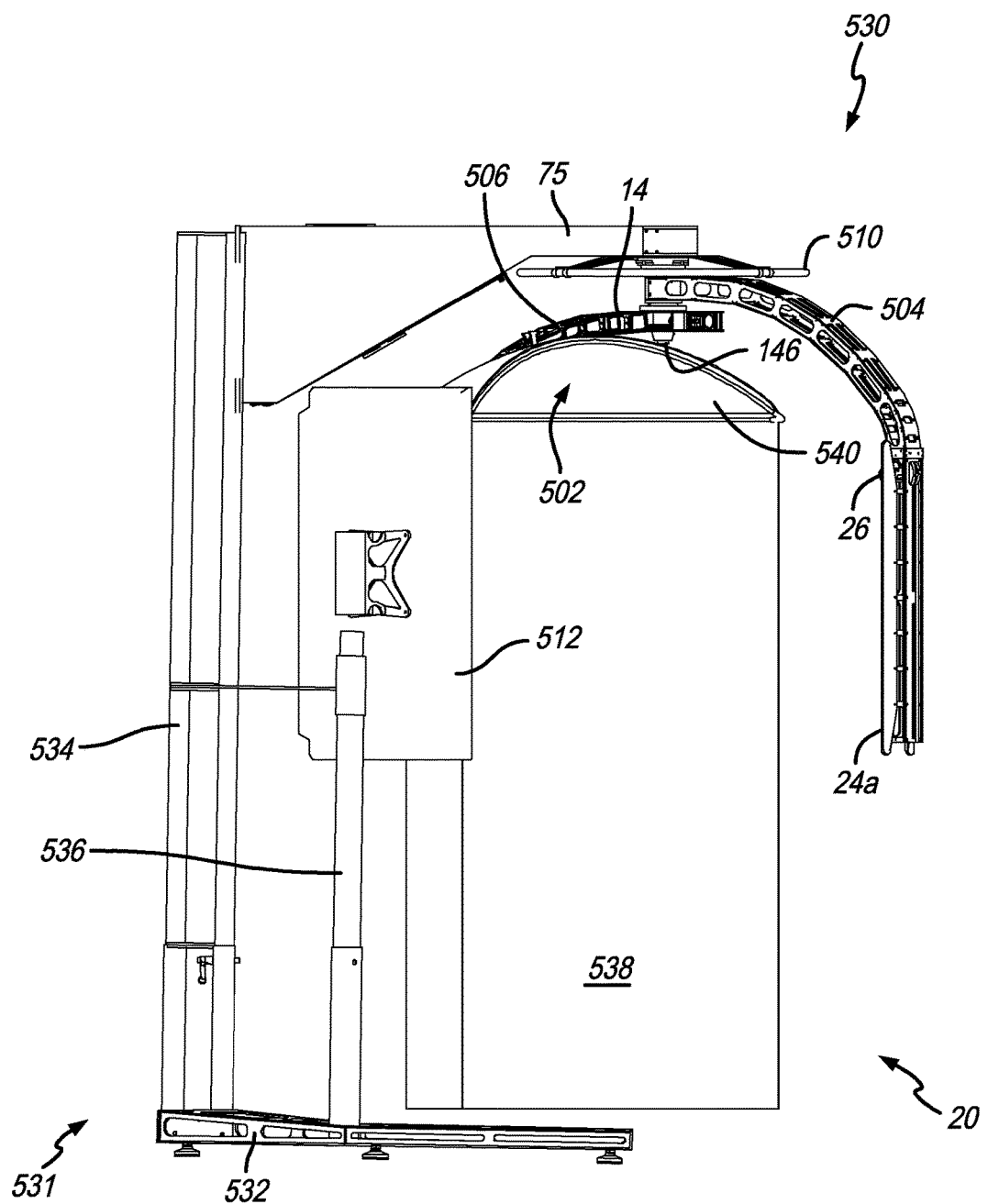
FIG. 58 is an elevational view of the rotatable imaging system of FIG. 56.

FIGS. 56-58 show another embodiment of the imaging system 500 discussed above, but where the system is portable (the system is numbered herein as 530). As shown, the system 530 includes a support assembly 531 that includes a base 532 and a vertically oriented support structure 534 extending upwardly from the base 532. The horizontal boom 75 is connected to and supported by the vertically oriented support structure 534. The alignment monitor 512 is supported by a pole 536 that extends upwardly from the base 532. As shown in the drawings, other components such as legs, struts, feet, crossbeams or the like can be included to strengthen the support assembly 531. The system 530 can include a flat or a curved backdrop 20. As shown in FIGS. 56-58, in a preferred embodiment the curved backdrop 20 includes a backdrop portion 538 that is formed as approximately half of a cylinder (thereby arcing approximately 180°) and a hood portion 540 that extends upwardly from the top of the backdrop portion 538. In a preferred embodiment, the pole 536 and/or the vertically oriented support structure 534 are movable up and down for adjustment purposes and/or for stowage purposes. Also, in a preferred embodiment, the horizontal boom 75 is slidable or movable up and down on the vertically oriented support structure 534.

The particular arrangement shown in the figures and described herein is intended to be only exemplary. Various details of the invention may be changed without departing from the scope of the invention. Furthermore, the foregoing description of the preferred embodiment of the invention and best mode for practicing the invention are provided for the purpose of illustration only and not for the purpose of limitation, the invention being defined by the claims.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further any specific numbers noted herein are only examples: alternative implementations may employ differing values or ranges.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. An imaging system comprising:
   a rotating unit that includes an imaging camera, wherein the rotating unit is rotatable between a home position and a finish position about a rotation axis such that the imaging camera can capture a first scan,
   an alignment camera configured to capture a first alignment image of a subject positioned generally co-axially with the rotation axis, and
   at least a first monitor on which the first alignment image is displayed, wherein the first monitor includes at least one alignment marking thereon, wherein the at least one alignment marking includes a stationary alignment marking and a movable alignment marking, and wherein the rotating unit will not rotate from the home position to the finish position unless the stationary alignment marking is within a predetermined tolerance zone.

2. The imaging system of claim 1 further comprising a motor control system that rotates the rotating unit after the first alignment image is displayed on the first monitor.

3. The imaging system of claim 1 wherein the rotating unit includes a backdrop that rotates opposite of the imaging camera.

4. The imaging system of claim 3 further comprising a support assembly that includes a base and a vertically oriented support structure, and a horizontal boom extending outwardly from the vertically oriented support structure, wherein the rotating unit is positioned below the horizontal boom and is adapted to rotate with respect to the horizontal boom about the rotation axis.

5. The imaging system of claim 4 wherein the backdrop includes a curved backdrop portion and a hood portion.

6. An imaging system comprising:
   a rotating unit that includes an imaging camera, wherein the rotating unit is rotatable between a home position and a finish position about a rotation axis such that the imaging camera can capture a first scan,
   an alignment camera configured to capture a first alignment image of a subject positioned generally co-axially with the rotation axis, and
   at least a first monitor on which the first alignment image is displayed, wherein the first monitor includes at least one alignment marking thereon, wherein the at least one alignment marking includes a stationary alignment marking, and wherein the stationary alignment marking is created using a differential map.

7. The imaging system of claim 6 wherein the at least one alignment marking also includes a movable alignment marking that is a live image taken from the alignment camera.

8. The imaging system of claim 7 wherein at least one differential map is created to determine the location of the movable alignment marking in relation to the stationary alignment marking to produce a comparison percentage, and wherein the comparison percentage is displayed on the alignment monitor on a meter.

9. An imaging system comprising:
   a rotating unit that includes an imaging camera, wherein the rotating unit is rotatable about a rotation axis, wherein the rotating unit includes a first portion and a second portion that are rotatable about the rotation axis, wherein the first portion and the second portion each have a proximal end through which the rotation axis extends and a distal end that is positioned away from the rotation axis, wherein the imaging camera is associated with the distal end of the first portion and a backdrop is associated with the distal end of the second portion, wherein the first portion and the second portion are rotatable from a stowed position where the first portion and the second portion are in substantial vertical alignment and a home position where the distal ends of the first portion and the second portion are approximately 180° from one another with respect to the rotation axis, and wherein the first portion and the second portion are rotatable together between the home position and a finish position such that the imaging camera can capture a first scan of a subject positioned generally co-axially with the rotation axis.

10. The imaging system of claim 9 wherein the first portion and the second portion are separately rotatable about the rotation axis.

11. The imaging system of claim 9 wherein the first portion and the second portion at least partially overlap in a vertical direction when in the stowed position.

12. The imaging system of claim 9 further comprising a horizontal boom having a first end that is adapted to be secured to a wall or other vertically oriented support structure and a second end to which the rotating unit is rotatably attached, and wherein in the stowed position the first portion and the second portion are in substantial vertical alignment with the horizontal boom.

13. The imaging system of claim 9 wherein distal ends of the first portion and the second portion remain approximately 180° from one another when the first portion and the second portion rotate from the home position to the finish position.

14. The imaging system of claim 9 further comprising an alignment camera configured to capture a first alignment image of a subject positioned generally co-axially with the rotation axis, and at least a first monitor on which the first alignment image is displayed.

15. The imaging system of claim 14 wherein the alignment camera is positioned such that it is located along the same axis as the rotation axis.

16. The imaging system of claim 9 wherein the first monitor includes at least one alignment marking thereon.

17. The imaging system of claim 16 wherein the at least one alignment marking includes a stationary alignment marking, and wherein the stationary alignment marking is created using a differential map.

18. The imaging system of claim 17 wherein the at least one alignment marking also includes a movable alignment marking that is a live image taken from the alignment camera.

19. The imaging system of claim 18 wherein at least one differential map is created to determine the location of the movable alignment marking in relation to the stationary alignment marking to produce a comparison percentage, and wherein the comparison percentage is displayed on the alignment monitor on a meter.

20. The imaging system of claim 9 further comprising a support assembly that includes a base and a vertically oriented support structure, and a horizontal boom extending outwardly from the vertically oriented support structure, wherein the rotating unit is positioned below the horizontal boom and is adapted to rotate with respect to the horizontal boom about the rotation axis.

* * * * *